(12) United States Patent
Matsiev et al.

(10) Patent No.: US 9,173,600 B2
(45) Date of Patent: Nov. 3, 2015

(54) SYSTEMS AND METHODS FOR THE IDENTIFICATION OF COMPOUNDS IN MEDICAL FLUIDS USING ADMITTANCE SPECTROSCOPY

(75) Inventors: Leonid Matsiev, San Jose, CA (US); James W. Bennett, Santa Clara, CA (US); Michael J. Weickert, Emerald Hills, CA (US)

(73) Assignee: S.E.A. Medical Systems, Inc., Emerald Hills, CA (US)

( * ) Notice: Subject to any disclaimer, the term of this patent is extended or adjusted under 35 U.S.C. 154(b) by 589 days.

(21) Appl. No.: 12/796,567

(22) Filed: Jun. 8, 2010

(65) Prior Publication Data

US 2010/0305499 A1 Dec. 2, 2010

Related U.S. Application Data

(60) Provisional application No. 61/185,148, filed on Jun. 8, 2009, provisional application No. 61/230,057, filed on Jul. 30, 2009, provisional application No. 61/240,835, filed on Sep. 9, 2009, provisional application No. 61/262,155, filed on Nov. 18, 2009, provisional application No. 61/302,174, filed on Feb. 8, 2010.

(51) Int. Cl.
*G01N 27/06* (2006.01)
*G01N 30/96* (2006.01)
(Continued)

(52) U.S. Cl.
CPC .............. *A61B 5/145* (2013.01); *A61B 5/4839* (2013.01); *A61M 5/172* (2013.01); *G01N 27/026* (2013.01);
(Continued)

(58) Field of Classification Search
CPC ..... G01N 27/06; G01N 30/96; G01N 27/021; G01N 27/3271; G01N 2030/965; G01N 33/5438; G01N 27/403; G01N 27/126; G01N 27/12; G01N 27/60; G01N 33/0031; G01N 27/002; G01N 27/02; G01N 27/041; G01N 27/04; G01N 33/18; G01N 11/00; G01N 33/4905; G01N 11/06; G01N 33/2823; G01N 33/30; G01N 33/2805; G01N 33/2888; G01N 5/02; B01J 19/0046; B01J 2219/00527; B01J 2219/00585; F16N 29/00
USPC .............. 436/150, 149, 151; 73/53.01, 53.06; 604/67, 65; 324/693
See application file for complete search history.

(56) References Cited

U.S. PATENT DOCUMENTS 3,286,992 A 11/1966 Armeniades et al.
4,029,554 A * 6/1977 Ellison ....................... 205/794.5
(Continued)

FOREIGN PATENT DOCUMENTS

EP 0499217 B1 1/1996
EP 1739585 A2 1/2007
(Continued)

OTHER PUBLICATIONS

Bauerle, J.E.; Study of solid electrolyte polarization by a complex admittance method: J. of Physics and Chem. of Solids; vol. 30; No. 12; pp. 2657-2670; Dec. 1969.
(Continued)

*Primary Examiner* — Krishnan S Menon
*Assistant Examiner* — Dwan A Gerido
(74) *Attorney, Agent, or Firm* — Shay Glenn LLP

(57) ABSTRACT

Described herein are devices, systems, and methods for determining the composition of fluids, and particularly for describing the identity and concentration of one or more components of a medical fluid such as intravenous fluid. These devices, systems and methods take multiple complex admittance measurements from a fluid sample in order to identify the identity and the concentration of components of the fluid. The identity and concentration of all of the components of the solution may be simultaneously and rapidly determined. In some variations, additional measurement or sensing modalities may be used in addition to admittance spectroscopy, including optical, thermal, chemical, etc.

29 Claims, 42 Drawing Sheets

(51) Int. Cl.
    *G01N 27/12* (2006.01)
    *G01N 27/60* (2006.01)
    *A61B 5/145* (2006.01)
    *A61B 5/00* (2006.01)
    *A61M 5/172* (2006.01)
    *G01N 27/02* (2006.01)
    *A61B 5/1455* (2006.01)

(52) U.S. Cl.
    CPC ........... *A61B 5/14557* (2013.01); *A61B 5/7267* (2013.01); *A61M 2205/3523* (2013.01); *A61M 2205/3592* (2013.01)

(56) References Cited

U.S. PATENT DOCUMENTS

| | | | |
|---|---|---|---|
| 4,132,944 A | 1/1979 | Bentz | |
| 4,601,820 A | 7/1986 | Leason | |
| 4,810,963 A | 3/1989 | Blake et al. | |
| 5,260,665 A | 11/1993 | Goldberg et al. | |
| 5,260,667 A | 11/1993 | Garcia-Golding et al. | |
| 5,425,867 A | 6/1995 | Dawson et al. | |
| 5,569,591 A | 10/1996 | Kell et al. | |
| 5,612,622 A | 3/1997 | Goldman et al. | |
| 5,772,688 A | 6/1998 | Muroki | |
| 5,792,668 A * | 8/1998 | Fuller et al. | 436/149 |
| 5,992,643 A | 11/1999 | Scrogham et al. | |
| 6,028,433 A * | 2/2000 | Cheiky-Zelina et al. | 324/663 |
| 6,182,504 B1 | 2/2001 | Gaisford | |
| 6,449,580 B1 | 9/2002 | Bardetsky et al. | |
| 6,556,001 B1 | 4/2003 | Wiegand et al. | |
| 6,690,181 B1 | 2/2004 | Dowdeswell et al. | |
| 6,771,074 B2 | 8/2004 | Zou et al. | |
| 6,853,203 B2 | 2/2005 | Beylich et al. | |
| 6,885,960 B2 | 4/2005 | Wagner et al. | |
| 6,969,468 B2 | 11/2005 | Stone et al. | |
| 6,970,738 B1 | 11/2005 | Othman et al. | |
| 6,989,680 B2 | 1/2006 | Sosnowski et al. | |
| 6,990,422 B2 | 1/2006 | Laletin et al. | |
| 7,011,631 B2 | 3/2006 | Davis et al. | |
| 7,043,372 B2 | 5/2006 | Koehler et al. | |
| 7,049,831 B2 | 5/2006 | Wooton et al. | |
| 7,078,910 B2 | 7/2006 | Hirthe et al. | |
| 7,106,075 B2 | 9/2006 | Hu | |
| 7,109,729 B2 | 9/2006 | Schilowitz et al. | |
| 7,124,120 B2 | 10/2006 | Wikiel et al. | |
| 7,143,637 B1 | 12/2006 | McBrearty et al. | |
| 7,154,102 B2 | 12/2006 | Poteet et al. | |
| 7,218,395 B2 | 5/2007 | Kaye et al. | |
| 7,250,775 B1 | 7/2007 | Collins et al. | |
| 7,253,644 B2 | 8/2007 | Song | |
| 7,270,733 B2 | 9/2007 | Wikiel et al. | |
| 7,315,767 B2 | 1/2008 | Caduff et al. | |
| 7,317,525 B2 | 1/2008 | Rzasa et al. | |
| 7,474,971 B2 | 1/2009 | Hu et al. | |
| 7,581,434 B1 | 9/2009 | Discenzo et al. | |
| 7,621,181 B2 | 11/2009 | Cammarata et al. | |
| 8,328,082 B1 | 12/2012 | Bochenko et al. | |
| 8,355,753 B2 | 1/2013 | Bochenko et al. | |
| 8,385,972 B2 | 2/2013 | Bochenko et al. | |
| 8,394,053 B2 | 3/2013 | Bochenko et al. | |
| 2002/0180570 A1 | 12/2002 | Facer et al. | |
| 2002/0183693 A1 | 12/2002 | Peterson et al. | |
| 2003/0048432 A1* | 3/2003 | Jeng et al. | 356/39 |
| 2003/0072549 A1 | 4/2003 | Facer et al. | |
| 2003/0159741 A1 | 8/2003 | Sparks | |
| 2003/0204330 A1 | 10/2003 | Allgeyer | |
| 2004/0020772 A1 | 2/2004 | Bas et al. | |
| 2004/0079652 A1 | 4/2004 | Vreeke et al. | |
| 2004/0126814 A1 | 7/2004 | Singh et al. | |
| 2004/0142405 A1 | 7/2004 | Alfonta et al. | |
| 2004/0171983 A1 | 9/2004 | Sparks et al. | |
| 2005/0023155 A1 | 2/2005 | Sawyer et al. | |
| 2005/0266582 A1 | 12/2005 | Modlin et al. | |
| 2006/0105467 A1 | 5/2006 | Niksa et al. | |
| 2007/0072286 A1 | 3/2007 | Orsel et al. | |
| 2007/0191700 A1 | 8/2007 | Say et al. | |
| 2007/0293817 A1 | 12/2007 | Feng et al. | |
| 2008/0053202 A1 | 3/2008 | Rohklin et al. | |
| 2008/0105565 A1 | 5/2008 | Davalos et al. | |
| 2008/0116908 A1 | 5/2008 | Potyrailo et al. | |
| 2008/0167823 A1 | 7/2008 | Koehler et al. | |
| 2008/0172187 A1 | 7/2008 | Koehler et al. | |
| 2009/0102450 A1 | 4/2009 | Da Silva et al. | |
| 2009/0115435 A1 | 5/2009 | Tomlinson | |
| 2009/0115436 A1* | 5/2009 | Koehler et al. | 324/698 |
| 2009/0261847 A1 | 10/2009 | Petrovsky et al. | |
| 2009/0293590 A1 | 12/2009 | Zeng et al. | |
| 2010/0300899 A1* | 12/2010 | Levine et al. | 205/792 |
| 2012/0037266 A1 | 2/2012 | Bochenko | |
| 2012/0065617 A1 | 3/2012 | Matsiev et al. | |
| 2013/0204227 A1 | 8/2013 | Bochenko et al. | |

FOREIGN PATENT DOCUMENTS

| | | |
|---|---|---|
| EP | 2042719 A2 | 4/2009 |
| EP | 2068139 A1 | 6/2009 |
| JP | 2006-138770 | 6/2006 |
| JP | 2008-76227 | 4/2008 |
| WO | WO2004/033003 A1 | 4/2004 |
| WO | WO2005/007223 A2 | 1/2005 |
| WO | WO2006/010310 A1 | 2/2006 |
| WO | WO2007/047004 A2 | 4/2007 |
| WO | WO2007/054700 A1 | 5/2007 |
| WO | WO2008/073931 A2 | 6/2008 |
| WO | WO2008/133656 A2 | 11/2008 |
| WO | WO2008131609 A1 | 11/2008 |
| WO | WO2009/114115 A1 | 9/2009 |

OTHER PUBLICATIONS

Cole et al.; Dispersion and absorption in dielectrics I. alternation current characteristics: J. Chem. Phys.; vol. 9 No. 4; pp. 341-351; Apr. 1941.

Fischler et al.; Polarisation impedance of pacemaker electrodes: in vitro studies simulating practical operation; Med. Biol. Eng. and Comput.; vol. 19; No. 5; pp. 579-588; Sep. 1981.

Sluyters J.H.; On the impedance of galvanic cells: I. Theory.; Rec. Trav Chim.; vol. 79; No. 10; pp. 1092-1100; (the year of publication is sufficiently earlier than the effective U.S. filing date and any foreign priority date) 1960.

Sluyters J.H.; On the impedance of galvanic cells: II. Experimental verification.; Rec. Trav Chim.; vol. 79; No. 10; pp. 1101-1110; (the year of publication is sufficiently earlier than the effective U.S. filing date and any foreign priority date) 1960.

Smith, P.H.; An improved transmission line calculator; Electronics.; vol. 17; No. 1; pp. 130-133; Jan. 1944.

Tian et al.; Drug signature using impedance spectroscopy technique; BMES/EMBS Proc. Of the First Joint Conf., Atlanta, Georgia; vol. 2; pp. 813; Oct. 13, 1999.

Carter, C.W.; Graphic Representation of the impedance of networks containing resistance and two reactances: Bell Sys. Tech. J.;vol. 4; pp. 387-401; Jul. 1925.

Smith, P.H.; Transmission line calculator; Electronics.; pp. 29-31; Jan. 1939.

Bow, Sing-Tze; Pattern Recognition and Image Preprocessing; 2nd ed.; Marcel Dekker; pp. 16-20, 29-32, 112-117, 197-199, and 511-513 (21 total pgs.); 2002.

Bruun, H. H.; Hot-wire anemometry: principles and signal analysis; Oxford University Press; pp. 34-37 & 112-121 (14 total pgs); 1995.

Cole-Parmer (Tech. Library); Why Measure Viscosity? What is it?; 10 pgs.; printed Sep. 8, 2010 (http://www.coleparmer.com/techinfo/techinfo.asp?htmlfile=why-meas-viscosity.htm&ID=933).

Endress+Hauser; Bubble Detection Sensor OUSAF13; Tech. Info. Doc. No. TI921C/24/ae; 4 pgs.; printed/accessed Sep. 10, 2010 (https://portal.endress.com/wa001/dla/5000195 1410/000/00/TI921CAE.pdf).

Fouke et al.; Sensor for measuring surface fluid conductivity in vivo; IEEE Trans Biomed Eng.; vol. 35; No. 10; pp. 877-881; Oct. 1988.

(56) References Cited

OTHER PUBLICATIONS

Gonzalez et al.; Fluid flow induced by nonuniform ac electric fields in electrolytes on microelectrodes. ii. a linear double-layer analysis; Phys. Rev. E; vol. 61; No. 4; pp. 4019R4028; Apr. 2000.

Green et al.; Fluid flow induced by nonuniform ac electric fields in electrolytes on microelectrodes. i. experimental measurements; Phys. Rev. E; vol. 61; No. 4; pp. 4011R4018; Apr. 2000.

Green et al.; Fluid flow induced by nonuniform ac electric fields in electrolytes on microelectrodes. iii. observation of streamlines and numerical simulation; Phys. Rev. E; 66; 026305; 2002.

Green et al.; Impedance based flow sensors; Microtechnologies for the New Millennium; 2005 SPIE; May 9-11, 2005.

Helmholtz; Studien über elektrische Grenzschichten. Annalen der Physik und Chemie; Neue Folge; 7 (7), p. 337-382; 1879—(translation: P. E. BOCQUE; Studies of electric boundary layers; Dep. Engineering Research Univ. Mich.; 33; pp. 5-47; 1951).

Homola, Jiri (Ed.); Surface Plasmon Resonance Based Sensors; Springer Series on Chemical Sensors and Biosensors; vol. 4; pp. 134-138; 2006.

Kikutani et al.; Flowing thermal lens micro-flow velocimeter; Sensors and Actuators B: Chemical; vol. 133; iss. 1; pp. 91-96; Jul. 28, 2008.

Krasser et al.; Simultaneous Measurements at U-tube Density Sensors in Fundamental and Harmonic Oscillation; EUROCON; The Int'l Conf. on "Computer as a tool"; pp. 551-555; Sep. 9-12, 2007.

Kumar et al.; A fibre optic evanescent wave sensor used for the detection of trace nitrites in water; Journal of Optics A: Pure and Applied Optics; vol. 4; pp. 247-250; 2002.

MacDonald et al.; Analysis of impedance and admittance data for solids and liquids; J. Electrochem. Soc.; vol. 124; No. 7; pp. 1022-1030; 1977.

MacDonald; Impedance spectroscopy-emphasizing solid materials and systems; 1st ed.; John Wiley and Sons; pp. 1-4; 1987.

MacDonald; Theory of ac space-charge polarization effects in photoconductors, semiconductors, and electrolytes; Physical Review; vol. 92; No. 1; pp. 4-17; 1953.

Maltoni et al.; Handbook of Fingerprint Recognition; Springer, NY; pp. 137-141; 2003.

Mathioulakis et al.; A pulsed-wire technique for velocity and temperature measurements in natural convection flows; Experiments in Fluids; vol. 18; Nos. 1-2; pp. 82-86; Dec. 1994.

Nixon, M.S. et al.; Feature Extraction and Image Processing; 1st ed.; MPG Books Ltd.; pp. 164-169; 2002.

Oh et al.; Minimization of electrode polarization effect by nanogap electrodes for biosensor applications; The 16th Ann Int'l Conf on Micro Electro Mech Sys 2003; MEMS-03 Kyoto. IEEE; pp. 52-55; Jan. 19-23, 2003.

Omega Engineering; Turbidity Measurement; 4 pgs.; printed/accessed Sep. 10, 2010 (http://www.omega.com/techref/ph-6.html).

Optek; Inline process color measurement (Application note from website; 2 pgs.; printed Sep. 8, 2010 (http://www.optek.com/Application_Note/General/English/7/Inline_Process_Color_Measureme nt.asp).

Orazem et al.; History of Impedance Spectroscopy; Electrochemical Impedance Spectroscopy; John Wiley & Sons; pp. XXV-XXXI; (published online) Feb. 7, 2008.

Potyrailo et al.; Near-Ultraviolet Evanescent-Wave Absorption Sensor Based on a Multimode Optical Fiber; Anal. Chem.; vol. 70; No. 8; pp. 1639R1645; 1998.

Resonance; ElectroChemical Methods; 11 pgs.; printed/accessed from archive Sep. 10, 2010 (http://web.archive.org/web/20061023171937/http://www.resonancepub.com/electrochem.htm).

Richter, Andreas; Differential optical absorption spectroscopy as a tool to measure pollution from space; Spectroscopy Europe; vol. 18; No. 6; pp. 14-21; 2006.

Sarmousakis et al.; Impedance at polarized platinum electrodes in various electrolytes; Journal of the Electrochemical Society; vol. 104; No. 7; pp. 454-459; 1957.

Schirmer et al.; A new method for the determination of membrane permeability by spatially resolved concentration measurement; Meas. Sci. Technol.; vol. 15; No. 9; pp. 195-202; 2004.

"Schwan; Linear and nonlinearelectrode polarization and biological materials; Ann. Biomed. Eng.; vol. 20; pp. 269-288; 1992".

Sensorland.com; How Sensors Work—Understanding pH measurement; 7 pgs.; printed Sep. 8, 2010 (http://www.sensorland.com/HowPage037.html).

Singh, Shyam; Refractive Index Measurement and its Applications; Physica Scripta; vol. 65; No. 2; pp. 167-180; 2002.

Stachowiak et al.; A thermoelectric sensor for fluid flow measurement. principles, calibration and solution for self temperature compensation; Flow Measurement and Instrumentation; vol. 9; iss. 3; pp. 135-141; Sep. 1998.

Test & Measurement World; Analysis of dielectric material properties using LCR meters; www.tmworld.com/contents/pdf/tmw03_05D1_jr.doc; printed/accessed Oct. 26, 2010.

Überall, Herbert; Interference and Steady-State Scattering of Sound Waves; In: Handbook of Acoustics (M. J. Crocker (Ed.); Chap. 4; pp. 47-60; 1998.

Walton et al.; Platinum pacemaker electrodes: origins and effects of the electrode-tissue interface impedance; Pacing Clin. Electrophysiol; vol. 10; pp. 87R99; 1978.

Way et al.; Hot-wire probes for measuring velocity and concentration in helium-air mixtures; AIAA Journal; vol. 8; No. 5; pp. 976R978; 1970.

Bennett et al.; U.S. Appl. No. 12/920,203 entitled "Intravenous Fluid Monitoring," filed Aug. 30, 2010.

Bennett et al.; U.S. Appl. No. 12/875,939 entitled "Multi-Parametric Fluid Determination Systems Using Complex Admittance," filed Sep. 3, 2010.

MacDonald et al.; Fundamentals of Impedance Spectroscopy (Ch. 1/pp. 1-4); in Impedance Spectroscopy: Theory, Experiment, and Applications 2nd Ed.; Barsoukov & MacDonald; pp. 1-4; Mar. 2005.

* cited by examiner

| | 10 | 20 | 30 | 40 | 50 | 60 | 70 | 80 | 90 | 100 |
|---|---|---|---|---|---|---|---|---|---|---|
| Au-Au | 1703 | | | | | | | | | |
| Au-Pd | 1705 | | | | | | | | | |
| Au-Ti | | | | | | | | | | |
| Pd-Pd | | | | | | | | | | |
| Pd-Ti | | | | | | | | | | |
| Ti-Ti | | | | | | | | | | |

| Drug | Concentration | Drug | Concentration |
|---|---|---|---|
| Heparin sodium | 100 units/mL | Carboplatin | 1 mg/mL |
| Insulin (regular) | 1 unit/mL | Cyclophosphamide | 2 mg/mL |
| Midazolam | 0.5 mg/mL | Cytarabine | 2 mg/mL |
| Dopamine | 2 mg/mL | Etoposide | 2 mg/mL |
| Dobutamine | 500 mcg/mL | Fluorouracil | 10 mg/mL |
| Furosemide | 4 mg/mL | Nitroprusside sodium | 0.2 mg/mL |
| Pancuronium | 1 mg/mL | Succinylcholine | 20 mg/mL |
| Vecuronium | 1 mg/mL | Lorazepam | 0.5 mg/mL |
| Atracurium | 0.5 mg/mL | Phenylephrine | 0.4 mg/mL |
| Morphine | 0.5 mg/mL | Potassium chloride | 40 mEq/L |
| Hydromorphone | 0.5 mg/mL | Magnesium sulfate | 200 mg/mL |
| Fentanyl Citrate | 0.02 mg/mL | Sodium chloride | 3% |
| Propofol | 5 mg/mL | Nicardipine | 0.1 mg/mL |
| Epinephrine | 0.008 mg/mL | Vancomycin | 5 mg/mL |
| Norepinephrine | 0.008 mg/mL | Vasopressin | 0.5 u/mL |

FIG. 18A

| Drug | Concentration | Diluent |
|---|---|---|
| Atracurium | 0.5mg/mL | NS |
| Atracurium | 0.5mg/mL | D5W |
| Bupivicaine | 0.10% | NS |
| Bupivicaine | 1.00% | NS |
| Carboplatin | 1 mg/mL | NS |
| Cyclophosphamide | 2 mg/ml | NS |
| Cytarabine | 2 mg/ml | NS |
| Dobutamine | 0.5mg/ml | D5W |
| Dobutamine | 500 mcg/ml | NS |
| Dopamine | 2 mg/ml | NS |
| Epinephrine | 0.008 mg/mL | NS |
| Etoposide | 2 mg/mL | NS |
| Fentalyl + Bupivicaine | 0.002mg/ml+ 0.1% | NS |
| Fentanyl Citrate | 0.002mg/ml | NS |
| Fentanyl Citrate | 0.02 mg/mL | NS |
| Fentanyl Citrate | 0.1mg/ml | NS |
| Fentanyl Citrate | 1mg/ml | SW |
| Fluorouracil | 10 mg/mL | NS |
| Furosemide | 4 mg/mL | NS |
| Heparin + Midazolam | 100U/ml+0.5mg/ml | NS |
| Heparin + Vancomycin | 1000U/ml+5mg/ml | NS |
| Heparin sodium | 0.3U/ml | NS |
| Heparin sodium | 0.3U/ml | D5W |
| Heparin sodium | 1U/ml | NS |
| Heparin sodium | 2U/ml | D5W |
| Heparin sodium | 2U/ml | NS |
| Heparin sodium | 10U/ml | NS |
| Heparin sodium | 10U/ml | D5W |
| Heparin sodium | 30U/ml | NS |
| Heparin sodium | 100U/ml | D5W |
| Heparin sodium | 100U/ml | NS |
| Heparin sodium | 300U/ml | NS |
| Heparin sodium | 1000U/ml | NS |
| Heparin sodium | 1000U/ml | D5W |
| Heparin sodium | 2500U/ml | NS |
| Heparin sodium | 250U/ml | SW |
| Hydromorphone | 0.5 mg/mL | NS |
| Insulin | 0.01U/ml | NS |
| Insulin | 0.05U/ml | NS |
| Insulin | 0.1U/ml | NS |
| Insulin | 0.3U/ml | NS |
| Insulin | 1U/ml | NS |
| Insulin | 3U/ml | NS |
| Insulin | 10U/ml | NS |
| Insulin | 30U/ml | NS |
| Insulin | 100U/ml | NS |
| Insulin | 500U/ml | NS |
| Lorazepam | 0.5 mg/mL | NS |
| Magnesium sulfate | 200 mg/mL | NS |
| Midazolam | 0.5 mg/ml | NS |
| Morphine | 0.5 mg/mL | NS |
| Nicardipine | 0.1 mg/mL | NS |
| Nicardipine | 0.1 mg/ml | D5W |
| Nicardipine | 0.5mg/ml | NS |
| Nitroprusside sodium | 0.2 mg/ml | NS |
| Norepinephrine | 0.008 mg/ml | NS |
| Norepinephrine + Dopamine | 0.008mg/ml+2mg/ml | NS |
| Pancuronium | 1 mg/mL | SW |
| Phenylephrine | 0.1 mg/mL | SW |
| Phenylephrine | 0.4 mg/mL | NS |
| Potassium chloride | 0.001 meq/ml | D5W |
| Potassium chloride | 0.003 meq/ml | D5W |
| Potassium chloride | 0.01 meq/ml | D5W |
| Potassium chloride | 0.04 mEq/ml | NS |
| Potassium chloride | 0.04 meq/ml | D5W |
| Potassium chloride | 0.08 meq/ml | D5W |
| Potassium chloride | 0.1 meq/ml | D5W |
| Potassium chloride | 0.4 meq/ml | D5W |
| Potassium chloride | 0.8 meq/ml | D5W |
| Propofol | 5 mg/ml | NS |
| Propofol | 5mg/ml | D5W |
| Sodium chloride | 3% | D5W |
| Succinylcholine | 20 mg/mL | SW |
| Vancomycin | 5 mg/ml | NS |
| Vasopressin | 0.5 U/ml | NS |
| Vasopressin | 0.5U/ml | D5W |
| Vecuronium | 1 mg/mL | NS |

FIG. 18B

Pancuronium
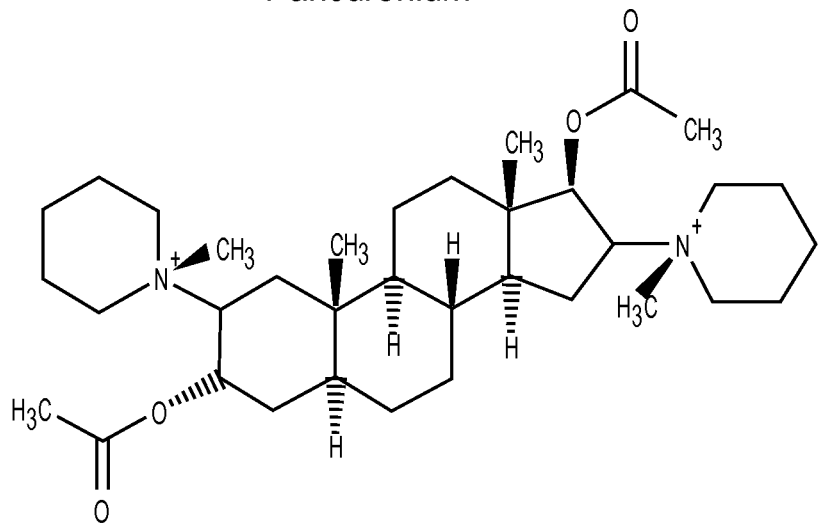
Formula: $C_{35}H_{60}N_2O_4$
Mol. mass: 572.861 g/mol
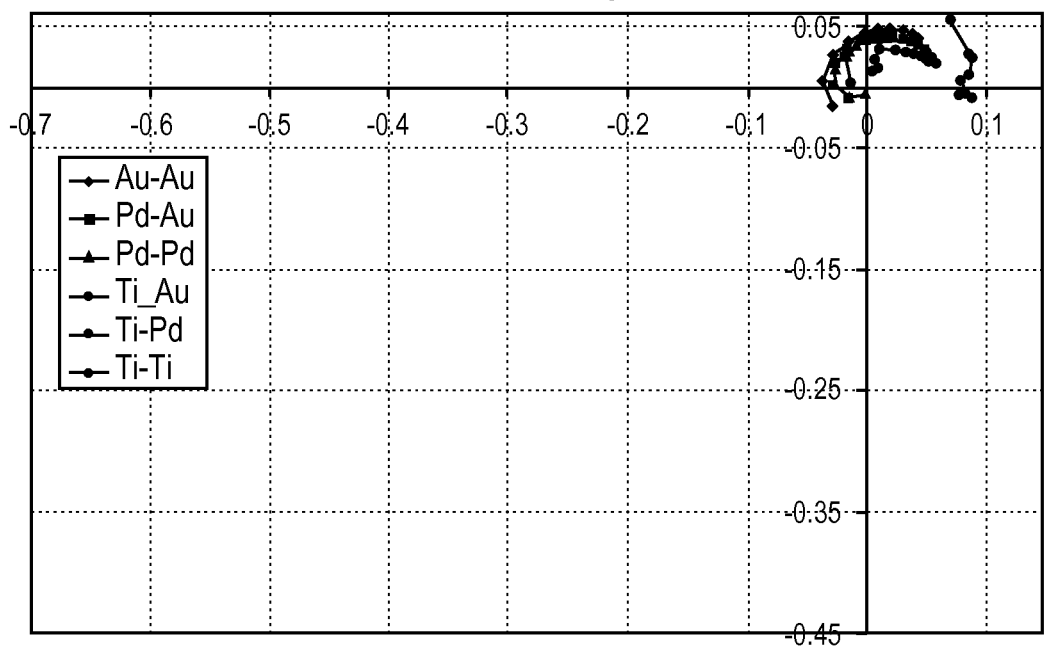
FIG. 20A

Vecuronium
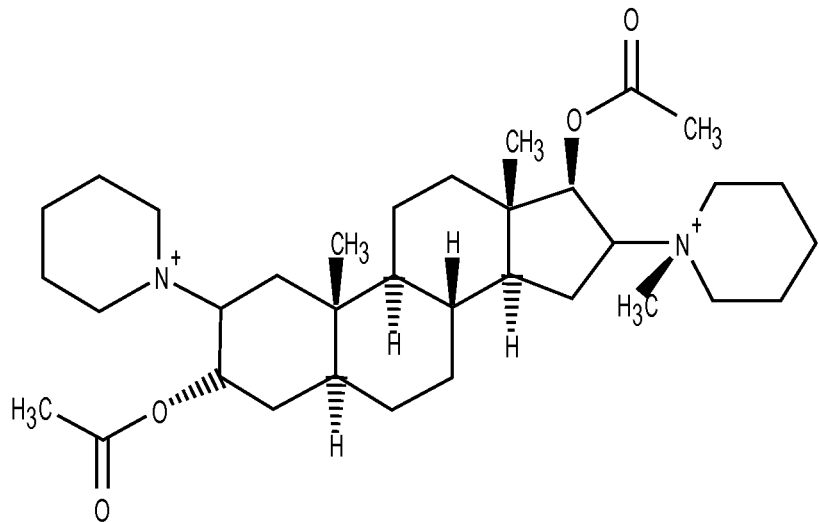
Formula: $C_{34}H_{57}N_2O_4^+$
Mol. mass: 557.827 g/mol
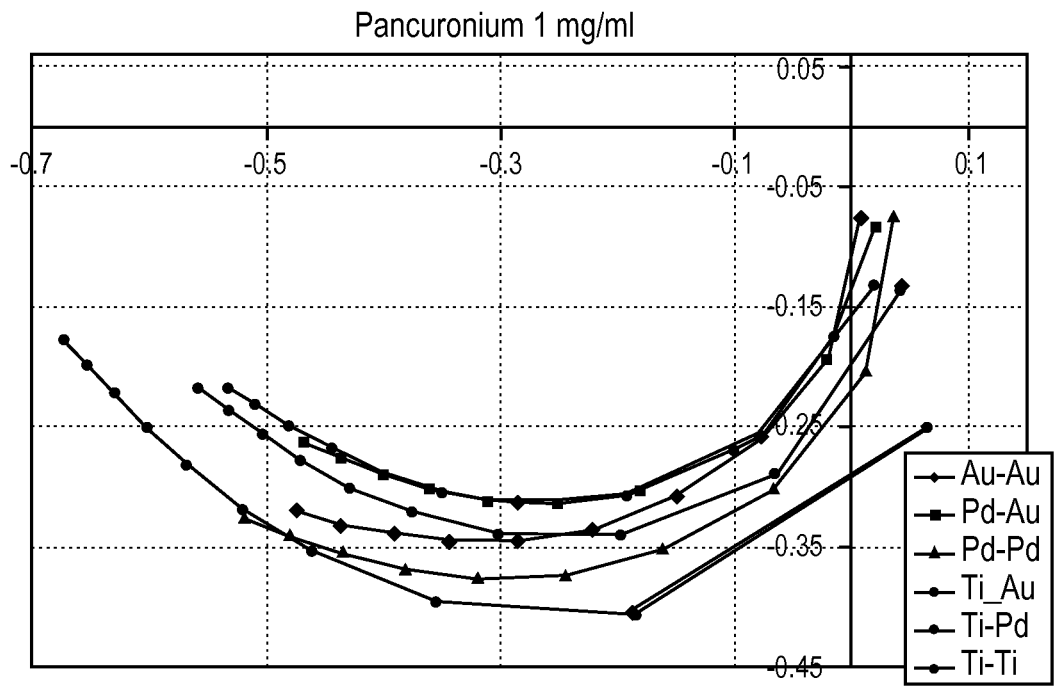
FIG. 20B

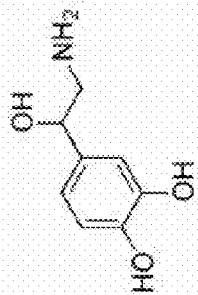
Epinephrine
Formula: $C_9H_{13}NO_3$
Mol. mass: 183.204 g/mol
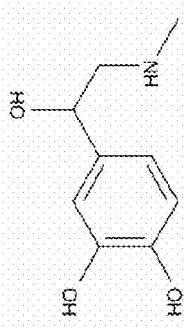
Norepinephrine
Formula: $C_8H_{11}NO_3$
Mol. mass: 169.18 g/mol
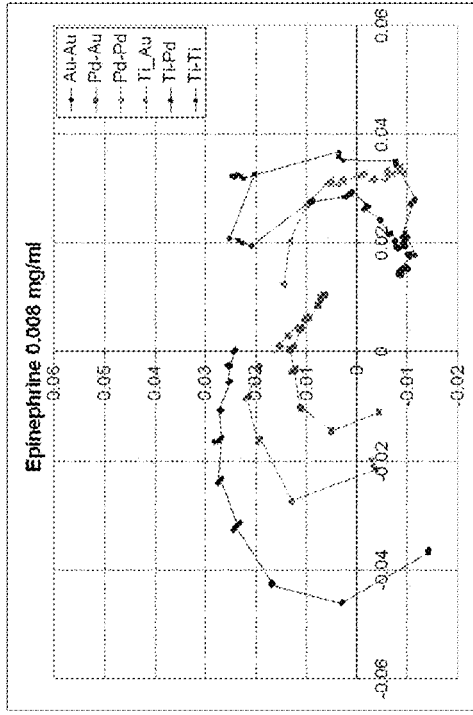
FIG. 21A
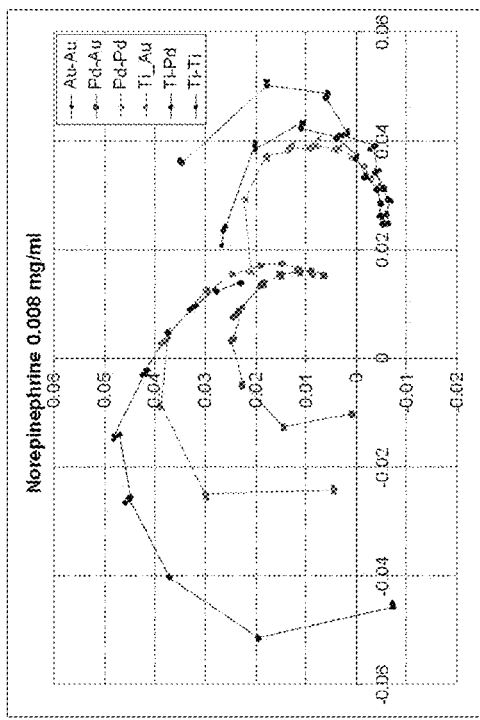
FIG. 21B Morphine
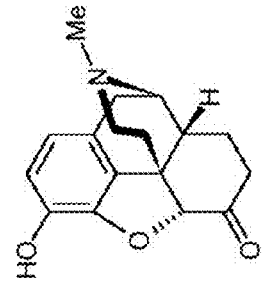
Formula: $C_{17}H_{19}NO_3$
Mol. mass: 285.34 g/mol
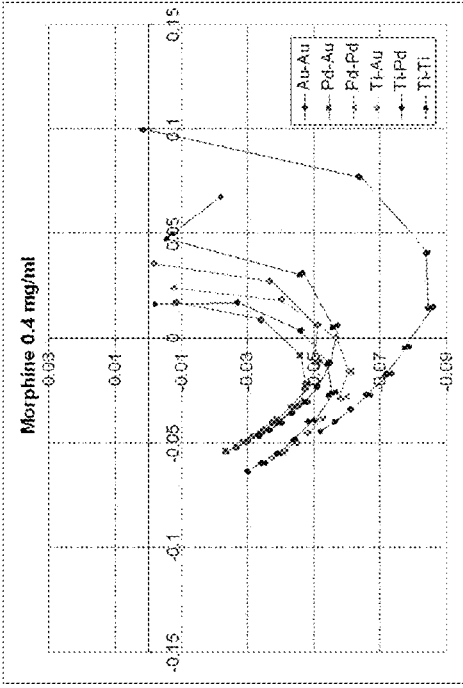
FIG. 22A
Hydromorphone
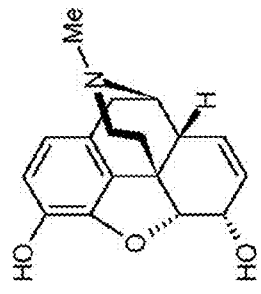
Formula: $C_{17}H_{19}NO_3$
Mol. mass: 285.34 g/mol
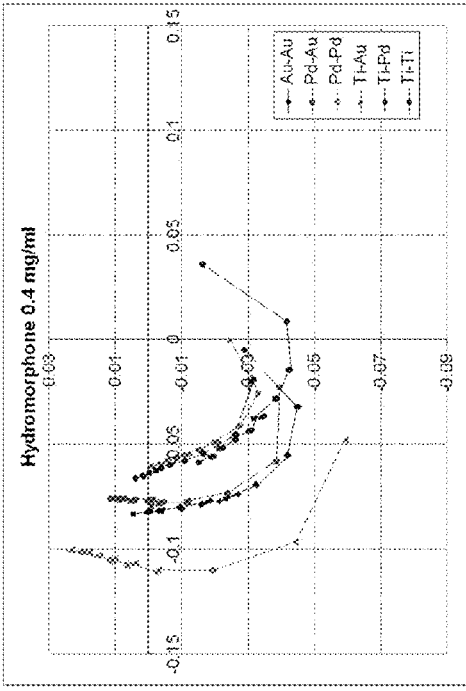
FIG. 22B

SYSTEMS AND METHODS FOR THE IDENTIFICATION OF COMPOUNDS IN MEDICAL FLUIDS USING ADMITTANCE SPECTROSCOPY

CROSS REFERENCE TO RELATED APPLICATIONS

This patent application claims priority to U.S. Provisional Patent Application Ser. No. 61/185,148 (titled "IV SENSING ITEMS FOR PROVISIONAL PATENT APPLICATION"), filed on Jun. 8, 2009; U.S. Provisional Patent Application Ser. No. 61/230,057 (titled "MEASUREMENT AND IDENTIFICATION OF IV FLUIDS"), filed on Jul. 30, 2009; U.S. provisional Patent Application Ser. No. 61/240,835 (titled "APPLICATION OF MULTIPLE SENSORS TO MEASUREMENT AND IDENTIFICATION OF DRUGS"), filed on Sep. 9, 2009; U.S. Provisional Patent Application Ser. No. 61/262,155 (titled, "SYSTEMS AND METHODS FOR THE IDENTIFICATION OF COMPONENTS IN MEDICAL FLUIDS THROUGH THE APPLICATION OF MULTIPLE ELECTRODE ADMITTANCE SPECTROSCOPY"), filed on Nov. 18, 2009; and U.S. Provisional Patent Application Ser. No. 61/302,174 (titled "SYSTEMS AND METHODS FOR MEASUREMENT AND IDENTIFICATION OF DRUG SOLUTIONS"), filed on Feb. 8, 2010.

This application may also be related to PCT Application Serial No. PCT/US2009/001494 (titled "INTRAVENOUS FLUID MONITORING"), filed on Mar. 9, 2009.

All of these patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices, systems and methods described may be used to determine the identity and concentration of one or more, or in some variations all, components in an aqueous solution using admittance spectroscopy. In particular, described herein are devices, systems and methods for using admittance spectroscopy to determine the identity and concentration of components of an intravenous drug solution.

BACKGROUND OF THE INVENTION

Errors in medication provided to a patient are recognized as a serious, and potentially avoidable, problem associated with the delivery of health care.

Medication errors are estimated to account for 7,000 deaths annually, and adverse drug events cause more than 770,000 injuries and deaths each year. Patients who suffer from unintended drug events remain in the hospital an average of 8 to 12 days longer than patients who did not experience such mistakes. Two recent studies, one conducted in Colorado and Utah and the other in New York, found that adverse events occurred in 2.9 and 3.7 percent of hospitalizations, respectively.

Infusion devices are believed to account for up to 35% of all medication errors that result in significant harm (Class 4 and 5). Mistakes typically arise from manually programming incorrect infusion parameters, and the failure to ensure the right patient receives the right medication. The most common error is manually programming infusion parameters such as delivery rate, drug, and drug dose, into the device.

Unfortunately, there is currently no commercially available device capable of reliably determining both the identity and concentration (and thus dosage) of a wide variety of unknown intravenous fluids as they are being delivered to a patient.

Although systems for verifying the presence of a drug or its concentration have been proposed, the majority of these systems rely solely on optical methods (such as optical spectroscopy). For example, U.S. Pat. No. 6,847,899 to Allgeyer et al. describes a spectroscopic analysis device for identifying medications in an IV solution. Similar systems are described in U.S. Pat. No. 7,154,102 to Poteet et al. (florescence spectroscopy), PCT/US2007/087062 and PCT/US2006/036612 by Potuluri et al. (verification of solid drug identity by optical spectroscopy) and U.S. Pat. No. 7,317,525 to Rzasa et al.

Because these systems rely on spectroscopic analysis, they typically suffer from the limitations inherent in optical systems. These limitations may include a limited ability to distinguish between compounds, and particularly mixtures of compounds having multiple components, as well as difficulty in reliably distinguishing concentrations of different compounds.

Described herein are admittance spectroscopy devices and methods that use multiple electrical admittance measurements to determine both the identity and concentration of one or more components of a medical solution such as an intravenous solution. The inventors believe that this is the first successful application of admittance spectroscopy to determine the identity and concentration of a medical fluid. Although admittance spectroscopy has been previously described in other contexts, primarily for scientific research on material characterization and particularly solid-state materials, including the characterization of dielectrics, semiconductors, electrolytes and their interfaces with metals and each other. Sensors based on admittance spectroscopy include chromatography detectors and pH sensors, enzyme-based sensors, blood-glucose sensors and urease-based sensors. However, none of these sensors are capable of determining the identity and concentration of unknown components in an aqueous solution.

The devices, systems and methods described herein may address some or all of the problems described above, and may provide systems, devices and methods for the accurate and reliable determination of one or more compounds in a solution.

SUMMARY OF THE INVENTION

Described herein are systems, devices and methods for determining the components of a fluid (or solution) using admittance spectroscopy. In particular, the devices, systems and methods described herein may be useful for determining the identity, concentration, or identity and concentration of one or more (or all) components of a fluid. The solution may be an aqueous solution (an aqueous fluid). For example, the solution may be a medical fluid such as an intravenous fluid, and epidural fluid, a parenteral fluid, or the like. Thus, the components of the fluid may be drugs. In general, the components of the fluid may be any compound, including (but not limited to): ions, molecules, macromolecules, proteins, etc.

Because of the nature of the admittance spectroscopy systems, devices and methods described herein, the identity and concentration of all of the components may be determined from the same admittance spectrographic "fingerprint." The admittance fingerprint typically includes a plurality of complex impedance measurements taken from a plurality of different electrodes exposed to the fluid, in which the surface interaction between the fluid and the various electrodes is different. The surface interaction of different electrodes (or pairs of electrodes) will be different, for example, if the surfaces are made of different materials, or have different geometries (including sizes). Surfaces may be coated, doped, or treated to create different surface interactions.

For example, described herein are methods of determining the identity and concentration of a compound or mixture of compounds in an solution that include the steps of: contacting a first surface with the solution so that a boundary layer of solution is formed on the first surface; polling the first surface to determine the surface interaction between the first surface and the compound or mixture of compounds in the solution at the boundary layer; and determining the identity and concentration of the one or more compounds based on the surface interaction.

The method may also include the step of determining the identity and concentration of the one or more compounds based on the surface interaction and the bulk properties of the solution.

In some variations, the method includes the step of contacting a second surface with the solution. The surfaces (e.g., electrode surfaces) may be immersed in the solution. For example, the step of contacting the first surface with the solution may comprise contacting the first surface in an aqueous solution. The step of contacting the first surface with the solution may comprise contacting the first surface with an intravenous drug solution, or a parenteral solution (including a parenteral drug solution, or a total parental formula, etc.), or any other medical solution.

The surface may be an electrode. For example, the first surface may comprises a non-reactive surface of an electrode. The surface may be coated, treated, roughened, or the like. Surfaces may include bound active (e.g., binding) agents (such as antibodies, charged elements, etc.).

The step of polling may include applying energy to determine the surface interactions. Admittance spectroscopy applied at appropriate energy (e.g., typically low energy) may be used to poll or test the surface interactions between the fluid and an electrode surface without disturbing the equilibrium surface interactions. The surface interactions between a particular electrode surface and a particular solution at equilibrium are characteristic of the particular electrode surface and the nature of the solution (e.g., the components in the solution and the carrier solution). If the electrode surface is a known, the (unknown) nature of the solution may be determined. For example, polling may comprise applying an electrical signal to the first surface and measuring the complex admittance. Thus, the step of polling may comprise applying a plurality of electrical signals and measuring the complex admittance at each signal. In particular, the polling step may be performed in a manner that preserves the surface interaction between the solution and the electrode surface. For example, the step of polling may comprise applying an electrical signal below the threshold for electrochemical reaction. The polling step may also be performed so that it does not disturb the dynamic equilibrium of the boundary layer on the first surface. For example, the energy applied to poll the surface interaction may be below the threshold for disrupting the surface interaction (e.g., within what is referred to as the electrode polarization effect). In some variations this is between a threshold of approximately 0.5 V and 1 V.

In the determining step, it may be useful to compare the results of the polling of surface with known surface interactions in order to identify the components of the solution. Thus, it may be useful to poll multiple different surfaces (e.g., electrode surfaces) or to include additional characteristic data, in addition to the surface interaction information determined by polling. For example, the step of determining may comprise comparing an indicator of surface interactions with a library of stored surface interactions to determine concentration and identity of the one or more compounds in the solution. The step of determining may comprises comparing an indicator of surface interactions with a library of stored surface interactions to determine concentration and identity of all of the compounds in the solution. In some variations, the step of determining comprises simultaneously determining the identity and concentration of the one or more compounds in the solution. Any of the methods described herein may also be used to determine both the identity and concentration. In some variations, the identity and concentration may be determined substantially simultaneously in the determining step.

Also described herein are methods of determining the identity, concentration, or identity and concentration of one or more compounds in an aqueous solution, the method comprising the steps of: placing a pair of electrodes in contact with the aqueous solution so that a boundary layer of aqueous solution is formed on a first surface of one of the electrodes; applying electrical excitation between the pair of electrodes to determine a complex admittance at the first surface, wherein the applied electrical excitation results in a voltage that is below the threshold level for electrochemical reactions at the first surface; and determining the identity, concentration, or identity and concentration of one or more compounds in the aqueous solution based on the complex admittance measured between the electrodes.

In some variations of the methods described herein, the method also includes the steps of recording the complex admittance at a plurality of current frequencies. A already mentioned, the pair of electrodes comprises conductive surfaces made of different materials. The method may also include the step of placing a third electrode in contact with the aqueous solution so that a boundary layer of aqueous solution is formed on a first surface of the third electrode, wherein the first surface of the third electrode is formed of a material that is different from the material forming conductive surfaces on electrodes of the pair of electrodes.

The step of applying an electrical excitation may comprise applying current at a plurality of frequencies. In some variations, the step of applying an electrical excitation comprises applying electrical energy at a level that is below the thermal fluctuation energy in the fluid. In general, the step of applying electrical excitation may comprise applying excitation a level that does not disturb the equilibrium of the boundary layer on the first surface.

Further, the step of determining may include comparing the complex admittance with a library of complex admittance to determine identity, concentration, or identity and concentration of the one or more compounds in the aqueous solution. The step of determining may include comparing the complex admittance at different frequencies with a library of complex admittances to determine identity, concentration, or identity and concentration of the one or more compounds in the aqueous solution. The step of determining may comprise comparing the complex admittance at different frequencies with a library of complex admittances to identity and concentration of the all of the compounds in the aqueous solution.

Also described herein are systems for determining the identity of a drug solution by admittance spectroscopy, the system comprising: a sensor comprising a plurality of electrodes having fluid-contacting surfaces; a signal generator configured to provide electrical stimulation at a plurality of frequencies for application from the fluid-contacting surfaces of the sensor; a processor configured to receive complex admittance data from the sensor at the plurality of frequencies and to determine the identity, concentration, or the identity and concentration of one or more compounds in the drug solution by comparing the complex admittance data to a library of predetermined complex admittance data.

In some variations, the fluid-contacting surfaces of the electrodes of the sensor are formed of a plurality of different materials, as mentioned above. The fluid-contacting surfaces of the electrodes of the sensor may be formed of a plurality of different geometries. In some variations, the sensor comprises at least three different fluid-contacting surfaces formed of different materials, different size or different materials and geometries.

The sensor may be configured as disposable (e.g., single-use) or it may be reusable (e.g., washable). A plurality of sensors may be arranged as a strip, sheet, cartridge, etc., and the system or device may be configured to engage with one or more sensors either sequentially or in parallel (e.g., allowing parallel sampling of different solutions).

The fluid-contacting surfaces of the sensor may be calibrated to a predetermined standard that matches the predetermined complex admittance data. For example, the sensors may include electrodes each having a fluid-contacting surface that is calibrated to be within some predetermined tolerances of geometry and materials forming the surface. The tolerances may be based on a standard (corresponding to the standard electrode used to determine the library information). In some variations the system may verify that the electrode surfaces are within the tolerances. For example, the system may perform an initial check using a standard solution.

In some variations, the sensor comprises at least six independent pairs of fluid-contacting surfaces.

The system may include a signal receiver configured to receive complex admittance data from the sensor and pass it on the processor. In some variations, the system includes a measurement cell configured to receive the drug solution so that the fluid-contacting surfaces of the sensor contact the drug solution. The sensor may form a part (e.g., bottom, sides, etc.) of the measurement cell.

The signal generator may be configured to apply a current frequency from about 1 Hz to about 1 MHz.

In some variations, the system includes a display configured to display the identity and concentration of the'one or more compounds within the solution. The processor may be further configured to determine the identity of the carrier diluent of the drug solution. The carrier diluents may also be displayed.

The system may also include a controller configured to coordinate application of the signal from the signal generator and to acquisition of complex admittance data from the sensor.

In general, the processor may include recognition logic configured to determine the likeliest match between the complex admittance data received from the sensor and the library of predetermined complex admittance data. The recognition logic may include an adaptive neural network trained on the library of predetermined complex admittance data. The library of predetermined complex admittance data may comprise complex admittance data measured for a plurality of individual compounds and mixtures of compounds in a carrier diluent at a plurality of frequencies.

Any of the sensors described herein may also comprises an additional sensor (or sensors), or sensor element, that is not a complex admittance electrode, and the processor may be configured to use data from the second sensor element in addition to the complex admittance data to determine both the identity and the concentration one or more compounds in the drug solution. For example, the second sensor element may be an optical sensor. In some variations, the system also includes a flow sensor, or may be configured to receive information from a flow sensor.

The processor may be configured to receive complex admittance data from the sensor at the plurality of frequencies and to simultaneously determine the identity and concentration of one or more compounds in the drug solution by comparing the complex admittance data to a library of predetermined complex admittance data.

Also described herein are systems for determining the identity, concentration or identity and concentration of an intravenous drug solution by admittance spectroscopy that include: a sensor comprising a plurality of electrodes having fluid-contacting surfaces; a signal generator configured to provide current at a plurality of frequencies for application from one or more fluid-contacting surfaces of the sensor; a signal receiver configured to receive complex admittance data from one or more fluid-contacting surfaces of the sensor; a controller configured to coordinate the application of signals from the signal generator and the acquisition of complex admittance data from the sensor to create an admittance spectrographic fingerprint of the intravenous drug solution; and a processor configured to receive the admittance spectrographic fingerprint and to determine the identity, concentration or identity and concentration of the intravenous drug solution by comparing the admittance spectrographic fingerprint to a library of admittance spectrographic data comprising complex admittance data measured from a plurality of known compounds and mixtures of compounds in a carrier solution at a plurality of frequencies and known concentrations.

Also described herein are benchtop drug solution analyzers for determining the identity, concentration or identity and concentration of a drug solution by admittance spectroscopy, the analyzer comprising: a measurement cell comprising a plurality of electrodes having fluid-contacting surfaces, the measurement cell configured to receive a sample of the drug solution; a signal generator configured to provide electrical excitation at a plurality of frequencies for application from one or more pairs of electrodes of the measurement cell; a signal receiver configured to receive complex admittance data from one or more pairs of electrodes of the measurement cell; a controller configured to coordinate the application of signals from the signal generator, and the acquisition of complex admittance data from the signal receiver, to create an admittance spectrographic fingerprint of the drug solution; and a processor configured to receive the admittance spectrographic fingerprint and to determine the identity, concentration or identity and concentration of one or more compounds in the drug solution by comparing the admittance spectrographic fingerprint to a library of admittance spectrographic data comprising complex admittance data measured from a plurality of known compounds and mixtures of compounds in a carrier solution at a plurality of frequencies and known concentrations.

In some variations the analyzer includes a housing at least partially enclosing the signal generator, single receiver and controller. The analyzer may include a plurality of single-use measurement cells. The measurement cell may comprise at least three different fluid-contacting surfaces formed of different materials, different geometries or different materials and geometries. The fluid-contacting surfaces of the measurement cell may be calibrated to a predetermined standard that matches complex admittance data of the library of admittance spectrographic data.

As mentioned above, the signal generator may be configured to apply a current frequency from about 1 Hz to about 1 MHz.

The analyzer may include a display configured to display the identity and concentration of the one or more compounds within the drug solution.

The processor be any of the processors described above. For example, the processor may be further configured to determine the identity of the carrier solution of the drug solution, and the library of predetermined complex admittance data used by the processor may include complex admittance data measured for a plurality of individual compounds and mixtures of compounds in a carrier solution at a plurality of frequencies.

The measurement cell may further comprise a second sensor element, and the processor may be configured to use data from the second sensor element in addition to the admittance spectrographic fingerprint to determine both the identity and the concentration of one or more compounds in the drug solution. The second sensor element may comprise an optical sensor.

In some variations, the processor is configured to receive the admittance spectrographic fingerprint and to simultaneously determine the identity and concentration of one or more compounds in the drug solution.

Also described herein are systems for controlling the delivery of an intravenous fluid by determining the identity, concentration or identity and concentration of one or more components of the intravenous fluid using admittance spectroscopy. The system may include: a sensor having a plurality of complex admittance electrodes configured to contact an intravenous fluid; a signal generator configured to provide electrical excitation at a plurality of frequencies for application across the plurality of complex admittance electrodes; a processor configured to receive complex admittance data from the sensor at the plurality of frequencies and to determine the identity, concentration or the identity and the concentration of one or more compounds in the intravenous fluid by comparing the complex admittance data to a library of predetermined complex admittance data; and a control output configured to regulate the operation of an intravenous drug delivery device based on the determined identity, concentration or concentration and identity of one or more compounds in the intravenous fluid.

The intravenous drug delivery device may be any appropriate drug delivery system. For example, the intravenous drug delivery device may be a pump. The pump may be a "smart pump" that includes electronic control of pump rate, and the like. The control output may be configured to modulate, adjust, turn off or suspend delivery of the intravenous drug delivery device.

The processor may be configured to receive flow information from a flow sensor in communication with the intravenous fluid and to determine a delivered dose of the one or more compounds in the intravenous fluid. In some variations, the sensor further comprises a flow sensor.

The processor may be configured to simultaneously determine the identity and the concentration of one or more compounds in the intravenous fluid.

Also described herein are methods of determining the identity and concentrations of one or more compounds in a solution by admittance spectroscopy, the method comprising: applying electrical excitation at a plurality of frequencies between at least one pair of fluid-contacting surfaces in contact with the solution; determining the complex admittance between at least one pair of fluid-contacting surfaces at the plurality of frequencies; creating an admittance spectrographic fingerprint of the solution comprising the complex admittance from the at least one pair of fluid-contacting surfaces at the plurality of frequencies; and determining both the identity and the concentration one or more compounds in the solution by comparing the admittance spectrographic fingerprint to a library of admittance spectrographic data comprising complex admittance data measured from a plurality of known compounds and mixtures of compounds in a carrier solution at a plurality of frequencies and known concentrations.

As mentioned, the solution may be an intravenous drug solution, a parenteral solution, a parenteral drug solution, or the like. The method may also include determining the identity and concentration of all of the components of the solution.

Also described herein are methods of determining the identity and concentrations of one or more compounds in a solution by admittance spectroscopy, the method comprising: applying electrical excitation at a plurality of frequencies between two or more pairs of fluid-contacting surfaces in contact with the solution, wherein at least one of the fluid contacting surfaces is formed of a different material, different size, or different material and size than the other fluid contacting surfaces; determining the complex admittance from the two or more pairs of fluid-contacting surfaces at the plurality of frequencies; creating an admittance spectrographic fingerprint of the solution comprising the complex admittance from the two or more pairs of fluid-contacting surfaces at the plurality of frequencies; and determining both the identity and the concentration one or more compounds in the solution by comparing the admittance spectrographic fingerprint to a library of admittance spectrographic data comprising complex admittance data measured from a plurality of known compounds and mixtures of compounds in a carrier solution at a plurality of frequencies and known concentrations.

Also described herein are methods of simultaneously verifying both the composition and concentration of an intravenous drug solution, the method comprising: preparing the intravenous drug solution; testing a sample of the intravenous drug solution and independently and simultaneously determining both the identity and concentration of one or more components of the intravenous drug solution.

The step of testing may include determining an admittance spectrographic fingerprint comprising a plurality of complex admittances taken at different frequencies. In some variations, the step of testing comprises determining an admittance spectrographic fingerprint comprising a plurality of complex admittances taken at different frequencies and comparing the admittance spectrographic fingerprint to a library of admittance spectrographic data comprising complex admittance data measured from a plurality of known compounds and mixtures of compounds in a carrier solution at a plurality of frequencies and known concentrations.

BRIEF DESCRIPTION OF THE DRAWINGS

FIGS. 17A and 17B illustrate schematics of two variations of a data structure representing an admittance spectrographic footprint.

FIGS. 18A and 18B are tables listing various medically relevant drugs at different concentrations.

FIGS. 20A and 20B show side-by-side comparison of the admittance spectrographic fingerprints for similar drugs Pancuronium and Vecuronium.

FIGS. 21A and 21B show side-by-side comparisons of the admittance spectrographic fingerprints for similar drugs Epinephrine and Norepinephrine.

FIGS. 22A and 22B show side-by-side comparisons of the admittance spectrographic fingerprints for Morphine and Hydromorphone.

DETAILED DESCRIPTION OF THE INVENTION

Described herein are devices, systems, and methods for determining the composition of fluids. The composition typically includes both identity and concentration, and may include the determination of all of the components of the fluid. Many of the devices, systems and methods described herein may allow for essentially simultaneous determination of the concentration and/or identity of all of the components in the fluid. In particular, the systems, methods and devices described herein are admittance spectrographic systems, methods and devices which determine the complex electrical admittance of the fluid under multiple surface conditions (either sequentially or in parallel) and/or at multiple applied frequencies in order to determine characteristic properties that may be used to determine identity and concentration. In some variations, additional measurement or sensing modalities may be used in addition to admittance spectroscopy, including optical, thermal, chemical, etc.

A fluid admittance measurement typically involves the measurement of the real and imaginary components a of the alternating current (ac) response of a fluid to applied electrical current at a particular frequency, set of frequencies or within a range of frequencies. These components are also sometimes referred to as the in-phase and quadrature or the resistive and reactive components of an ac response. This technique is herein demonstrated for the identification of fluids, components in fluids, and particularly to the identification of medical fluids, particularly fluid medications, as well as determination of their concentration and dosage.

Figure 1:
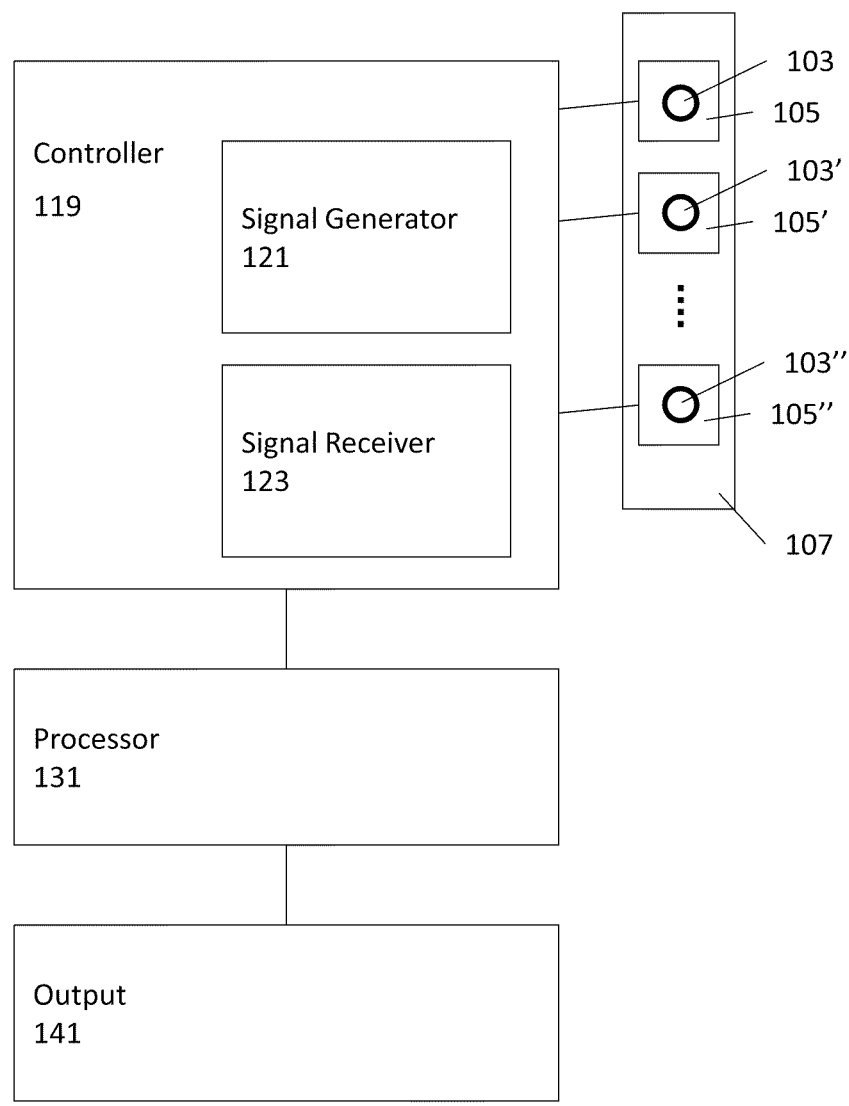
FIG. 1 is a schematic of an admittance spectrographic system for determining the composition of a fluid.

FIG. 1 shows a generic description of a system or device for determining the composition of an aqueous solution. In general, the system or device may include a plurality of electrodes (105, 105', . . . , 105"), each having a fluid-contacting region (103, 103', . . . , 103"). At least some of the electrodes may have different fluid-contacting surfaces. As described in greater detail below, the complex admittance determined across individual pairs of electrodes may depend upon the interaction of the aqueous solution and the components within the solution at the surface of the electrode (the fluid-contacting surface). Thus, the surface properties (including the size and materials forming the surface) may be controlled and matched to known or standardized fluid-contacting regions of the electrodes. Typically each electrode pair may have at least one fluid-contacting surface that is different from fluid-contacting surfaces in other pairs, in variations of the systems in which multiple electrode pairs are used. The electrodes may be formed as part of a probe 107, test cell or test chamber, tubing, or may be integrated into another device, such as a pump (e.g., IV pump), or the like.

The system or device may also include a signal generator 121 for applying an electrical signal across one or more pairs of the electrodes, and a signal receiver 131 for receiving an electrical signal representing the complex admittance. The signal receiver may include processing (amplification, filtering, or the like). The system may include a controller 119 for coordinating the application of the electrical signal to the one or more pairs of electrodes, and for receiving the complex admittance data. For example, a controller may include a trigger, clock or other timing mechanisms for coordinating the application of energy to the electrodes and receiving complex admittance data. The system or device, including a controller 119, may also include a memory for recording/storing the complex admittance data. The system or device also typically includes a processor 131 for analyzing the complex admittance data to determine the identity and concentration of the components of the aqueous solution based on the complex admittance data. Details and examples of the processor are described in greater detail below. In general, the processor may include logic (executable as hardware, software, firmware, or the like) that compares all or a subset of the received admittance data (forming an "admittance spectrographic fingerprint") to a database (e.g., library) of spectrographic data corresponding to known fluid compositions, at known components and concentrations. The processor may interpolate recognition logic configured to determine the likeliest match between the admittance spectrographic fingerprint and this known admittance spectrographic data. The processor may also use other information in conjunction with or in addition to the admittance data. For example, the system may include one or more sensors for determining other properties of the fluid, including characteristic properties that may help identify one or more components of the fluid (e.g., optical information). The processor may use this additional data to help identify the composition of the fluid. In other variations, the processor may receive information from sensors that determine fluid properties that may also be used to help characterize the administration of the fluid, or the operation of other devices associated with the fluid. For example, a flow sensor may be included as part of the system; the processor may also be configured to determine or receive flow information, and may calculate the total or instantaneous dosage of one or more components of the fluid.

Finally, a general device or system may include an output 141 for reporting, recording and/or acting on the identified composition of the aqueous solution. The output may be visual, audible, printed, digital, or any other appropriate output. In some variations described herein, the system or device may regulate or modify activity of one or more devices associated with the fluid or with a patient receiving fluid. For example, a system may turn off or limit delivery of a substance by controlling operation of a fluid pump based on the analysis of the composition of the fluid.

A system or device for determining the composition of an aqueous solution as described herein may be particularly useful for medical applications, though not strictly limited to medical applications. Thus, in many of the examples and variations described herein the devices and systems are for analyzing, monitoring or testing medical fluids such as solutions of drugs or therapeutic materials, including IV fluids, parenteral fluids, and the like. Both in-line (e.g., in-line IV fluid monitoring) and benchtop systems are described. Integrated systems, in which the devices/systems for determining composition of the aqueous solutions are connected or integral to other devices or systems, including tubing, pumps, syringes, and the like, are also contemplated and described.

In many of the admittance spectroscopy systems and devices described herein, multiple polarizable electrodes consisting of electrode pairs of identical and different materials are utilized. As mentioned, in some variations, multiple electrode admittance spectroscopy is used and either applied alone or in conjunction with other identification/characterization sensors and methods, including optical sensors. Examples of electrodes either alone or with additional sensors in variations configurations of probes and measurement cells including electrodes (and particularly electrodes having fluid-contacting regions) are described in greater detail below.

Examples of various systems are also described. Although many of these systems may include just admittance spectroscopy, the examples described herein often include additional sensors. For example, a system incorporating automated computer control for measurement of fluid admittance over a range of frequencies and using a set of multiple different electrodes has been developed. This system includes a sensor element consisting of a set of electrodes coupled to a measurement system and computer for data acquisition and system control. It also includes 4 optical sources and detectors at specific wavelengths. It is to be understood that these systems do not require the use of the additional (e.g., optical) sensing modality, and may be constructed and used with just the admittance spectroscopy features.

Admittance Spectroscopy

PCT patent application PCT/US2009/001494 incorporated by reference above describes the application of multiple parameters (including multiple sensors) that each provide different characteristics which may be combined to create a multiparametric fingerprint of a solution such as an intravenous solution. This multiparametric technique (and embodiments thereof) may be used in a hospital setting to verify the identity and dosage of one or more IV fluids to be applied to a patient. Described herein are systems and devices that may also be considered multiparametric, in which the "fingerprint" that is taken from the solution in order to determine the composition of the solution includes admittance spectroscopy information taken from the solution.

Thus, in the context of the present disclosure, a multiparametric fingerprint of a solution will include a plurality of admittance spectrographic data. The "fingerprint" may therefore be referred to as an admittance spectrographic fingerprint, although additional identifying information may be included, as described in greater detail below (such as optical, thermal, etc.). the fingerprint may be collected or compiled as a matrix or array of values, and it may be plotted, graphed, mapped, or the like. In some variations, the fingerprint may include time-varying data, and may be indexed by a temporal and/or spatial element (e.g., at points taken over time, or taken after some triggering event). The parameter values forming the multiparametric fingerprint may be indexed by the sensor (e.g., electrodes) that acquired them. The fingerprint may include at least two dimensions (such as real and complex impedance) and may include many more than two dimensions (e.g., real and complex impedance at a plurality of frequencies, or real and complex impedances for multiple electrode pairs having different surface interactions with the fluid at different frequencies). The parameter values within the fingerprint (e.g., the complex impedance values) may be averages, medians, or means. In some variations the values forming the fingerprint may be filtered. In some variations the values forming the fingerprints are normalized. In some variations, the information forming the fingerprint is derived from combined (e.g., subtracted, added, scaled, etc.) data.

The admittance spectrographic fingerprint described herein may be compared, as described herein, in order to determine the composition of the fluid, which may include simultaneously determining the identity and concentration of all components in the solution, including the identity of the carrier solution. Thus, in some variations, the acquired (unknown) fingerprint may be compared against known fingerprints that may be included in a library of fingerprints provided for known solution compositions.

The admittance spectroscopy systems described identifies components of a solution, and particularly drugs in a carrier solution, based on the application of multiple, different sensing elements or sensors. As will be described in greater detail below, the sensors used may be electrodes each having at least one fluid-contacting surface.

The electrodes used to measure complex admittance described herein are typically made of metals that are non-reactive with the components of the fluids that they contact, and generally, ions of the utilized metals are not present in the intravenous fluids. This will allow the determination of the characteristic steady-state complex impedance. However, it has long been known that such electrodes, when exposed to an aqueous solution such as an IV drug solution, exhibit so-called "blocking" behavior: a DC voltage applied to such metal electrode results in zero net charge transfer through metal-electrolyte interface unless the voltage exceeds certain level. This effect is called electrode polarization and has been studied since 1879 (see, e.g., Helmholtz H. Studien über electrische Grenzschichten. Annalen der Physik and Chemie. 1879; 243(7):337-382, or the translated version: "Studies of electric boundary layers". translated by P. E. Bocque, Bull. Dep. Engineering Research Univ. Mich. 33, 5-47 (1951)).

Figure 4:
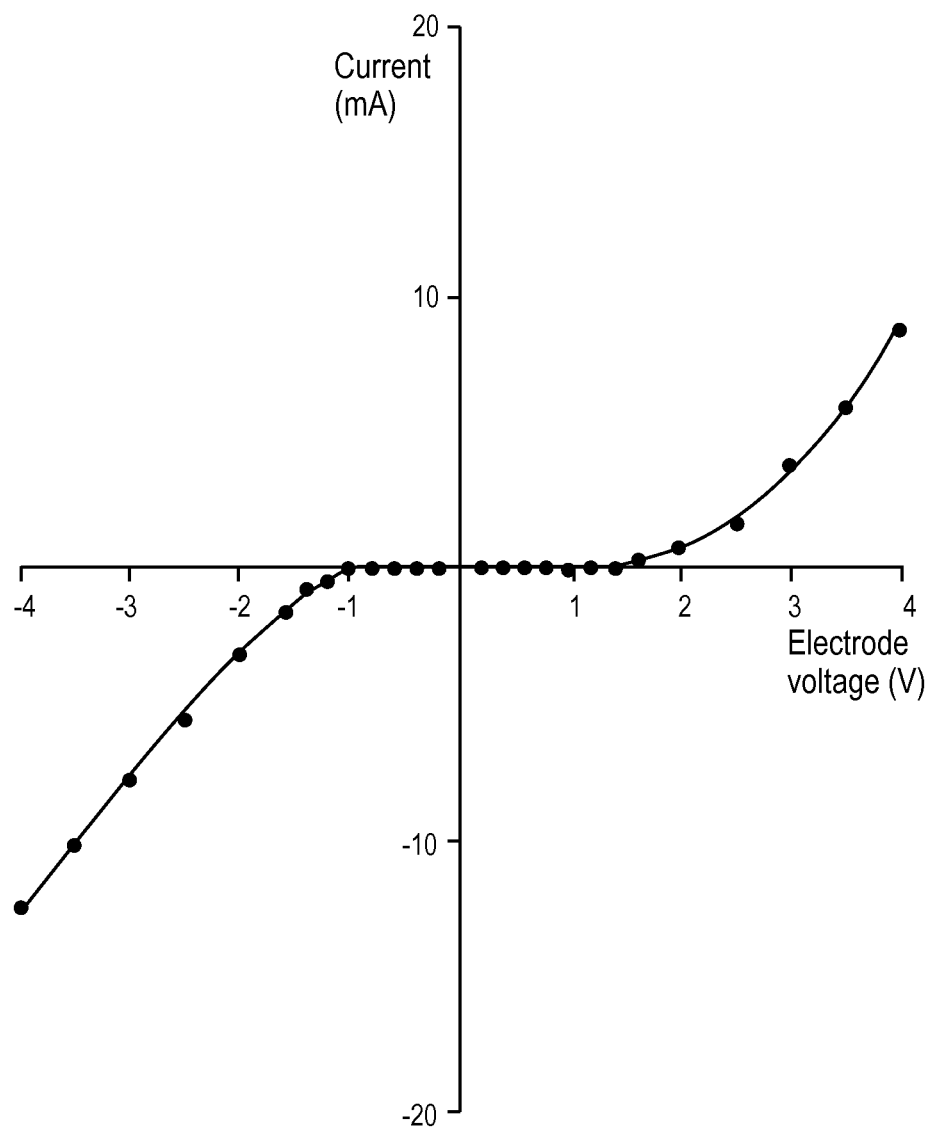
FIG. 4 is a graph showing the electrode polarization effect (adapted from Walton C, Gergely S, Economides A P. Platinum pacemaker electrodes: origins and effects of the electrode-tissue interface impedance. Pacing Clin. Electrophysiol. 1987; 10:87-99).

Electrode polarization is particularly well-researched and documented in the field of implantable electrodes for pacemakers, where the presence of this effect impedes efficient cardiac activity sensing and stimulation. For example, when a platinum pacemaker electrode is immersed in a bath of physiological saline and a DC voltage is applied to it within a range of potentials, virtually no current flows through the electrolyte unless the voltage exceeds values of approximately ±1 V. Below this voltage the electrodes demonstrate capacitive behavior. This effect is illustrated in FIG. 4. To achieve successful pacing with the limited available electrode area, pacemakers typically rely on chemical reactions at the electrode interface to pass sufficient charge to the tissue, and overcome this electrode polarization effect. See, e.g., Walton C, Gergely S, Economides A P. Platinum pacemaker electrodes: origins and effects of the electrode-tissue interface impedance. Pacing Clin. Electrophysiol. 1987; 10:87-99).

The complex admittance measured from a particular fluid-contacting surface reflects the interaction of the solution and any compounds in the solution (including ions, drugs, and the like) and the surface of the fluid-contacting surface. The interaction between the fluid-contacting surface and the fluid (at the interface) may be established shortly (if not virtually immediately) upon contacting the fluid to the surface. The surface may be probed (by the application of electrical energy) to determine the complex impedance, and the complex impedance is characteristic of the interaction between the fluid and the fluid-contacting surface of the electrode. Thus, the complex impedance determined at a particular surface reflects the nature of the interaction between the fluid-contacting surface and the solution, and may therefore depend on the material forming the fluid-contacting surface and the geometry of the fluid contacting surface (e.g., the surface area). Different surfaces may produce different complex impedances in the same solution, because the interactions with the fluid may differ between different fluid-contacting surfaces (including the sizes, and the materials forming the fluid-contacting surfaces). As used herein the term fluid-contacting surface typically refers to the conductive (non-insulated) region of an electrode that contacts the fluid. The fluid contacting surface may include a coating or the like, and may be surrounded by an insulating region. For example, the complex impedance of a silver-silver electrode pair may be very different than the complex impedance of a silver-gold electrode pair with the same geometry measured in the same solution at the same frequency and current level.

Because the complex admittance is so variable and sensitive to the composition (and geometry) of the fluid-contacting surface of the electrodes, particularly when probed at low power levels (e.g., current and/or voltage levels), complex impedance has not previously been successfully used as a method for determining the composition of an unknown aqueous solution, and particularly not a medical solution.

Admittance spectroscopy may also be referred to as immittance spectroscopy (impedance or admittance), and encompasses a variety of techniques for the measurement and analysis of the complex impedance (Z), the complex admittance (Y), and the complex dielectric constant ($\in$) as a function of frequency. These values may be plotted in the complex plane. The complex plane is typically defined as standard orthogonal xy frame of reference in which the complex impedance (Z=Z'+iZ"), admittance (Y=Y'+iY"), and/or dielectric constant ($\in=\in'+i\in''$) is plotted so that x=Z', y=Z"; x=Y', y=Y"; x=$\in'$, y=$\in''$, where ' and " are real and quadrature components of the complex value.

Figure 2:
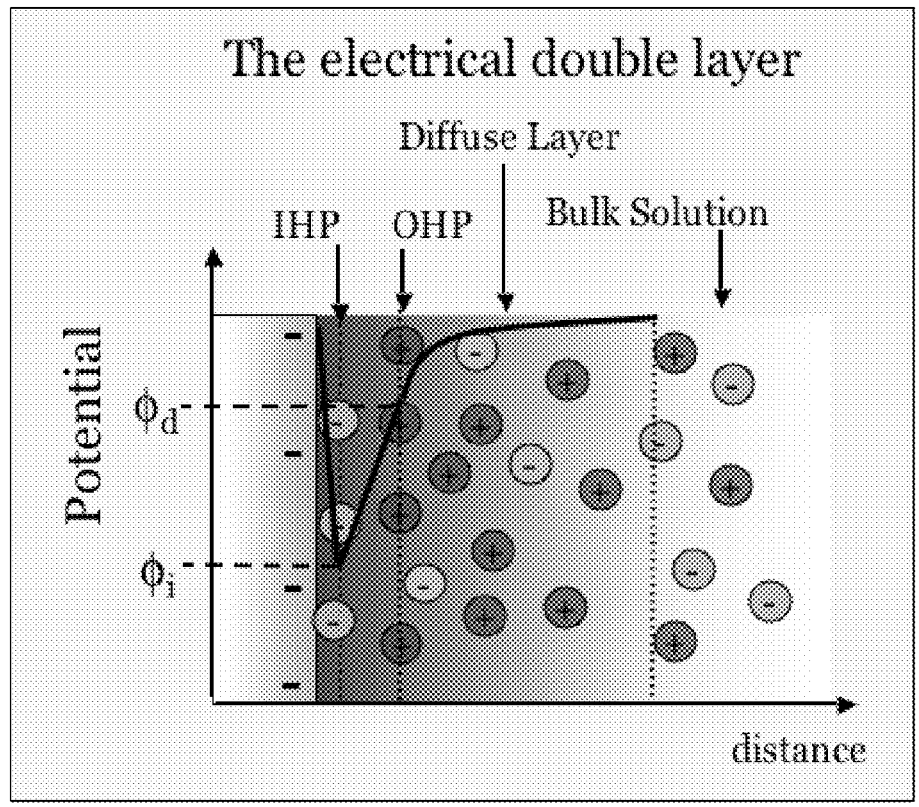
FIG. 2 illustrates the formation of an electrical double layer on fluid-contacting surface of an electrode, illustrating the dynamic equilibrium of the solution components on the surface.

When a solution first contacts a surface such as an electrode surface, the surface interaction between the electrode and the fluid results in the formation of a layered boundary as illustrated in FIG. 2. This layered boundary may be characteristic of the electrode surface and the solution, and may be dependent upon the composition of the solution as well as the composition and/or structure of the surface. In general, multiple "layers" are formed between the surface and the solution forming an interface of sorts. For example, in FIG. 2, three different regions may be formed between the surface of the electrode and the bulk of the fluid: the IHP (inner Helmholtz plane) is closest to the surface, the OHP (outer Helmholtz plane) is the next layer, followed by a diffuse layer that gradually transitions to the bulk solution.

In many of the variations described herein, the electrodes are fully polarizable electrodes, in which no charge transfer is possible at low potentials (voltages), e.g., below some $\Phi_i$, which is typically at least 500 mV, and thus electro-chemical reactions will not take place at the electrode surface. If the excitation voltage $\Delta V$ does not disturb the system much more that naturally occurring thermal fluctuations, then the response to the applied current is linear, so that: $\Delta V \sim kT/e$, where k is Boltzmann's constant, T is absolute temperature and e is the electron charge. $\Delta V$ is approximately 25 mV at room temperature.

Figure 3:
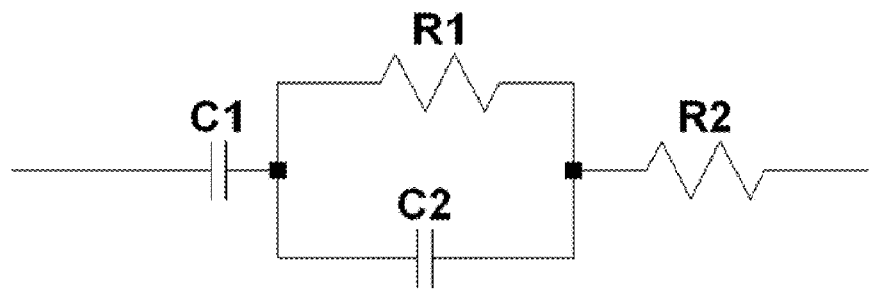
FIG. 3 is the equivalent circuit for the electrode-solution interface shown in FIG. 2.

Thus, at the surface of an electrode, the complex AC impedance $Z(\omega)$ or admittance $Y(\omega)$ can be approximated as an equivalent circuit shown in FIG. 3, and can be measured. The relationship for impedance can be expressed as:

$$Z(\omega) = Z'(\omega) + iZ''(\omega) =$$
$$= \left(R_2 + \frac{R_1}{1+(\omega C_2 R_1)^2}\right) - i\left(\frac{1}{\omega C_1} + \frac{\omega C_2 R_1^2}{1+(\omega C_2 R_1)^2}\right)$$

The equivalent circuit resulting from this model of the metal-electrolyte interface contains 4 independent parameters ($R_1, R_2, C_1, C_2$) that are affected by the presence of any compounds in the solution, for example, drug molecules or ions in a carrier electrolyte. The individual components of the equivalent circuit are not directly accessible in practice, but can be measured indirectly through measurements of the cell's time-dependent response to excitation current or voltage or through AC impedance or admittance. It may be more straightforward to measure AC current rather than impedance and work with admittance, although it leads to bulkier formulae, for example:

$$Y(\omega) = \frac{(\omega C_1)^2(R_1 + R_2(1+(\omega C_2 R_1)^2))}{(\omega C_2 R_1 + \omega C_1(R_1+R_2))^2 + (\omega C_1 \omega C_2 R_1 R_2 - 1)^2} +$$
$$i \frac{\omega C_1(1 + \omega C_1 \omega C_2 R_1^2 + (\omega C_2 R_1)^2)}{(\omega C_2 R_1 + \omega C_1(R_1+R_2))^2 + (\omega C_1 \omega C_2 R_1 R_2 - 1)^2}$$

The values of the 4 independent parameters can be calculated from two measurements of impedance or admittance at two different frequencies $\omega_1$ and $\omega_2$. If complex impedance is measured: $Z_1 = Z(\omega_1) = a_1 + ib_1$ and $Z_2 = a_2 + ib_2$ the equivalent circuit parameters are calculated as follows:

$$C_1 = \frac{(\omega_1 b_1 - \omega_2 b_2)(\omega_1^2 - \omega_2^2)}{\omega_1 \omega_2 (\omega_1 \omega_2 ((a_1-a_2)^2 + b_1^2 + b_2^2) - b_1 b_2(\omega_1^2 + \omega_2^2))}$$

$$R_1 = -\frac{(a_1-a_2)^2(\omega_1 b_1 - \omega_2 b_2)^2}{(a_1-a_2)(\omega_1 b_1 - \omega_2 b_2)^2(\omega_1^2 - \omega_2^2)}$$

$$C_2 = \frac{(a_1-a_2)^2(\omega_1 b_1 - \omega_2 b_2)(\omega_1^2 - \omega_2^2)}{\left(\begin{array}{c}\omega_1^2(a_1-a_2)^2 + \\ (\omega_1 b_1 + \omega_2 b_2)^2\end{array}\right)\left(\begin{array}{c}\omega_1^2 b_1^2 - 2\omega_1 \omega_2 b_1 b_2 + \\ \omega_2^2(a_1-a_2)^2\end{array}\right)}$$

-continued $$R_2 = \frac{\omega_1^2(a_1^2+b_1^2) - 2\omega_1\omega_2 b_1 b_2 + \omega_2^2(a_2^2+b_2^2) - a_1 a_2(\omega_1^2+\omega_2^2)}{(a_1-a_2)(\omega_1^2-\omega_2^2)}$$

These four independent parameters may be used to determine the complex impedance, and for angle calculations and clustering for drug recognition as described below. Multiple measurements at one or each frequency can be made to average signal and improve signal to noise ratio (SNR). More than 2 measurements at 2 different frequencies can be used to calculate the above four parameters. Multiple frequency measurements may provide the redundancy in data that can be utilized to improve SNR though known algorithms such as least squares method. Although the measurements described above reference frequency domain measurements, the equivalent information can be obtained from time domain measurements.

However, when determining the complex admittance of a medical solution such as an IV solution, it is desirable to use an excitation energy as low as possible, to prevent electrochemical reactions at the surface of the electrode which may both prevent a stable determination the complex admittance, and may undesirably modify or effect the solution being tested. Thus, in the variations described herein, the excitation energy applied between the sensor electrodes is typically kept below the threshold voltage of any electrochemical reactions that may occur in the intravenous fluid. Preferably, the excitation energy applied between the sensor electrodes is kept below the characteristic value of the energy associated with the naturally occurring thermal fluctuations.

Thus, sensors described herein typically operates at voltage significantly lower than the threshold necessary to avoid the electrode polarization effect, in order to avoid triggering electrochemical reactions at the electrode-fluid interface. The threshold is typically between about 0.5V and about 1 V (e.g., 0.5V, 0.6V, 0.7V, 0.8V, 0.9V, 1.0V). Based on our preliminary work, we have determined that, the typically undesirable electrode polarization effect may in fact provide useful information and important information regarding the nature and condition of the electrode-fluid interface. For the response to be described in terms of the cell AC admittance, all of the measurements should be performed within the voltage range where current is proportional to voltage-linear regime. This regime is well covered in pacemaker-related studies, where the electrode polarization effect is considered problematic. Electrode polarization is considered a major source of effort in determining the impedance of biological samples in solution (see, e.g., Oh et al., "Minimization of electrode polarization effect by nanogap electrodes for biosensor applications" Porc. MEMS-03 Kyoto Micro electro mechanical Systems IEEE The Sixteenth Annual International Conference on, pages 52-55, Jan. 19-23, 2003).

The application of energy above the approximately threshold in order to overcome the polarization effect (e.g., above 1 V) typically results in an external electric field strong enough to disturb the natural arrangement of fluid components within the double layer adjacent to the electrode surface and may result in electrochemical reactions. The structure of the fluid layers adjacent to the electrode interface is not static, but rather exists in dynamic equilibrium under naturally occurring thermal fluctuation. The fluctuating energy associated with thermal motion of an ionic media can be estimated as kT/e, where k is Boltzmann's constant, T is absolute temperature in K° and e is electron charge, which at room temperature is about 25 mV.

The complex admittance sensors described herein typically operate at excitation voltage of approximately 30 mV amplitude (~21.2 mV RMS), which is of the same magnitude as the voltage associated with natural thermal fluctuation. This operation regime ensures that sensor measures response of the fluid cell without considerable disturbance of the electrode/fluid interface, and allows the unexpected advantages of operating within the regime of electrode polarization which was previously avoided.

By exploiting the usually undesirable electrode polarization effect, the devices and systems described herein may probe the dynamic equilibrium formed at the interface of the electrode and the fluid being tested without disturbing this naturally occurring fluid stratification. Since the equilibrium is rapidly formed, and is characteristic of the fluid, this information may provide information about the interface between the known surface of the electrode and the unknown fluid being tested. In operation, the devices and systems may therefore use multiple, different electrodes (e.g., electrodes having different surface interactions with the solution being tested). These electrodes used to generate the admittance spectra are typically polarizable, and the system is operated below the thermal energy of the sample. This may allow for multiple, highly reproducible measurements to provide signatures based on the complex admittance that depend on the composition and concentration of components in the solution.

Benchtop System or Device

Some variations of the devices and systems described herein are configured to be used to test solutions that are not typically flowing. For example, a system may be configured to test pre-prepared mixtures of aqueous solutions such as IV drug solutions that are prepared in a pharmacy or commercially. These systems may therefore be referred to as a benchtop device or system. For example, a benchtop system may be used to by pharmacists or pharmacies to validate prepared doses of medical solutions. Any error in a prepared medication can have very serious consequences if the erroneously prepared medication is administered to a patient.

Benchtop device typically includes a measurement cell or chamber into which a sample of the solution to be tested is applied. For example, in some variations the system will have a sensor chamber that could be in the form of an optical cell in which the sensor element is molded or inserted. A drug to be tested is introduced into the cell and its electrical (and in some variations also optical properties) may be measured to generate a set of 3 or more independent measurement values. These values in aggregate will create a means of identifying a particular drug from another, which may be the admittance spectrographic fingerprint of the sample. The values of each of the multiple data channels, when combined, can produce a unique pattern for each compound it measures and thus provide a means of identifying fluid compounds such as drugs.

In one example of a benchtop system described herein, the system (or device) includes a measurement sensor that is part of a measurement cell, and that is utilized in conjunction with a lock-in amplifier that supplies excitation signals and detects the resulting signals reflecting the complex admittance at different frequencies. A controller (e.g., a computer system, dedicated processor, or the like) may control the signals and acquire the data.

Figure 5:
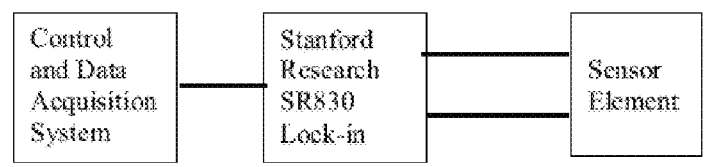
FIG. 5 schematically illustrates one variation of an admittance spectrographic system for determining the composition of a fluid.

For example, FIG. 5 shows a diagram of one variation of a benchtop system. In this example, the system includes a sensor element (typically having multiple electrodes), a lock-in amplifier for application and receiving signals to/from the electrodes, and a control and data acquisition system to control the application of energy and the recording of complex admittance.

This benchtop system implements multiple electrode fluid admittance measurements. In some variations, the system may also implement additional (non-admittance) sensors. For example, optical sensors (e.g., measuring multiple wavelength refractive index and absorption measurements); as discussed in greater detail below.

Figure 6:
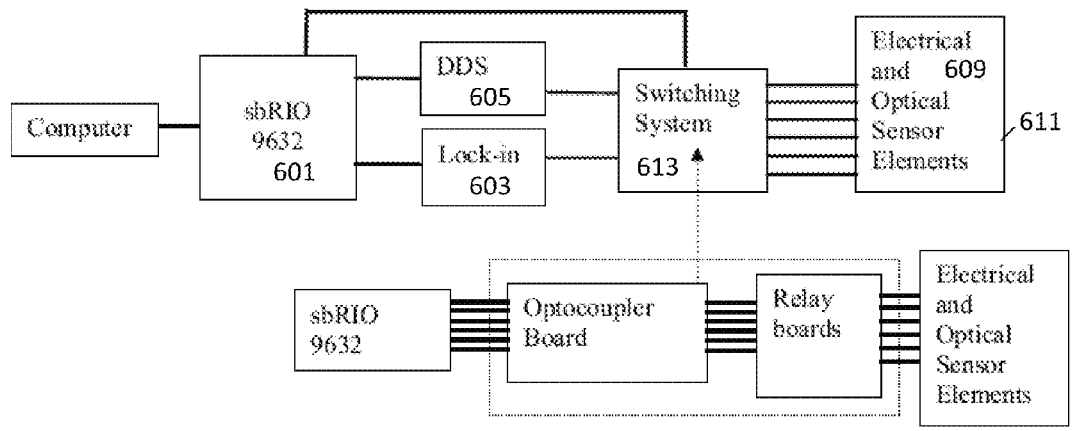
FIG. 6 schematically illustrates another variation of an admittance spectrographic system for determining the composition of a fluid.

FIG. 6 shows a slightly more detailed schematic of a benchtop system, configured to measure both complex admittance and optical sensor elements. This system includes a control and acquisition sub-system 601 (e.g., National Instruments sbRIO 9632) that may include analog to digital and digital to analog circuitry for generating and detecting signals, as well as a field programmable gate array (FPGA) and on board microprocessor with an embedded real-time operating system. This may also provide over 100 digital lines, some of which may be used for control and switching applications in the device.

Figure 7A:
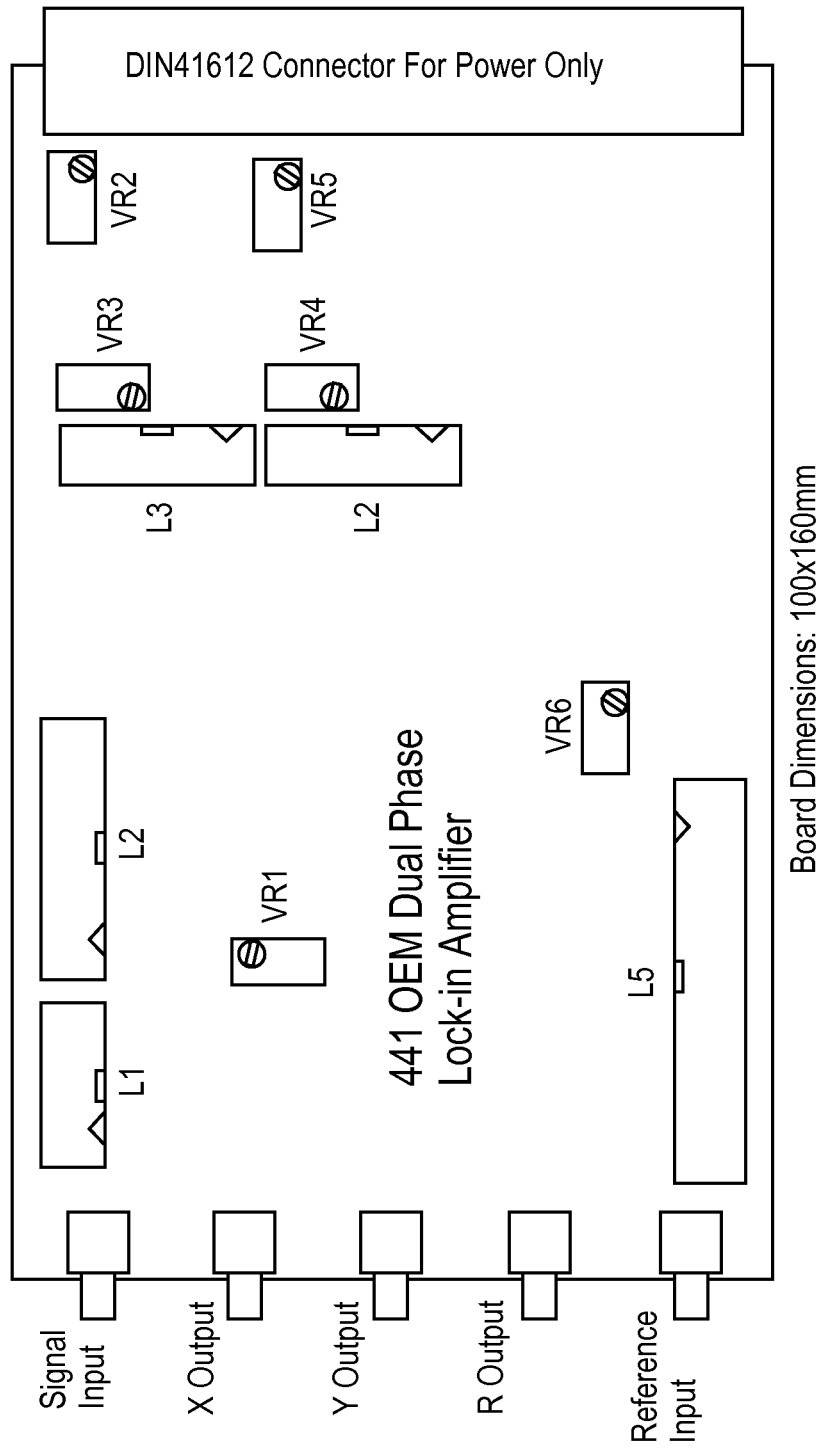
FIG. 7A is a schematic of a modified Scitec Instruments model 441 board level lock-in amplifier.

In this example, a modified Scitec Instruments model 441 board level lock-in amplifier 603 (a schematic of which is shown in FIG. 7A) is used for signal detection. A programmable excitation signal source 605 was built by modifying an AD9951 DDS VFO board kit obtained from Hagerty Radio. The system also includes a sensor element 609 which is part of a measurement cell 611, utilized in conjunction with a switching system 613 to enable automated measurement of the signal from all combinations of the 6 elements on the sensor chip and all 4 optical measurement channels. This switching sub-system 613 may be computer controlled.

Figure 7B:
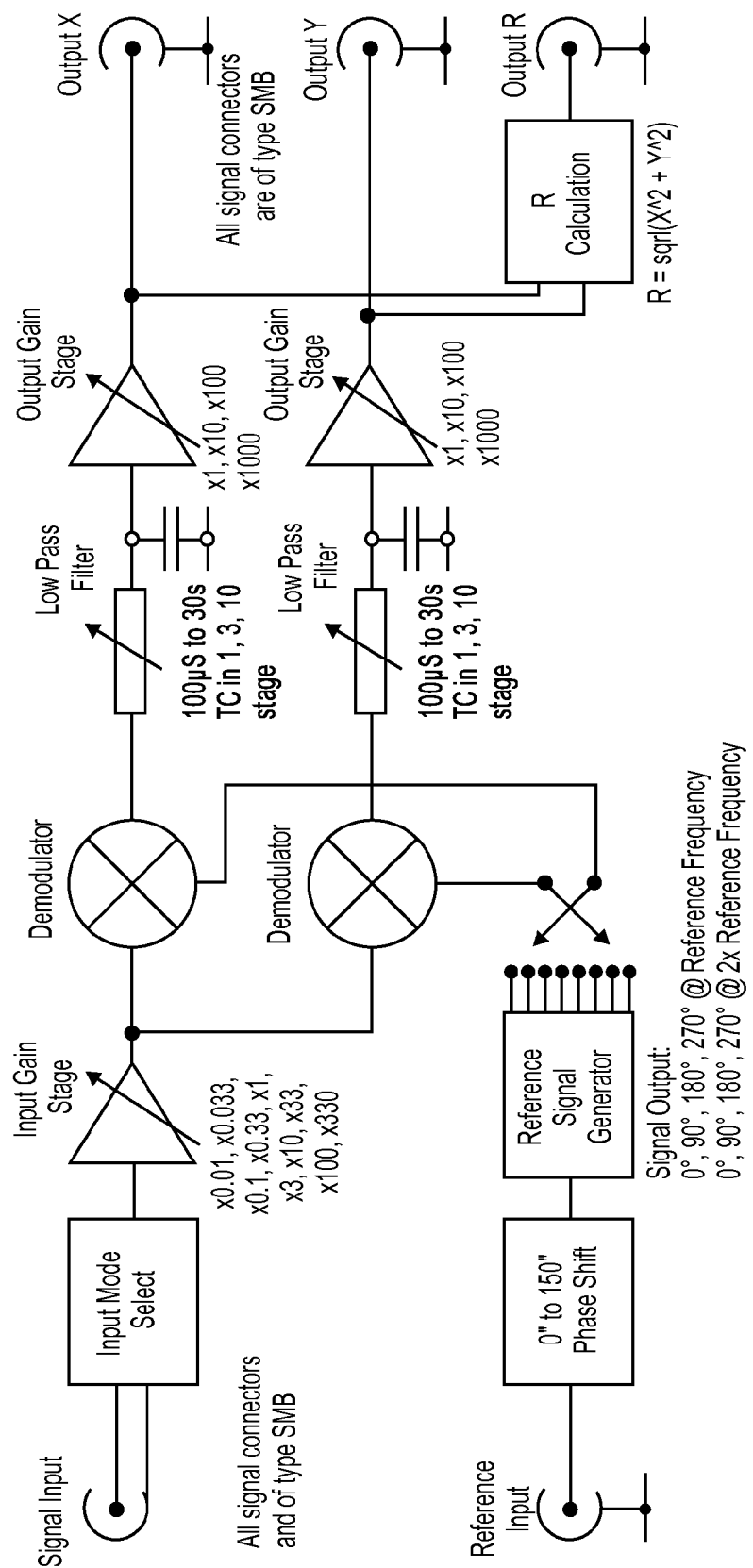
FIG. 7B shows a block diagram for a Scitec #441 Lock-in amplifer.

The exemplary prototype shown in FIG. 6 allows testing and switching of multiple admittance electrodes and optical sensor channels. This switching allows the system to take a plurality of complex admittance measurements (often simultaneously), and to store this data along with the additional (optional) optical data and construct an admittance spectroscopy fingerprint that is characteristic of the composition of the fluid. Although any appropriate synchronous detector or other lock-in amplifier may be used, FIGS. 7A and 7B illustrate board layout and block diagrams for the Scitec #441 Lock-in amplifier example described above.

Figure 8:
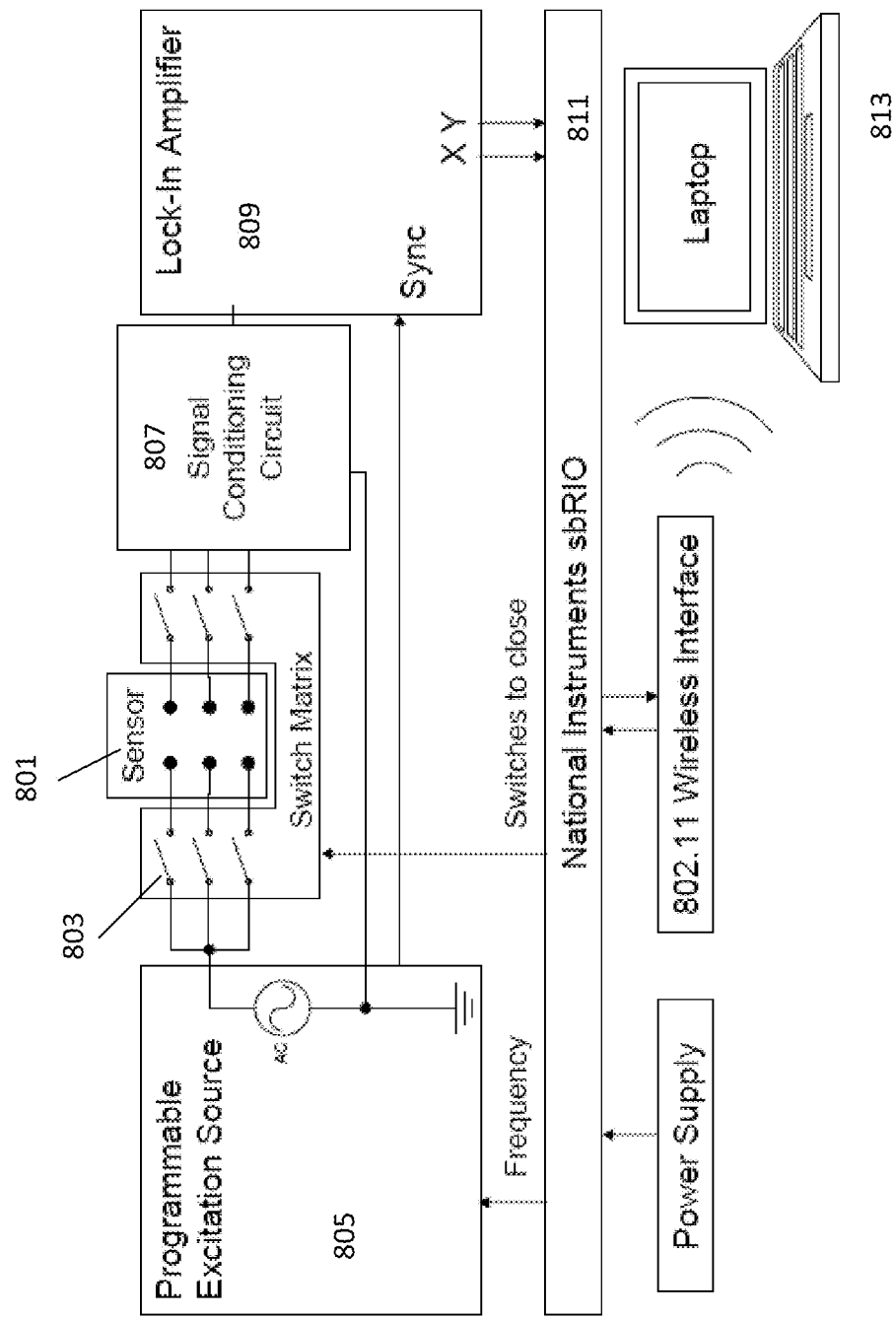
FIG. 8 schematically illustrates another variatoin of an admittance spectrographic system for determining the composition of a fluid.

Another example of a benchtop variation of the devices and systems for determining the composition of a fluid is shown in FIG. 8. In this example, a sensor 801 may be part of a measurement cell (not shown), and it may be a reusable sensor or a disposable/single use sensor. The sensor may be embedded (or may form part of) the measurement cell, or it may be inserted into the measurement cell. In this example the sensor 801 includes six electrodes which may form up to 15 different channels for independently sampling complex admittance, if each electrode has a distinct surface interaction with the sample fluid. In FIG. 8, three different electrodes are used (e.g., Au, Au, Pd, Pd, Ti, Ti) forming six unique electrode pairs (Au—Au, Au—Pd, Au—Ti, Pd—Pd, Pd—Ti, Ti—Ti), and a switch matrix 803 is used to control which electrodes are active for probing by applying energy and determining the resulting complex admittance. A programmable (and controllable) excitation source 805 drives excitation of the electrode pairs, and a signal receiving sub-system, including signal conditioning circuit 807 is used as well. The signal conditioning circuit 807 may be used to smooth, filter, amplify, or otherwise modify the signal. The receiving sub-system may also include a lock-in amplifier 809. A controller 811 may control the excitation and data collection, including regulating, synchronizing, and/or triggering the system and may also collect, pass on, and/or store the data.

The system in FIG. 8 includes a wireless output that may communicate with one or more computers 813 or other targets. However, any approriate target may be used. In addition, the processor that is configured to analyze the received admittance spectroscopic information may be a dedicated processor, or it may include software, hardware and/or firmware running on a dedicated or general-purpose computer. In some variations the processor is directly coupled to the rest of the system. In FIG. 8, the processor may be integrated into the controller 811, or it may be part of the computer 813 to which the system wirelessly communicates.

The benchtop device may be a compact and/or portable device. For example, in some variations the general, the benchtop device is configured for use in a pharmacy, and may be used to independently determine the identity and concentration of one or more drugs in a prepared IV solution. A sample of the solution may be loaded into the measurement chamber (e.g., less than 100 microliters may be aliquoted into the measurement cell). The device then rapidly analyzes the sample, and provides an output of the results.

Figure 9:
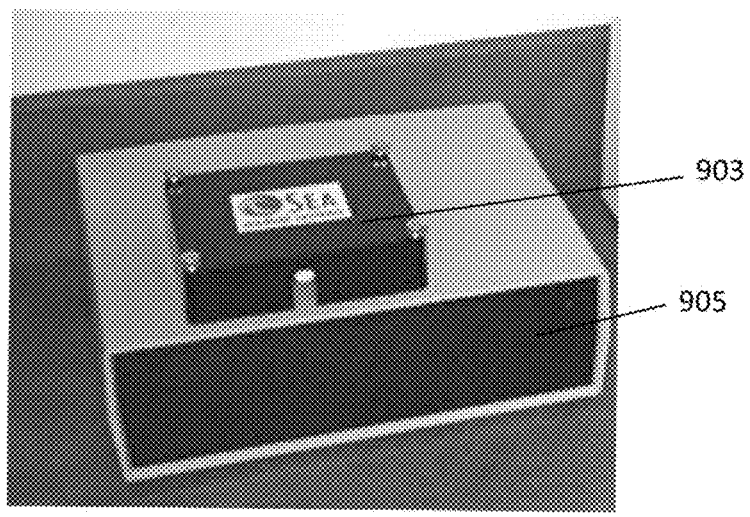
FIG. 9 shows a prototype benchtop admittance spectrographic device for determining the composition of a fluid.

FIG. 9 shows a prototype of a benchtop system, including a test cell region 903, into which a sample of fluid may be loaded. A sensor was formed by lithographic techniques, as described below, forming six unique pairs of electrodes: Au—Au, Au—Pd, Au—Ti, Pd—Pd, Pd—Ti, and Ti—Ti. In practice, any of these electrodes or pairs of these electrodes can be used for either excitation and/or reception (e.g., excitation pair: Au—Pd, reception: Ti, or excitation: Au, reception: Pd—Ti, etc).

In FIG. 9, the device also includes a controller housing 905, which may contain the signal generator/excitation source, and signal receiver elements for detecting the complex admittance. A processor for analyzing the admittance fingerprint may also be included within the housing. In this example, the benchtop device is approximately the size of a notebook computer, and uses disposable sample holders with smart sensor chip (including all of the electrodes). The device requires only small (<100 μl) samples, typically sufficient to wet the sensors, or immerse them. The device determines drug identity and concentration instantaneously, and reports the results. The user is not required to input any information about the sample, however in some variations the user may indicate the intended identity and concentration of the solution. In this case, the device may indicate that the sample matches or does not match the expected mixture.

In some variations, the device or system may indicate if the solution tested appears to have an error in concentration or composition, for example if the concentrations of certain components are above those typically considered safe. Thus, the device (e.g., the processor) may include information about the safe concentration ranges of known compounds, as well as information about common mixtures of compounds. If the devices or systems do not recognize the fingerprint of the tested solution, then the device may also indicate this. This may occur if the fingerprint does not match the library of known fingerprints available to the processor within a reasonable statistical range. In some variations the system may provide the "closest match" and indicate a confidence level (e.g., the statistical probability of the match, or it may only indicate a match when the likelihood is above some threshold level.

As mentioned, the benchtop configuration described above may be particularly useful in pharmacy setting in which medical solutions (e.g., intravenous solutions, parenteral solutions, or the like) may be tested after formulation and before administration to a patient. These systems may be integrated into existing systems for monitoring and managing patient safety as a confirmation of the identity and concentration of the fluid. For example, in some variations the systems described herein may generate a label indicating the detected/confirmed identity of the solution. The system may also generate a log or record of solutions examined.

In-Line System or Device

Figure 10:
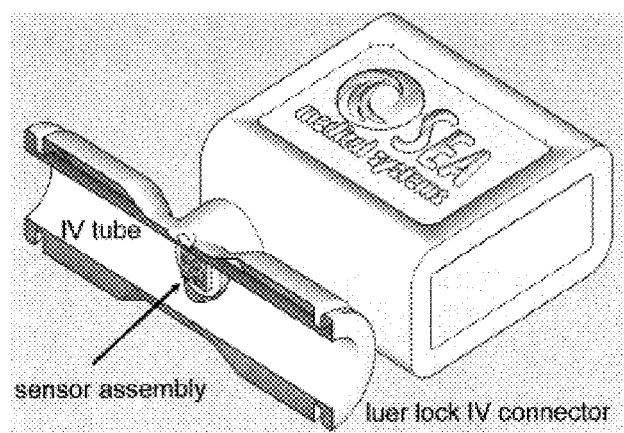
FIG. 10 illustrates one variation of an in-line admittance spectrographic device for determining the composition of a fluid that is configured to be attached in-line with an IV fluid source.

FIG. 10 shows one embodiment of an in-line sensor configured to be attached in-line with an IV fluid source. In this example, the sensor simultaneously (or essentially simultaneously) measures multiple parameters, including multiple complex admittances using multiple sensors. The sensor assembly is coupled directly in communication with the IV solution being delivered to a patient. For example, the sensor may be integrated or inserted in-line with an IV tube, an IV pump, or the like. The sensor assembly is generally coupled to a processor that can check the admittance spectroscopy fingerprint against a library of known admittance spectroscopy profiles. The system can then determine the identity or composition of the fluid, and report the drug identity and dosage, triggering an alert or an action (e.g., stopping, suspending or reducing drug delivery) if the IV solution exceeds a predetermined level of a particular drug, or is missing a drug. In some variations the system is programmed to have an expected solution composition for a particular individual. The system may also generally determine if one or more components of the IV solution is outside of normal ranges.

For example, the system may be configured to monitor in particular the levels (or doses) of certain high alert medications, and provide alerts if these medications are above a threshold (or are present in any amount). High alert medications may include: heparin, insulin, neuromuscular blocking agents, cytotoxic chemotherapy agents, sodium chloride (>0.9%), potassium (chloride, acetate, phosphate, >0.4 mEq/mL), Magnesium sulfate (>100 mL), Alteplase (t-PA, Activase), Tenecteplase (TNKase), Vinca alkaloids (VinCRIStine, VinBLAStine, Vinorelbine), narcotic/opioids (e.g., PCA), epinephrine, norepinephrine, isoproterenol, etc.

In some variations the sensor component is disposable while the processor portion is re-usable. In some variations, both the processor and the sensor components are disposable or both are reusable.

Figure 11:
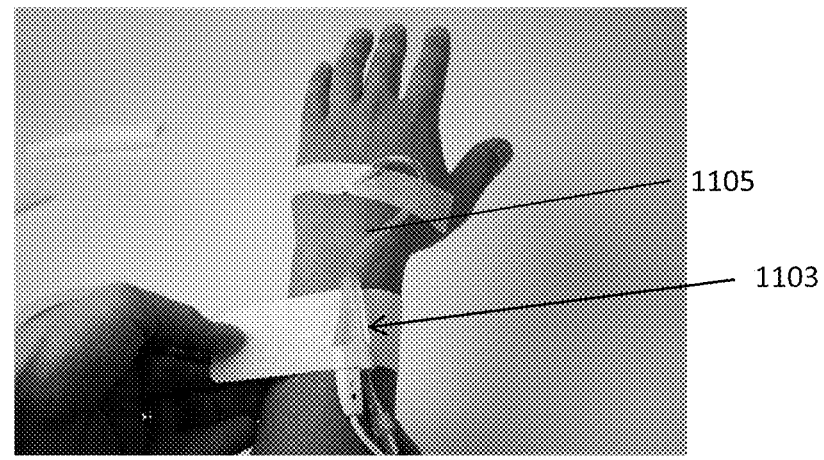
FIG. 11 shows another variation of an in-line admittance spectrographic device for determining the composition of a fluid that is attached in-line with an IV fluid source.
Figure 12:
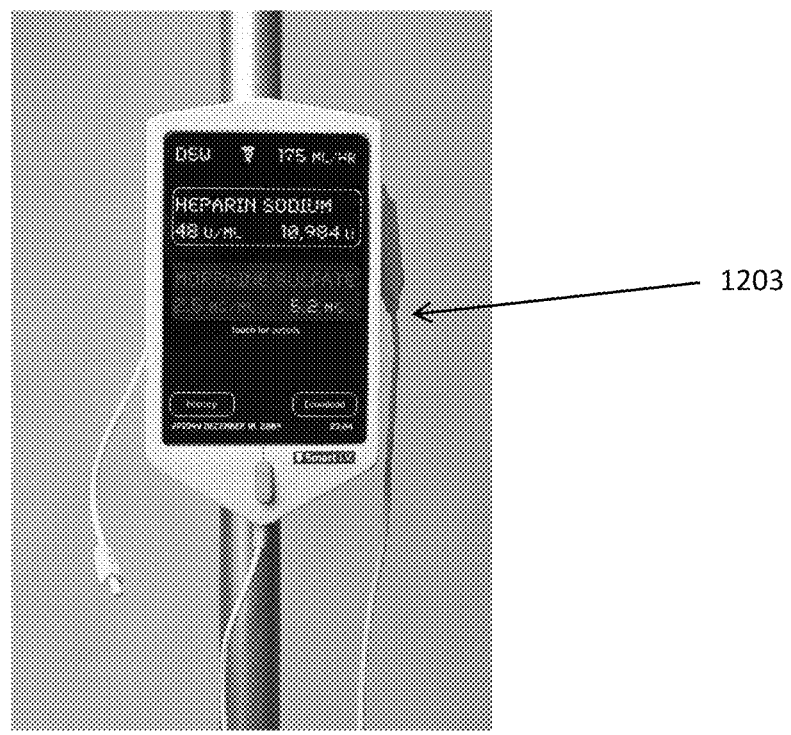
FIG. 12 shows a processor and display for use with an admittance spectrographic device for determining the composition of an IV fluid.

FIG. 11 shows another variation of an in-line sensor 1103 connected to an IV line 1105. The sensor may be wirelessly or directly connected to a processor (not shown). FIG. 12 illustrates one variation of a processor and display 1203 for an in-line sensor such as the one shown in FIG. 11. The display may indicate the identity (e.g., "Heparin", "Morphine Sulfate") and the concentration detected (e.g., 48 U/mL, 2.4 mg/mL) as well as the total (cumulative) dosage delivered. The cumulative dose may be shown numerically (e.g., 10, 984 U, 5.2 mg), graphically, or both.

In some variations, the probe (including the electrodes for determining the complex admittance) may also include a flow sensor, or may receive input from a separate flow sensor. Knowing the flow of the fluid as well as the instantaneous concentration as the IV fluid is being delivered allows for very precise estimates of the total dosage delivered.

In any of the variations described herein, when the system or device is associated with a particular patient, the system or device may be configured to customize the output based on patient-specific parameters. For example, the system may be programmed with patient data indicating what drugs (or what dosages of drugs) are to be applied. In some variations, the system may communicate with a patient's electronic medical chart. Access to patient information may allow the system to control drug delivery, and/or to warn of potential adverse events. Even when patient-specific parameters are not available to the system or device, it may provide information (alerts, warning, etc.) indicating variance from typical values, for example, when a particular drug's concentration and/or dose exceed an expected value.

In any of these example, the system may include a log (which may be a non-volatile memory) storing the output of the system (e.g., drug identity, concentration, dosage, etc.). The logged information may be connected to the patient's medical information (e.g., recorded or included as part of their medical records).

Integrated Systems and Devices

In some variations, the devices and systems for determining the composition of a fluid are not stand-alone devices and systems, but are integrated with other devices. Thus, these devices and systems may communicate and may share components with one or more other devices, including medical fluid delivery devices (pumps, syringes, tubing, etc.) and medical monitors (flow sensors, drip sensors, IV stands, etc.), workflow and medication tracking systems (pharmacy) and compounding devices/robots, and the like.

For example, a system or device for determining the composition of an IV fluid may be integrated with, and may control an IV pump. As mentioned above, the delivery rate of the IV pump may be regulated based on the actual (rather than estimated) concentration and dosage of an IV solution when the actual concentration and identity of the solution can be monitored in real-time, as described herein. In some variations, the system may warn of a dangerous dosage level, and may automatically shut off delivery of the IV solution. For example, to change dosage rate, the sensor system and processor can provide the drug identity, drug concentration, flow rate and delivery rate, and this information can be fed into a control system to adjust the pump flow rate as needed to ensure the proper delivery rate of a drug or drug combination.

The systems and devices described herein may provide input to a delivery control system that controls an IV pump, and thereby help to control the total IV drug dosage delivered. For example, sensor data can be integrated to determine total delivered dosage and this information can be fed into a control system to reduce or stop pump flow when a prescribed dosage has been administered.

In some variations the systems and device may be used to help control IV pumps to ensure that the correct drug sequence is delivered. For example, when two or more drugs are attached to one multi-channel pump, or two or more single channel pumps, the sensor system can be used for controlling a programmed sequence of infusions by signaling to the pump(s) when each infusion is complete to allow the pump to initiate delivery of the next medication.

The systems may also be used to help control IV pumps to control drug combinations. For example, when two or more drugs are infused simultaneously from one multi-channel pump or two or more single channel pumps, the sensor system can be used to control the relative proportions of the drugs being administered by measuring the signature of the drug combination and sending signals to the pumps adjusting the administration rate of one or more drugs, thereby adjusting the relative proportions of the drugs administered. This would eliminate delivery errors associated with line connection errors in multi-channel pumps by verifying the drug in each channel, and may be particularly useful for preventing errors arising from crossing IV fluid lines.

As mentioned briefly above, the system can control an IV pump or pumps to stop or reduce flow in the event of a detected adverse drug event (ADE). When a drug error is detected, a signal can be sent to an IV pump to stop, suspend or reduce the flow to avoid patient harm. A warning signal may also be transmitted to a monitoring system for intervention by a healthcare worker. The system may also control an IV pump based on detection of drug solution concentration that is too high or low. When a drug is administered at too high a concentration, a warning signal can be generated and the pump stopped to prevent patient harm. If the concentration is too low, a warning can be sent to healthcare workers. When patient-specific information is provided, the system may control an IV pump based on detection of the wrong drug/dangerous drug for the specific patient. For example, the system may provide alerts or control the IV pump based on interrogation of electronic medical records of specific patients for prescribed medications/concomitant medications, diagnosed diseases, and medication allergies and correlation with drug and dose detected in the IV line.

In some variations, the system may regulate patient controlled analgesia (PCA). At home or in hospital/clinical settings, the sensor system can serve as a control ensuring that the programmed PCA limits for patient safety are not exceeded by independently confirming the drug and dose and reporting to the PCA pump. When excess drug is detected the PCA pump can automatically shut off or reduce flow of medication. In addition, A PCA disconnect circuit can be implemented through the sensor system, such that the sensor is an integral part of the PCA circuit and if disconnected, turns off the PCA unit.

Other embodiments of the complex admittance systems and devices described herein include the use in medical devices such as IV bags. For example, a complex admittance sensor may be included as part of an IV bag. A sensor system can be incorporated into an IV bag or introduced into it via an access port to measure the solution contained within the bag. This can be used to verify that the solution in the bag is what is expected and is of the correct concentration and/or dosage. If the sensor is part of the bag, it can be used to check the bag at any point up to administration to confirm proper compounding, handling and/or storage. Similarly, complex admittance sensors may be used in conjunction with syringes. Complex admittance sensors can be incorporated into a syringe body or a needle and used to identify the fluid drawn contained within or drawn into the syringe before it is administered to a patient.

Complex admittance sensors may also be used with pharmacy compounding systems including automated robotic compounding systems. For example, a complex admittance sensor system can be used with or incorporated into a hospital IV formulation compounding system to confirm the drug identity, concentration and dosage both during the formulation process and subsequent to it.

Electrodes for Measuring Complex Admittance

The systems and devices for determining fluid components described herein typically include a plurality of electrodes. Each electrode includes at least one fluid-contacting surface that is configured to contact the fluid to be probed by the system or device, so that the fluid may interact with the surface of the electrode to form a dynamic equilibrium against the surface (e.g., the layered structure described from FIG. 2). The surface interactions of a particular fluid are characteristic of both the composition of the fluid and the nature of the surface. As mentioned above, the systems described herein typically compare the complex admittance data from an unknown fluid against a library of known complex admittances. Thus, the electrode surfaces of the probe are controlled and maybe stereotyped, allowing comparison of sampled complex admittance data against the known complex admittance data without requiring substantial adjustments or normalizations of the measured complex admittances.

In general, the devices and systems herein may include one or more arrays of electrodes for determining complex admittance. The electrodes are typically arranged so that pairs or combinations of electrodes may be stimulated and measured in order to determine complex impedance or admittance. Thus, a collection of electrodes may be arranged as a probe, a test cell, a conduit, a flow-though chamber, or the like. All of these variations are configured to bring the test solution (e.g., IV solution) into contact with the electrodes. A collection of two or more electrodes may also be referred to generically as a sensor. Thus, a sensor may have multiple pairs of electrodes having fluid-contacting surfaces that interact differently with the test fluid or solution.

The electrodes described herein may be referred to as admittance electrodes, and may be configured in any appropriate manner. The system and devices described herein typically perform fluid admittance measurements in which at least 2 conductive or semi-conductive electrodes are used in contact with the fluid. In general, multiple electrodes may be excited by a waveform signal having variable voltage and frequency.

Electrodes may be formed of any appropriate material, including metals, semiconductor materials, glassy carbon, carbon nanotubes, nanowires, porous materials, or the like. In some variations, the electrodes are formed from semi-conducting oxides (ITO), sulfates, phosphates, etc. at various degrees of doping or ceramics. In some variations, the materials forming the electrodes are noble metals such as gold, platinum, palladium, rhodium, ruthenium, osmium, and iridium or their alloys. The electrodes may be formed of metals and alloys that generally are oxidation resistive such as niobium, tantalum or stainless steel, etc. or ones that form protective oxide layers such as titanium, aluminum, magnesium. The electrodes may be formed of metals with a thin protective layer such as $SiO_2$ that has been added over the electrode. The electrodes may be formed from combinations of any or all of the above discussed electrode materials.

For an electrical impedance sensor, multiple pairs of metal pads may be used. As discussed above, the electrodes used for admittance measurements may be polarizable (or fully polarized) electrodes. The electrodes may be formed of the same material, or of different materials. Different metals and pairs of metal pads will provide unique responses when exposed to drug compounds in solutions. For example if two electrodes each of gold, platinum and palladium may be used, and the following combinations of metal pads can be used for sensing: Gold+Gold, Gold+Platinum. Gold+Palladium, Platinum+Platinum, Platinum+Palladium, and Palladium+Palladium.

The electrodes may be formed of the same material, but may have different surface and bulk morphology, crystalline structure or granularity, which may present a different surface interaction between the fluid and the electrode. In some variations, the electrodes are of the same material, but the surfaces are chemically of physically modified and/or functionalized (chemically treated, coated, mono-layered, etched, plasma-etched, subjected to ion implantation process).

Pairs of electrodes may be formed of the same or different electrodes (e.g., electrodes having similar or different surface-fluid interactions). For example, a sensor may include multiple pairs of electrodes in which each electrode in a given pair of electrodes are formed from the same materials or are formed from different materials. In some variations, the sensor includes electrodes having three or more electrodes of two or more compositions simultaneously.

In general, the electrodes may be formed from pads, traces, lamellae, interdigitated or other patterns of material deposited on an insulating substrate.

The leads for connecting to electrodes may be formed from conductive material covered by a non-conductive layer to isolate them from the conductive fluid. In addition, part of the electrode surface may be covered with one or more insulating material, controlling the surface of the electrode exposed to the fluid. Thus, the electrode may include openings in a non-conductive layer that define the geometry of the working surfaces exposed to the fluid.

Figure 13A:
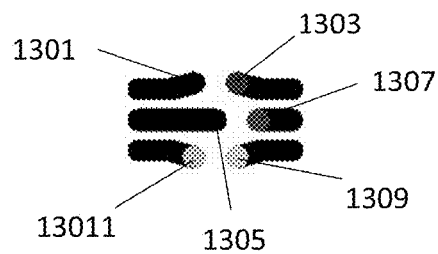
FIG. 13A is one variation of a sensor having six complex admittance electrodes arranged thereon.

In some variations the sensor includes electrodes for determining the complex admittance that are arranged as a probe. A probe may be configured for insertion into a solution or attachment to a vessel configured to contain the fluid. For example, In some variations of a sensor assembly, the sensor is a probe including electrodes having fluid-contacting surfaces arranged near each other. In some variations the distance between electrodes forming pairs is approximately the same. FIG. 13A illustrates one variation of a probe including six electrodes that each have a fluid-contacting surface 1301, 1303, 1305, 1307, 1309. In this example, the electrodes are formed as a layer on top of a conductive element (shown in black) that is insulated. The insulation is open only over the fluid contacting surfaces of the electrodes (shown as circles in this example).

Figure 13B:
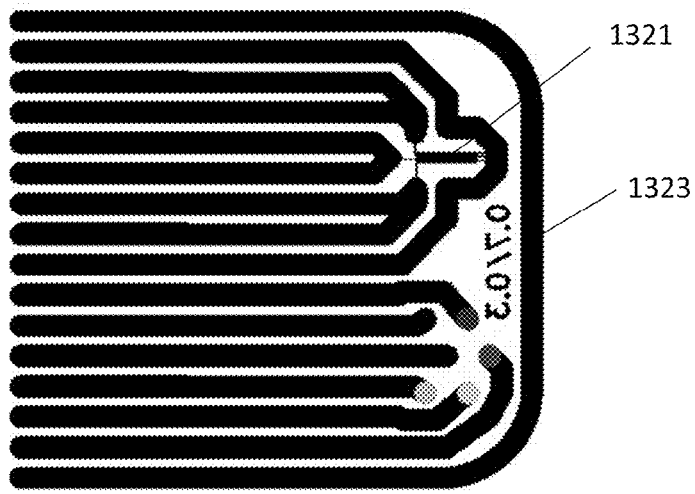
FIG. 13B is another variation of a sensor including six complex admittance electrodes (similar to those shown in FIG. 13A), and a flow sensor (thermal anemometer flow sensor) and an optical waveguide.
Figure 13C:
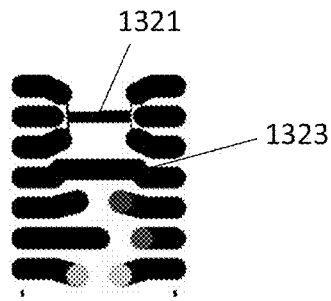
FIG. 13C is a miniaturized version of the sensor of FIG. 13B.
Figure 13D:
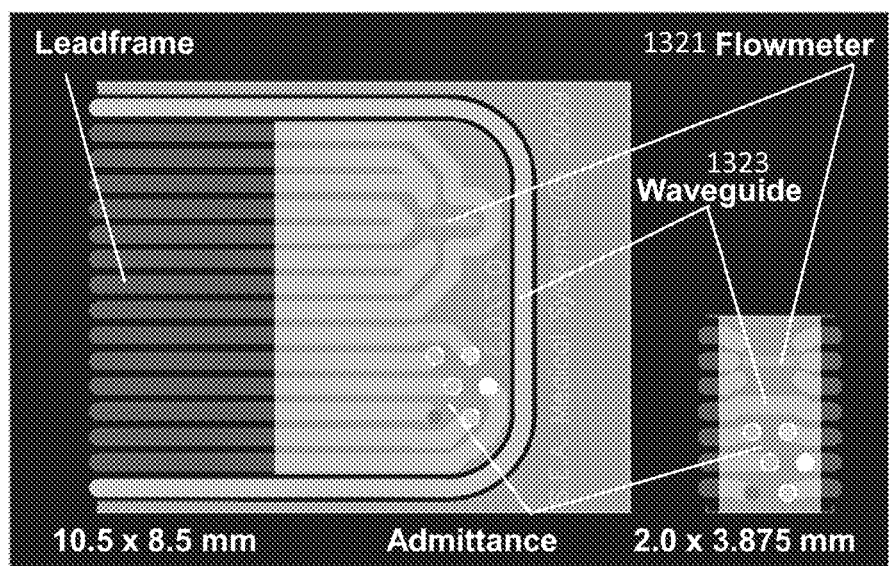
FIG. 13D shows another view of the sensors of FIGS. 13B and 13C.

In addition to the electrodes for determining admittance, a sensor may also include additional sensor elements, including sensors for measuring other characteristic fluid properties such as refractive index and/or optical absorption (e.g., optical sensors, etc.). A sensor may also include additional sensor elements for determining bulk properties of the fluid, such as thermal conductivity or thermal diffusivity and/or whether the fluid is steady or flowing. For example, FIG. 13B shows one variations of a sensor including six admittance electrodes (arranged as shown in FIG. 13A) as well as a thermal anemometer flow sensor 1321 and an optical waveguide 1323 all incorporated into a single assembly. As in FIG. 13A, the traces shown in black are formed of thin films of a metal such as gold. The color dots represent thin films of other metals deposited to form pads. The active areas of these sensors are the metal pads at the end of the traces. These pads are of different metals chosen to be compatible with immersion in typical IV carrier fluids. The admittance electrodes include an insulating coating except in the area of the metal pads. This coating prevents contact of the sensor leads with the conductive fluids but exposes a portion of the pads for direct contact with the fluid being tested. This sensor may be fabricated by known semiconductor fabrication techniques, which may provide precise control of the exposed surfaces of the admittance electrodes. For example, the probes may be produced by lithography on glass or other substrates. FIG. 13C shows a compact variation of the sensor array of FIG. 13B. FIG. 13D is an alternative view of FIGS. 13B and 13C, indicated the leadframe region of the sensor array, which may be coupled or connected to the rest of the systems for determining fluid composition. The dimensions of the example shown in FIG. 13D are: 10.5×8.5 mm, and it is integrated with lead frame as shown on the left side of the figure. The compact embodiment shown in FIG. 13C is approximately 2.5×3.875 mm.

Figure 14:
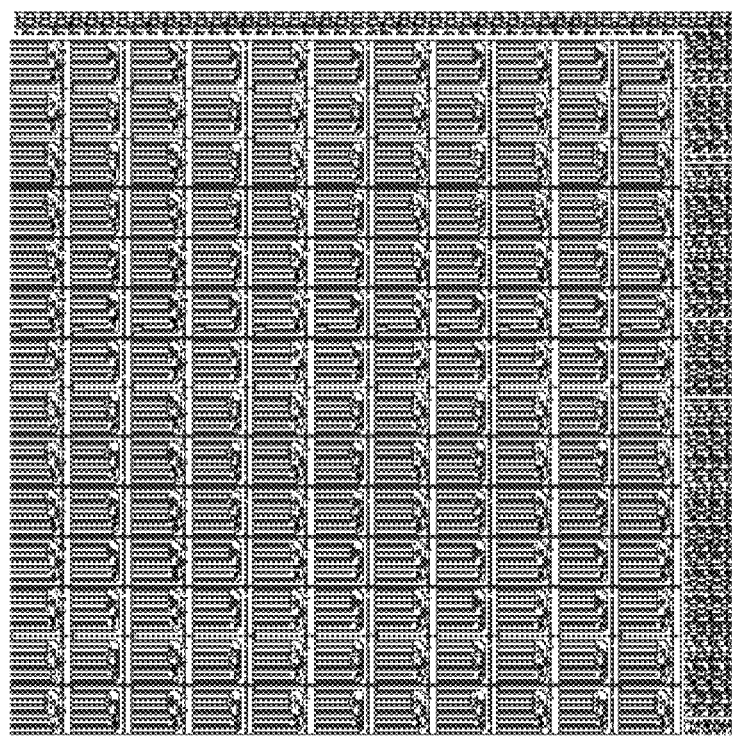
FIG. 14 is a panel of sensors similar to those shown in FIG. 13B that may be manufactured using metal deposition and lithography.

The variations shown in FIGS. 13A-13D also illustrate the concept of highly reproducible disposable or single-use sensors. The sensor arrays may be fabricated to a very high level of accuracy so that a new, previously unused sensor may be inserted in the system, used to test a solution, and removed. The used sensors may be recycled or reconditioned. For example, FIG. 14 shows a full panel of sensors similar to those shown in FIG. 13B that may be manufactured using metal deposition and lithography. The overall dimensions of the panel of sensor elements are 5×5 inches, and the individual sensors may be cut apart, or tested as part of a panel or strip (e.g., left connected, but used to test separate fluids).

The sensors described herein may also be configured as a measurement cell. A measurement cell may be configured so that the sensor forms the bottom of a chamber to contain the fluid, or the sensors may form a part of the wall of the chamber. In some variations, the measurement cell is sealed until ready to use and is punctured by a needle to introduce the sample to be measured. The measurement cell may be sealed and evacuated so that the sample will be drawn in by the differential air pressure. A measurement cell may be filled by capillary action of fluid through a capillary, micro-channel, wick or other sponge-like porous material. In some variations, the cell is sealed and may contain a measured amount of dry material or ionic fluid to introduce additional ions into the solution to be measured. In this case, electrolyte may provide ions for improved measurements of solutions that are in water or dextrose solutions. The presence of the additional electrolytes may be included in the analysis and recognition of the drug signature and should be compatible with the drugs to be measured.

In some variations, the system includes a measurement cell in which a second identical sensor or sensing site is exposed to a sample of a standard reference fluid such as normal saline, in a sealed chamber, while the first sensor is exposed to sample of fluid under test. The excitation is applied to both sensors and the signals from both are collected simultaneously and used for differential and/or ratiometric measurements.

The sensor or measurement cell may be compatible with automated use. For example, the measurement cell may be contained in a track or belt such as that used to contain surface mount electronic components for automated pick and place assembly. In the electronics industry, this is known as "tape and reel". In some variations, the measurement cell is configured to be part of a strip of measurement cells.

Signal Generator

In general, a measurement of the complex admittance is performed by the application of energy across a pair of electrodes, as illustrated above. Any appropriate signal generator (excitation source) may be used. The applied signal is typically less than 1 V (and typically less than 0.5V).

The electrical impedance sensors are excited for detection of admittance signals by applying energy across pairs of electrodes, as illustrated above. Admittance electrodes can be excited with a voltage waveform, voltage at a single fixed frequency, a set of two or more discrete frequencies, and/or a continuous sweep of frequency over a defined range. In some variations, a DC bias current may also be applied on top of the AC excitation to provide different measurement conditions. The data from these measurements provide signals related to both the surface property and bulk property and therefore the composition of the fluid contacting the sensor. Thus, pairs of electrical impedance sensor pads, such as those shown above in FIGS. 8 and 13A-13D, can be excited with ac current at a single fixed frequency, a set of two or more discrete frequencies, and/or a continuous sweep of frequency over a defined range. For each frequency, one or more excitation amplitude levels may be applied to the sensor.

Thus, the signal generator may be configured to apply a single excitation frequency, or two or more different excitation frequencies. In some variations, the signal processor is configured to apply 10 or more different excitation frequencies. As mentioned, the signal processor may be configured to continuously sweep the frequency from a starting frequency to an end frequency. The applied frequency may be varied in defined steps from a starting frequency to an end frequency. In some variations, the swept frequency fluid admittance measurements are taken in which the start frequency is lower than the end frequency, or the start frequency is higher than the end frequency.

In some variation, the excitation signal consist of a pure sine wave, an amplitude-modulated sine wave, a frequency modulated sine wave or phase-modulated sine wave. The applied time varying excitation signal waveform may be a shaped waveform, such as a square waveform, a triangular waveform, a sawtooth waveform, an arbitrary function of time waveform, or noise of various kinds such as white noise, pink noise of flicker noise.

The signal generator may apply energy to the admittance electrodes at a single excitation voltage level, or at different excitation voltage levels. For example, the signal generator may apply energy to the admittance electrodes at 10 or more different excitation voltage levels. The ac excitation level may be at or below the thermal energy level in the material to be tested. As mentioned, in some variations, a dc bias voltage is applied in addition to the ac excitation.

In some variations, the system is configured and arranged, so that the excitation signal and the measurement system are switched between pairs of electrodes. The switching may be controlled by a timer, a computer or other controller (e.g., microcontroller). The excitation signal level, as well as the excitation signal frequency, may be controlled (separately or jointly) by a timer, a computer or other controller (e.g., microcontroller).

In some variations, switching between excitation frequencies and/or pairs/sets of electrodes may be synchronized with the excitation voltage so that the switching takes place only at the predefined levels of the excitation voltage, such as in case of the sine waveform when exhilaration voltage is crossing zero level or when it reaches maximum or minimum or any other predefined level.

In some variations, the system may be configured so that a single signal generator is used. In some variations, the devices or systems may include multiple signal generators. For example, the system may be configured to energize more than 2 electrodes or pairs of electrodes and measured simultaneously at the same frequency or at different frequencies.

In variations in which electrodes that are not used for admittance measurements are used (for example, where electric flow detectors such as an anemometer), the same single generator may be used, or a separate signal generator may be used.

In any of the variations described herein a controller may also be used. As mentioned, the controller may be a dedicated controller (such as a microcontroller), or it may be a general-purpose computer adapted for use. In some variations, the processor is integrated with the controller. The controller generally regulates the generation of excitation waveforms, as well as any additional sensors, and can regulate the switching between sensors. The controller may also collect data from the sensors (including the admittance electrodes), store and/or distribute data collected. Thus, a controller may be used for sensor and detector response conditioning and read-out. The controller may perform these functions itself, or it may coordinate performance of these functions by one or more sub-systems.

For example, the systems and devices described herein may include a controller that controls digitization of sensor and detector responses. The controller may also filter and store digitized data. The controller may also pre-condition the data (e.g., by amplifying it, smoothing or filtering it, or subtracting it from a baseline, etc.).

In some variations, the system also includes a network interface for communication with one or more networks (which may be wired or wireless). The system or device may also include a user interface, including appropriate user inputs and outputs (displays/printers, keyboards, buttons, touchscreens, trackballs, etc.).

In addition, the system may also include one or more memory elements for storing data, including storage of stimulation parameters and user-input data. Stored information may also include a log of the performed measurements and/or full history of infusion treatment based on measured drug identities, concentrations and flows along with the timestamp. Any appropriate (digital) memory may be used, including removable media memory.

Processor

The systems and devices described herein also typically include a processor for analyzing the complex admittance (e.g., the admittance spectroscopy fingerprint) and comparing it to a library of known complex admittances, and any additional characteristic parameter measured. The processor may be electronic, and may include hardware, software, firmware, or the like. The processor may be a dedicated processor, or a general-purpose processor, and it may be local or remote. In some variations, the processor is a distributed processor.

The processor may include a library of known parameter values. The parameter values are coordinated to a solution having a known identity and/or concentration of components. The parameter values may include the complex admittance values measured from known fluids at defined compositions and concentrations. The library may be stored in the memory of the processor, or it may be accessible (remotely or locally) by the processor. For example, the library may be stored to a flash drive that can be updated periodically, or it may be located on a remote server and accessed (or downloaded) by the system or device. In some variations the library may be constructed or added to by the system or device, operating in a calibration mode.

In general, the library values are measured under similar conditions as the test conditions. In particular, the complex admittance may be measured using a sensor that is configured similar or near-identically to the sensor used by the testing device or systems. Thus, the library may include complex admittance data that corresponds (or matches) the measurement parameters of the admittance electrodes. For example, the library admittance spectrographic fingerprint for a known composition of fluid may be indexed by the same electrode pair (e.g., Au—Au, etc.) at the same applied energy (frequency and energy level). The admittance electrodes making the measurement do not have to be the actual electrodes used to determine the library reference admittance parameter, however, they should have approximately the same surface interaction, which may mean that the material forming the fluid-contacting surfaces and the geometry of the fluid-contacting surfaces may be approximately equivalent.

The fingerprint collected from the test device or system may include more or a subset of the parameters in the fingerprints of the library. In general, the processor may use only a subset of the parameters (e.g., the admittance spectroscopy and any other characteristic data) to identify the composition of the test sample.

The processors described herein also typically include logic for recognizing patterns between the test fingerprint and the library of fingerprints. For example, the processor may include pattern recognition algorithms trained to recognize patterns corresponding to known solutions (e.g., solutions having drugs or mixtures of drugs in a carrier). For example, the processor may include logic that is configured to perform multi-dimensional data clustering, pattern recognition and/or neural network algorithms utilized for drug recognition from the training patterns. The processor logic is typically executable on any appropriate hardware, firmware or the like, as discussed above.

Algorithms for recognizing drugs from multi-parametric sensor data may utilize sensor data from multiple channels to identify drug compounds in a solution. The data set examined (e.g., the fingerprint) may include single data points, two dimensional curves, as well as pathways in multi-dimensional space to recognize specific drug compounds. In some variations, software algorithms to detect drugs from the data input can be based: thresholds, peak fitting and analysis, clustering, and angles in 2D or multi-dimensional space. The processor may include neural networks that are trained on the library of known drug solutions, and interpolate between known data points to determine the identity and concentration of drugs or mixes of drugs.

Any appropriate pattern-recognition or classification algorithm may be used by the processor to determine drug identity and/or concentration. As described herein, in some variations the complex admittance (and any other characteristic parameters measured) may be represented as a vector, including multidimensional vectors of greater than $2^{nd}$ and $3^{rd}$ order (n-dimensional). For example, the fingerprint taken from the sample may be curve fit to define the equation of the path taken by the curve through a multidimensional space for each drug versus concentration.

In some variations, the processor could include logic or algorithms for comparing and/or recognizing fingerprints that has been hard coded into a specialized chip (e.g., FPGA, etc) configured to run as hardware rather than software. In this implementation, the specialized chip could be pre-programmed or trained with the drug patterns and could do hardware-level matching of sensor input patterns with those preprogrammed into the chip.

In some variations the pattern recognition logic may be referred to as "adaptive." As used herein, the term adaptive generically refers to a trainable system or network (e.g., an adaptive neural network trained on the library of fingerprints). In some variations, the pattern recognition logic may also be pre-trained, or fixed, and not "trainable" in a conventional sense. For example, a network may be constructed to recognize test fingerprints based on a library of fingerprint data.

A processor may generally receive the fingerprint "pattern" (e.g., the complex admittance data and any additional characteristic data), and compare the pattern to the known library fingerprint patterns. The processor may perform some or all of the following steps: pattern acquisition, feature extraction, pre-processing, classification, regression description, pos-processing and communication of results and/or alerts. Pattern acquisition typically represents collection of the multi-dimensional sensor data. Feature extraction may involve determination of signal levels and extraction of primitives, such as vectors or curve descriptors. Pre-processing may be required for the feature or descriptor values to be properly scaled and corrected for the device transfer function, including any nonlinearity of sensors and electronics response. This may be an especially useful function if neural network algorithms that require features to be scaled to unity are utilized. Post-processing typically interprets the output obtained from the classification, regression and description steps. Based on identification of the compound(s) in solution, this step may include loading information on sensitivity of the patient to the identified drug, and calculate the concentration and the dose and sends a message to either a pump interface or graphic user interface, which may generate an alert.

As mentioned, any appropriate pattern recognition algorithms may be used, including data clustering algorithms, statistical classification algorithms, neural network algorithms and structural analysis algorithms.

A simplified example of the drug recognition process that a processor may perform is provided. In this example, a pair of metal electrodes are exposed to a fluid, and the surface interaction between the electrodes and the fluid can be investigated by energizing the electrodes with an AC voltage or current and measuring the resulting complex current or voltage. As described above, when the stimulus signal is small enough for the system to respond linearly, the system can be described in terms of complex AC impedance or admittance, e.g. real (x) and imaginary (y) response components can be measured.

The values of x and y as well as their relative magnitude change predominantly with the electrical properties of the fluid flow and fluid-electrode interface, both of which are greatly affected by the composition of the flow. The change in these values is correlated to the nature of the fluid material and may be used to identify the particular material. In the case of IV drugs, the responses may be used to identify the particular drug(s) present in the flow of a carrier fluid such as saline or Ringer's lactate.

In this example two circular coplanar gold electrodes of 0.32 mm in diameter are placed at 0.75 mm distance from each other on a wall of a non-conductive flow path. A 100 KHz AC voltage of 8 mV amplitude was applied across the electrodes in series with a 50 Ohm resistor and the voltage drop across the resistor was measured using a Stanford Research Model SR830 lock-in amplifier. A PC was connected to the lock-in amplifier via RS232 interface with software recording the complex voltage read by the lock-in approximately twice per second. The data was plotted with the real part of the measured voltage value along the X-axis and the imaginary part along the Y-axis. In this experiment, due to the naturally occurring noise, an average $(x_0+iy_0)$ and standard deviation ($\sigma$) were determined. A measured voltage value $(x+iy)$ deviating from the average value by $|\Delta x + i\Delta y| > 6\sigma$ in any direction on the XY chart is a statistically significant indication of a change in the fluid. In this case, $\arg(\Delta x + i\Delta y)$ defines the angular direction of the deviation vector. Two deviations $\Delta x_1 + i\Delta y_1$ and $\Delta x_2 + i\Delta y_2$ are statistically distinguishable if $|\Delta x_1 + i\Delta y_1| > 6\sigma$ and $|\Delta x_2 + i\Delta y_2| > 6\sigma$ and $|\Delta x_1 - \Delta x_2 + i(\Delta y_1 - \Delta y_2)| > 6\sigma$. The latter inequality defines the relationship between the magnitude of the deviations and the angle between them for the deviations to be distinguishable from each other.

Our experiments demonstrated (and can be explained theoretically) that for highly diluted additives to the saline flow the deviation distance from the pure saline point depends on both concentration and molecular or ionic composition of the additive, while the direction depends predominantly on the molecular or ionic composition of the additive. For higher concentrations of the additive both magnitude and direction of the deviation become concentration-dependent in unique and distinguishable manner depending on the nature of the additive.

In this example, the sensor is measuring flowing saline and a 1 ml of drug such as saline-diluted potassium chloride is injected into the flow as a bolus dose. Once the "front" of the bolus reaches the vicinity of the electrodes, the complex current deviates from its average value in pure saline and returns back when "trailing edge" of the bolus passes the vicinity of the electrodes, producing a characteristic curve or signature. It can be seen that the "front" of the potassium chloride injection produces deviation from saline point which is a nearly straight line at a distance far greater than the $6\sigma$ threshold of detection, which allows for accurate determination of the direction of the deviation vector. For example, a linear regression of the measurement points from the $6\sigma$ threshold of detection to the distance may be performed where residuals start exceeding $6\sigma$. To make the results more comprehensible, an angle between X-axis and the directional vector of the deviation based on the regression coefficients may be calculated, which was found in this example to be 74.4°.

Figure 32:
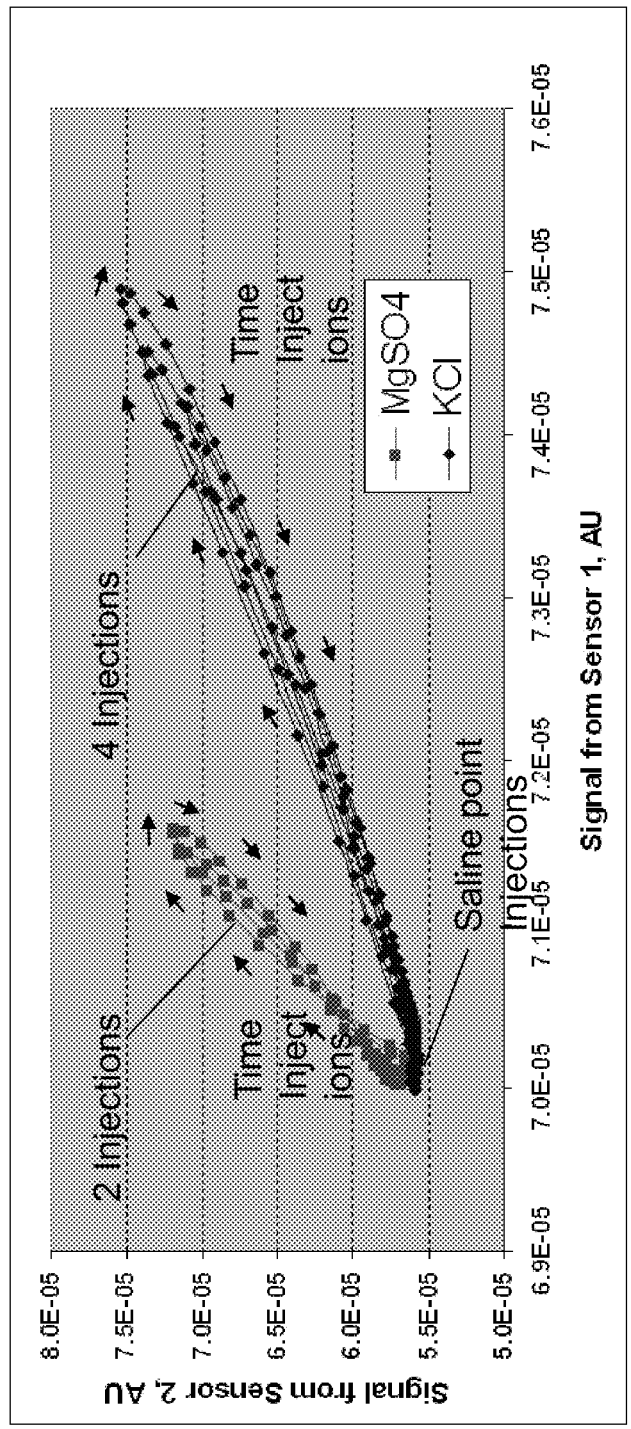
FIG. 32 illustrates one example of the different vectors distinguishable from different components (e.g., $MgSO_4$ and KCl) in solution.

When a 1 ml of saline-diluted magnesium sulfate bolus was injected into the system, the measured complex voltage traced a curve very different form the potassium chloride injection. As can be seen in FIG. 32, the deviation from the saline point is more vertical, and of a smaller magnitude. The angle of the initial deviation calculated as explained above was found to be 85.6°.

Approximately 1 ml of plain deionized water was also injected into the saline flow. The water generated a different curve, deviating in nearly opposite direction from the previous injections. The angle of the initial deviation for a water injection was found to be −118.2°.

The statistical uncertainty for these angle measurements was estimated from the residuals of the linear regression used to calculate coefficients determining the angles and for all three substances was found to be ±0.62°.

In some variations, the processor may be configured for recognition of drugs by continuously collecting data from the sensor(s) and checking whether the value exceeds the $6\sigma$ threshold. Once the threshold is exceeded, the software indicates that a different substance is likely present in the flow and starts linear regression on the consecutively measured points, checking whether residuals exceed the $6\sigma$ threshold. At that point, the algorithm may conclude that the linear section of the deviation curve is over and calculates a directional vector of the data set being reduced. The directional vector can then be compared to values previously determined for the vectors for specific drugs. In some variations, the analysis can be done in terms of angles. For example, if the detected deviation falls within 74.4±0.62°—the injected bolus is likely potassium chloride, if it falls within 85.6±0.62° or −118.2±0.62° the injected substance is magnesium sulfate or water respectively. If the angle is outside the known boundaries the algorithm reports the unknown substance in the flow. The same analysis may be performed using more than two dimensions, as mentioned above.

This simple algorithm can be adapted to recognize other substances that produce deviations in various directions by supplying the values for the expected angles. Much more elaborate pattern recognition algorithms can be applied to the differentiation and recognition of curves generated by the sensing system in multi-dimensional space, as described, for example, in Sing-Tze Bow, Pattern Recognition and Image Preprocessing, 2002; M. S. Nixon, A. S. Aguado, Feature Extraction and Image Processing, 2002; and D. Maltoni, D. Maio, A. K. Jain, S. Prabhakar, Handbook of Fingerprint Recognition, 2002. For example, the recognition software can be based on artificial neural network and fuzzy logic algorithms.

The processor may also include algorithms for determining potential drug errors. For example, the processor may calculate, based on the identified drug, concentration, and flow data, the dose of a particular drug that a patient is likely to receive, and compare the projected dose with pre-specified dose limits that are generally safe for patients. This allows drug errors to be anticipated. In some variations, the processor also incorporates patient data such as, but not limited to, body weight and age to improve prediction of errors in progress and/or expand the number and types of error detected. Patient data can be automatically retrieved from EMR (electronic medical record) or programmed into the unit manually via computer or directly into the processor.

As mentioned, the processor may be all or partially local or remote from the rest of the system. For example, in some variations the data processing, drug recognition and ADE detection takes place fully at the sensor's local processor. In other variations, the data processing occurs at least partially at the sensor's processor and partially a pump's microcontroller (embedded microcontroller). In some variations, all of the processing of the test fingerprint occurs at a remote processor(s), for example, at an IV pump's microcontroller or on a remote server within a health care provider's network.

As mentioned above, the devices and system described herein may include a log or memory for storing or recording the results of the use of the device and/or operational data. An infusion log is typically stored in and downloadable from a processor or pump microcontroller or both. A log of the detected drugs and dosages may be stored in memory associated with the processor, IV pump or a remote receiver unit. Such data may be later transmitted to a hospital IT system or downloaded from the local device.

Although the majority of variations described above encompass systems and devices in which the admittance spectroscopy is used to both identify the components of an unknown solution and to verify the concentration of the components, in some variations, the system or device may be configured to determine just the identity of one or more components of a solution.

One variation of the admittance spectroscopy methods described herein provides a special case for the determination the identity of one or more components of a solution. At low concentration (e.g., under highly dilute conditions), the identity of one or a mixture of drugs in solution may be readily determined, independent of the actual concentration.

As mentioned above, the angular dependence of multi-dimensional signals, including electrical signals, may be determined for a particular electrode pair based on the complex impedance. This may allow an approximation of the identity of the compounds as the concentration of the compound(s) in solution increases from zero to a non-zero value. Expressed as a vector, the direction of the multi-dimensional signal's vector may reflect the identity of a compound (or identities in the case of mixtures of compounds). We have found that for some drugs at low concentrations, the angles resulting from the in-phase and quadrature components of the ac signal are independent of concentration. The angle therefore depends only on the nature of the drug, and not its concentration. Since the systems described herein are multi-parametric, and multiple signals are recorded for each substance or mixture of substances in solution, the response may be represented by a vector in sensor signal space.

Thus, in some variations, the measurements may be performed on the background of a known carrier infusion fluid (e.g., 0.9% saline, solvent, or other typical fluid such as Ringer's Lactate or Dextrose solution). In this case, the identity may be determined as the concentration initially increases from zero in the carrier, independent of the eventual final concentration. Thus this variation it may be convenient to place the origin for the frame of reference at the end of signal vector generated for a known carrier infusion fluid (e.g., saline) and operate with the signal deviations from that point rather than with the full signal vectors and call deviations from the know carrier infusion fluid point "signals". The sensor signals may exhibit non-linear responses to drug concentration that are different for drugs of different type and parameters. At very low drug concentrations, the sensor signal will be approximately proportional to the concentration (the non-linear response to concentration can be represented by a Taylor series in the neighborhood of a known carrier infusion fluid point and only linear term retained). In this case the constant in the linear term can be called "sensitivity", each coordinate of the response vector $(r_1, r_2, \ldots r_n$, is proportional to concentration $\Delta c$ and the vector coordinates are $s_1 \Delta c$, $s_2 \Delta c, \ldots s_n \Delta c$, or $\Delta c^*(s_1, s_2, \ldots s_n)$, where $s_i$ is sensitivity of the i-th sensor signal (or channel) and vector $(s_1, s_2, \ldots s_n)$ can be called "sensitivity vector" that will be different for different types of drugs. If in a drug #1 of concentration $\Delta c$ the sensor produced response $\vec{r}$ and in drug #2 at concentration $\Delta C$ response $\vec{R}$ the cosine of angle between these two vectors can be calculated as:

$$\frac{\vec{r} \cdot \vec{R}}{|\vec{r}||\vec{R}|} = \frac{\Delta c \vec{s} \cdot \Delta C \vec{S}}{\Delta c |\vec{s}| \Delta C |\vec{S}|} = \frac{\vec{s} \cdot \vec{S}}{|\vec{s}||\vec{S}|}$$

where $\vec{s}$ and $\vec{S}$ are sensitivity vectors to drug #1 and #2 respectively. This consideration demonstrates that for small concentrations of drugs the angle between the response vectors does not depend on concentrations and depends only on sensor sensitivity to a particular drug, e.g. drug type. Therefore the angle between the response vectors can be used as a simple metric for distinguishing between the drugs independently of their concentrations as long as the concentrations are low. In the presence of naturally occurring noise, the angle between the vectors can only be calculated with finite accuracy determined by noise characteristics and sensitivity of the sensor response. For practical purposes, the angles can be calculated between consecutively measured response vectors for a number of measurements performed for a single drug and standard deviation calculated for such dataset would define the smallest angle that can be resolved and thus the maximum achievable resolution. For higher concentrations, the measured response of the sensors for a set of concentrations within range of interest for a given drug will be stored in memory in the form of a lookup table or polynomial fits, etc. This information will establish the calibration function:

$$\vec{r} = \vec{s}(c)$$

for a particular drug, so that once drug is identified the concentration of it can be calculated from the sensor response:

$$c = \vec{s}^{-1}(\vec{r})$$

This information is redundant for concentration calculations, so either only one sensor channel can be used, several channels or absolute value of the response vector, etc. depending on whether the noise is non-correlated or partially correlated between the channels. Once the drug is identified at the time t, the sensor response can be pulled out of the database and instantaneous drug concentration can be calculated:

$$c(t) = \vec{s}^{-1}(\vec{r}(t)).$$

If the drug concentration exceeds safe limits at any time during the injection, the system can provide an alarm. Once the drug is identified, the response data can be traced back in time to the point $t_0$ where the response first exceeded two standard deviations from the saline point. The cumulative dose D(t) at a time t then can be estimated as:

$$D(t) = \int_{t_0}^{t} q(t)c(t)dt,$$

where q(t) is instantaneous volumetric flow measured by the flowmeter.

Data Communication Methods

In the various examples of systems and described herein, the component parts of the system communicate with each other either by directly connecting to them (wiring) or wirelessly. Because many of the medical fluids to be sampled by these devices and system are conductive, aqueous solutions, in some variations the system may take advantage of the fluid other system components to communicate with other components of the system. For example, an IV fluid to be sampled may be used as a data communication channel. The sensor data stream may be encoded into electrical signals carried by the conducting fluids. Sensor data may be transmitted from the sensor assembly and/or processor unit through the IV fluid by using the fluid as a communication channel. Electrical signals can be transmitted through a conductive IV fluid at very low signal levels. Multiple data channels may be encoded by using different frequencies and/or modulation methods.

In some variations, the IV tubing may be used as a data communication channel. The sensor data stream can be encoded into signals (optical, acoustic, or electrical) that can be carried by the IV tubing. As a transparent plastic, the IV tubing can be used as a conduit to transmit optically, electrically or acoustically encoded signals from a sensor or processor to a receiver.

The IV fluid may also be used as a medium for conducting sensor signals through light. Sensor data may be transmitted by using the IV fluid and tubing as a medium for conducting light onto which the sensor signals have been encoded. In this case, the fluid and tube system can work like a fiber optic in acting as a conduit to contain the optical signals and transmit from one point to another.

In some variations, the sensor communication channels (wires, optical fibers, etc) may be incorporated into the IV tubing. Communication pathways can be built into IV tubing at the time of manufacture to provide a data pathway for transmitting sensor data. The incorporation of wires, conductive polymers and/or optical fibers will provide a means for transmitting signals from a sensor unit and/or processor unit to a receiver unit or to an IV pump.

A sensor unit processor and a pump may communicate through the IV line: Using the tubing or IV fluid as a media for communication electrically, optically and acoustically (ultrasound). Information from the sensor and or processor that is transmitted to the pump may include: flow rate, flow temperature, the presence of bubbles, drug identity, drug concentration, drug delivery rate, and carrier fluid identity.

The systems and devices described herein may also communicate sensor data to an IV pump by an optical interface. Communication can be by either a fiber optic link or free space optical signal link.

The systems and devices described herein may be integrated with one or more other devices (or components of the system) including IV pumps through serial, Ethernet, wireless or optical communication means. For example, a device or system may be linked to an IV pump through any common data communication interface including but not limited to the following: Ethernet, wireless, optical, and acoustic.

As mentioned above, communication of data from a sensor unit to a remote processor may be performed by wire, wireless or optical means. In this case, the processor unit may be located physically at some distance from the sensor unit and the sensor signals communicated through a communications link that includes but is not limited to the following: Ethernet, wireless, optical, acoustic, including ultrasound In some variations the IV fluid may be used by the device or system as an RF antenna. Thus, communication between the processor, the pump and hospital IT infrastructure and individual communication devices (PDAs, mobile phones, etc.) may be established wirelessly using IV fluid in the line as an antenna. RF signals may be coupled into the conducting fluid contained within the IV tubing or fluid bags which will act as an antenna to radiate and receive signals.

Outputs

The systems and devices for determining the components of an unknown solution described herein may include any appropriate output, including information outputs (displays, printouts, alert lights, sounds, etc.), memory outputs (logs, digital records, etc.), control outputs (changing the operation of a device based on the result), or any combination thereof.

For example in some variations, the system or device includes a display. The display may be coupled to the device or located remotely to it. The display may indicate the results of the analysis, including indicating the identity and/or concentration of one or more components of the fluid. A display may also provide instructions, and system information (e.g., indicating how to operate the device), or error codes associated with operation.

For example, a panel or display may be present on the sensor, processor or an IV pump integrated with the device. The display may indicate what drug(s) was/were detected and warns of unexpected drugs, concentrations and dosages. Drug identification information and ADE may be indicated in progress alert or messages that are indicated at the sensor's processor unit. In variations in which the system for determining the components of an IV drug solution is integrated with an IV pump, both the system and the IV pump (or just the IV pump) may include a display, such as a display using text display or light of various color and flashing sequences in order to provide an alert. The alert (e.g., triggered by potential adverse drug events) can also include but is not limited to: an audible alarm, an optical signal (glow, color change, etc.) when the medication being administered regardless of whether it is a potential error.

Audible alert signals may also be used. Similarly, specific audible alert signals may be generated by the sensor system or by an IV pump (or other associated device), or by only the IV pump. Such signals can indicate but are not limited to (when the presence of a high alert medication is triggered): an overdose or under dose condition or a drug that is contraindicated for the specific patient.

Visual alert signals may include flashing lights or the continuous glow of a specific color light. Visual and/or audio alert signals can encode the type and severity of the error in progress once the error is identified.

In some variations, the system may also indicate that it has been correctly/incorrectly connected, or has not been connected. For example, the system or device may indicate the presence or absence of the sensor in an IV line, and/or whether the communication between sensor processor and pump microcontroller has been established.

Use of Admittance Spectroscopy with Other Sensor Modalities

The general concepts of multiparametric sensor measurements to determine identity and concentration are herein developed in the particular case of admittance spectroscopy. However, these same general concepts may be applied using other modalities that detect properties reflecting characteristics of a particular solution composition. These additional modalities, examples of which are provided below, may be used in combination with the admittance spectroscopy devices and methods described herein.

The general principles of multiparametric analysis used to determine identity and concentration applied herein may be expressed in a general case. For example, two different sensors respond to index of refraction and specific weight may provide multiparametric data that may be used to determine identity and concentration. A sensor that responds to index of refraction or specific weight may have a measured response $\Delta r$ that depends on both the nature of the introduced component (properties such as MW, polarity, etc.), $\Delta p$, and its concentration, $\Delta c$. Thus: $\Delta r = f(\Delta p, \Delta c)$. From a single measurement, concentration can be deduced if the nature of the component is known and vice versa. When multiple sensors are used, the measured response is now a vector: $\Delta r = (\Delta r1, \Delta r2)$, which depends on both nature the introduced component ($\Delta p$) and its concentration ($\Delta c$): $\Delta r = f(\Delta p, \Delta c)$. For very low concentration $\Delta r \approx (\partial f(\Delta p,0)/\partial c) * \Delta c$. Value $\partial f(\Delta p,0)/\partial c$ does not depend on concentration and can be called "sensitivity vector". When the sensors are exposed to two different substances, $\Delta p1$ and $\Delta p2$, at concentrations $\Delta c1$ and $\Delta c2$, respectively, the response vectors will be $\Delta r1 \approx (\partial f(\Delta p1,0)/\partial c) * \Delta c1$ and $\Delta r2 \approx (\partial f(\Delta p2,0)/\partial c) * \Delta c2$.

The cosine of angle between these two vectors is their scalar product divided by their absolute values:

$$\cos(\phi) = (\Delta r1 \cdot \Delta r2)/|\Delta r1|/|\Delta r2| = [(\partial f(\Delta p1,0)/\partial c) * \Delta c1 \cdot (\partial f(\Delta p2,0)/\partial c) * \Delta c2]/(|(\partial f(\Delta p1,0)/\partial c) * \Delta c1| * |(\partial f(\Delta p2,0)/\partial c) * \Delta c2|) = (\partial f(\Delta p1,0)/\partial c) \cdot (\partial f(\Delta p2,0)/\partial c)/|\partial f(\Delta p1,0)/\partial c|/|\partial f(\Delta p2,0)/\partial c|.$$

Thus, in a generic sense, the angle between the sensitivity vectors depends only on the nature of substances $\Delta p1$ and $\Delta p2$ and is independent of concentration. The parameters informing the sensitivity and concentration vectors may include the admittance spectroscopy data, but they may also include additional sensor information, as mentioned above. Further, the dimensions of the system or method, e.g., the number of parameters, may be as large as desired, while still keeping the processing necessary to a manageable (e.g., real-time) level.

Thus, a multiparametric system, including particularly the admittance spectroscopy systems described herein, may be used to determine drug identity and concentration given an unknown solution including the drug (and nay other components). Although the complex admittance and the use of admittance spectroscopy provide a rich source of data for the identification of unknown solutions, the use of admittance spectroscopy is also compatible with other sensor modalities. The use of additional sensor modalities may enhance the admittance spectroscopic methods, systems and devices described herein. These methods may be particularly helpful in drug validation in a hospital pharmacy or similar environment. Validation of prepared doses is of high value to pharmacists and pharmacy technicians. Any error in a prepared medication can have very serious consequences if the erroneously prepared medication is administered to a patient. For example, multiparametric fluid measurement and analysis may use a combination of fluid admittance, multi-wavelength optical absorption and multi-wavelength refractive index sensing to determine the composition of a medical fluid (e.g., an IV fluid).

In addition to the admittance measurement techniques described above, the following sensor technology may also be used if needed for the particular application: an electrochemical sensor (e.g., an electrochemical potential sensor), a thermal sensor (e.g., a thermal anemometer sensor can be operated as fluid thermal diffusivity sensor), an optical sensor (e.g., a refractometry sensor, a transmission sensor, an absorbance sensor, a spectrometer (including a colorimeter), a turbidity sensor, a rheological sensor (e.g., a viscometer), an electrical property sensor (e.g., a capacitor sensor, a pH sensor, a conductivity sensor, and an inductive sensor), and a fluid-displacing or fluid-shearing (e.g., resonator) sensor. Fluid properties and sensor technology to measure these properties are shown in the table below:

TABLE 1

Alternative sensor modalities

| Fluid Property | Sensor Approach |
| --- | --- |
| Complex conductivity or admittance | AC impedance spectroscopy |
| Ionic properties | Electrochemical potential/spectrum |
| Boiling point | Pulsed thermal anemometry, |
| Thermal diffusivity | Pulsed thermal anemometry |
| Index of refraction | Refractometry, fiber optic refractometer, optics |
| IR, Vis., UV absorption | Transmission/Absorption |
| Color | Spectrometer, colorimeter, white light absorption spectra |
| Viscosity | Viscometer, resonator |
| Density | Viscometer, resonator |
| Dielectric constant | Capacitor, resonator |
| Opacity or Clarity | Optics, transmission, turbidity sensor |
| Membrane permeability | Selective sensors |
| Ph | Ph meter, MEMS ph sensor, chemical color change sensor, litmus paper |
| Salinity | Conductivity, density, refractive index |
| Air | Optical, inductive, conductivity, thermal, |
| Flow | Flow meter, thermal anemometer |

As an example of the application of different sensor modalities, consider a sensor that responds to the liquid's index of refraction and another sensor that responds to liquid's conductivity. Assume that there is a carrier fluid, such as saline (0.9% saline in water) solution, in which an additional component, such as drug, is dissolved. Further, assume that both sensors' responses reach values $r_1$ and $r_2$ when an additional component is present in the liquid. Both the index of refraction and conductivity will depend on the added component concentration c and its "nature": aggregate effect of parameters such as molecular weight, polarity, ionic strength, etc.—p. The individual sensor's response is function of both concentration and nature of the added component:

$$r = f(c,p)$$

therefore, the response of an individual sensor can only be calibrated to measure the concentration of a known component or determine what the component is if the concentration is known. If the response from the second sensor is utilized, both the concentration and the nature of a component can now be measured:

$$r_1 = f_1(c,p); r_2 = f_2(c,p)$$

as this system of two equations with two variables can be solved in the majority of practical cases.

Two sensor responses can be treated as a 2D vector and the equations can be written in vector form:

$$\vec{r} = \vec{f}(c,p)$$

Notice that for components of a different nature $p_1, p_2 \ldots p_n$ end of this vector traces curves $\vec{r}_1(c) = \vec{f}(c,p_1)$, $\vec{r}_2(c) = \vec{f}(c,p_2) \ldots \vec{r}_n(c) = \vec{f}(c,p_n)$ as concentrations change and all curves at zero concentration start from the same point, which is the response in the carrier fluid. The components of interest these "concentration curves" or "signatures" can be experimentally recorded and stored in a database. When an unknown solution is measured—the response can be matched with the database of signatures.

This simple explanation can be expanded to more than two sensors without the loss of generality. Additional sensors provide additional dimensions to the vector and for the case of a single component this information becomes redundant. This redundancy is very useful in practice as the experimental curves are always blurred by naturally occurring noise and any additional information improves overall resolution power of the technique.

Figure 15A:
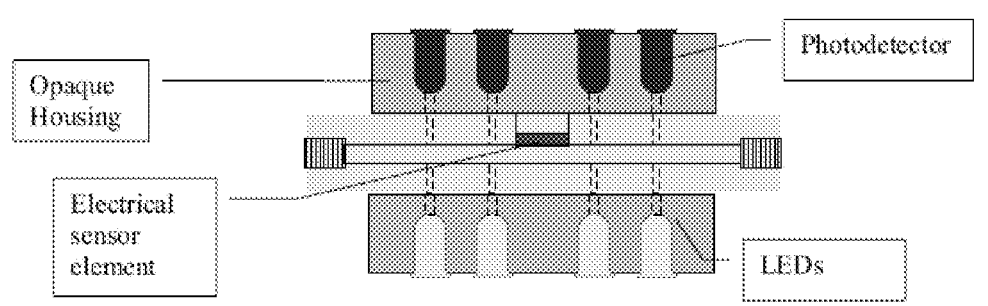
FIGS. 15A and 15B illustrate one variation of a flow chamber including an array of complex admittance electrodes and optical sensors that may be used to determine the composition of an IV fluid.
Figure 15B:
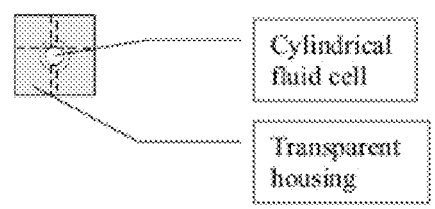

One example of a combined electrical (admittance spectroscopy) and optical system was illustrated above for the probe shown in FIGS. 13B-13D. Another variation of an array of sensors (configured as measurement cell) is shown in FIGS. 15A and 15B, incorporating a transparent chamber through which fluid flows. In this example, a set of optical sources such as light emitting diodes (LEDs) that emit light at discrete wavelengths in the range of 250 to 1000 nm or more are embedded across from a set of matched detectors (matched to the emitting optical source), so that the light pathway spans the transparent fluid pathway. The optical detectors may be photo diodes or phototransistors with response matched to the optical sources (e.g., LEDs). An opaque holder for the optical sources and detectors may be used to align them to each other and limit the emitted/received light, and may include apertures determining the viewing angle and aligning them with a fluid container or (in this example) a flow pathway. A transparent chamber may be included with a cylindrical profile in which the fluid is placed or flows through, as illustrated in FIG. 15A and the end view shown in FIG. 15B. The fluid chamber includes a fluid access point for an integrated electrical sensor element such as that described in above (e.g., and shown in FIG. 13A).

The combination of the electrical sensors for determining the complex admittance producing a total of 12 measurement channels (e.g., six unique pairs of electrodes measuring both in-phase and quadrature components) with the optical system producing up to 6 measurement channels in this design produces a set of 18 independent measurements that are used to produce a unique pattern for each compound measured. The sensor system or array can be applied to the benchtop measurement of drugs in an area in which they are being prepared such as a pharmacy. The measurement and identification of the drug being prepared will validate it for the correct drug, correct concentration, and correct formulation, as mentioned above. In operation, both the electrical (admittance spectroscopy) and the optical information may be provided to the processor and used to determine the components of the solution.

Although many of the variations described herein use non-destructive sensing techniques such as low-power admittance spectroscopy, which will not alter the compounds, sterility or efficacy of the medical solution being tested, destructive drug sensing methods or sensors may also be used, particularly in embodiments such as the benchtop variations described above. Destructive techniques may be used in addition to or in conjunction with the complex admittance methods, devices and systems described above. In contrast to inline IV infusion monitoring, in pharmacy environment the identification process can be destructive or adulterating to both the sample and the sensor. This expands the list of applicable techniques or modalities that may also be used to include: an array of chemically modified sensing sites or surfaces, with which drug molecules of interest react or bind to and the product of such reaction or binding is detected optically, by color change, electrically or by resonator-based techniques, voltammeric or amperometric techniques, cyclic voltammetry, where the molecules and ions in the solution are subjected to electrically induced redox reactions, from which unique cyclic voltammograms can be recorded and used for identification of species involved.

The solutions of drugs can be subjected to electric current to produce electroluminescence and collected spectra can be used for drug identification. In addition the solutions of drugs can be subjected to ultrasound of sufficient intensity to produce sonoluminescence and collected spectra can be used for drug identification. An electric arc can be generated in the drug solution to produce light, which spectra can be used for drug identification. Other destructive techniques producing characteristic signals may include injecting a drug solution into flame, which spectra can be used for drug identification. The solutions of drugs can be subjected to microwave field of sufficient intensity to produce light and collected spectra can be used for drug identification In some variations, a miniature heater/thermometer can be used to measure boiling point of the solution and use it as an additional data for drug identification. Thermally-induced chemical reactions, turbidity, precipitation or fractionation of solution components at a function of temperature can be used for drug identification Another mode of admittance sensor operation may include invocation of the electroosmotic flow in the fluid under test. An electro osmotic flow creates motion in stagnant fluid or additional convective flow in the flowing fluid that promotes fluid exchange and replacement in the vicinity of or at the sensor surface that eliminating or greatly reducing any non-uniformity in the fluid or fluid flow under test. The detailed description of the phenomenon can be found in the following publications: Gonzalez, Ramos, Green, Castellanos, and Morgan, "Fluid flow induced by nonuniform ac electric fields in electrolytes on microelectrodes. ii. a linear double-layer analysis," Phys Rev E Stat Phys Plasmas Fluids Relat Interdiscip Topics, vol. 61, no. 4 Pt B, pp. 4019-4028, April 2000; Green, Ramos, Gonzalez, Morgan, and Castellanos, "Fluid flow induced by nonuniform ac electric fields in electrolytes on microelectrodes. i. experimental measurements," Phys Rev E Stat Phys Plasmas Fluids Relat Interdiscip Topics, vol. 61, no. 4 Pt B, pp. 4011-4018, April 2000; and N. G. Green, A. Ramos, A. Gonzalez, H. Morgan, and A. Castellanos, "Fluid flow induced by nonuniform ac electric fields in electrolytes on microelectrodes. iii. observation of streamlines and numerical simulation." Phys Rev E Stat Nonlin Soft Matter Phys, vol. 66, no. 2 Pt 2, p. 026305, August 2002.

In any of the variations described herein, the systems may include a mixer or agitator before the sensor, in order to homogenize the fluid composition seen by the sensor(s). As mentioned above, mixing may be particularly useful in the benchtop examples described herein, and may also be useful where the aqueous solutions include material suspended in the solution.

Mixing of the test solution (e.g., an IV solution) before it is probed by the sensor array may improve measurement accuracy. For example, the admittance sensors invoking electroosmotic flow described above may benefit from such additional mixing. Any appropriate mixer or method of mixing may be used. For example, a static fluid mixer such as that described in U.S. Pat. No. 3,286,992 may be used, for example, between an injection port and the sensor. In variations in which the sensor(s) are arranged downstream of an injection port, any non-uniform concentration profiles of the injected bolus in a carrier fluid in the vicinity of the sensor may be either taken into account via sensor calibration or physically eliminated at the point of measurement, including the use of a mixer. In addition, one or more IV fluid filters (e.g., U.S. Pat. No. 4,601,820, and U.S. Pat. No. 5,992,643) may be used. Such filters may include woven wire filter fabric with coarse mesh that brakes and randomizes flow path, and may also be useful for mixing instead (or in addition to) a dedicated static mixer. An active mixer may also be used. For example, the system may include a mixer that uses ultrasonic transducer such as a piezoelectric actuator that is located upstream from or near the sensor(s) or is integrated into the sensor assembly or substrate.

In one example of an admittance spectrographic system that includes another sensing modality, a system using a disposable, multiparametric sensor element includes optical measurement channels and admittance sensors and a data acquisition and processing system. This system measures a sample of a drug or other compound, acquires a set of multiparametric sensor data and matches the patterns generated in the sensor data to previously obtained signatures of drugs.

As mentioned, the optical data collected as part of the system may include the refractive index and/or the absorption from at least one, but preferably 2 or more wavelengths. The sensor elements (which may be probes, arrays, measurement cells, or the like), may include a housing that places sensor elements in contact with the fluid to be tested. In some variations, an optical pathway is included within the sensor element for measurement of optical parameters such as refractive index and absorption, as illustrated in FIGS. 15A and 15B. For example, a pathway through the sensor housing may include an injection molded optical windows for optical access to the fluid. Examples of optical sensors may include Light Emitting Diode (LED) sources and photodiodes and/or phototransistor detectors or any other applicable configurations. Optical sources consisting of solid state LED devices may have target optical wavelengths that can range from 250 nM to 1500 nM. For example, sources at 375 and 900 nM have used in a bench prototype. Other variations may incorporate sources and detectors for additional wavelengths in the range from 250 to 1500 nM or beyond to provide additional data channels.

Systems including optical sensors may use broad band emission LED sources, such as white LEDs may be used with a set of detectors each incorporating a filter for a specific wavelength. For example, in some variations, two or more optical sensor channels that measure the drug's optical absorption at two or more different wavelengths. In some variations, two or more optical sensor channels measure a drug's refractive index at two or more wavelengths. Optical detectors are typically matched to the LED sources for the specific wavelength. Optical filters that are external or internal to the source and/or detector may be used.

Electronics for signal conditioning may be used in any of these examples, including the combined electrical/optical systems, as mentioned above. For example, signals may be conditioned by amplification (e.g., operational amplifiers, lock in amplifiers), impedance analyzers, current to voltage converters, buffers, filters, and the like. The signal processing may occur before, as part of, and/or after the data has been acquired. For example a data acquisition system may be used that includes: analog to digital converters, processors, specialized Application Specific Integrated Circuit (ASIC) circuits and Field Programmable Gate Array (FPGA) devices for specialized functions.

The processor, including the recognition logic may be adapted to interpret both the optical and the admittance data. Thus, both types of data may be use to compare obtained sensor patterns with known patterns to identify the drug and concentration.

Any of the systems described herein may also include or be compatible for use with automated sample preparation and loading of samples to be tested. For example, disposable test cells may be used. Robotic fluid handling may also be used, and the systems described herein may be compatible with robotic fluid handling. Any of these systems may be used for the application of drug preparation monitoring and validation, including monitoring of drugs in pharmacies, drug laboratories, factories and any other location where a measurement of the drug concentration and identity would be needed.

Thus, additional modalities, such as optical measurements, may be used to supplement the admittance spectroscopy measurements. During operation of the system described above, the LEDs may be switched on, one at a time while measurements are taken and then turned off. This avoids crosstalk between the channels, reduces heating from the LEDs and increases their lifetime.

The cylindrical nature of the flow path in the measurement cell may create a cylindrical lens with a fluid core and thus makes the transmitted light sensitive to both the refractive index as well as the opacity of the fluid at a the given wavelength of the source and detector. In this example, as well as the example shown in the sensor array of FIG. 13B-13D, the optical system provides an additional 4 data channels for sample identification by measuring at 4 different wavelengths of light.

By applying a time varying excitation to an optical source such as an LED or laser, the resulting optical stimulus will have a time varying characteristic. A frequency referenced detection system such as a lock-in may be applied to the optical detector signals to improve the detection by rejecting noise and spurious signals other than the excitation frequency. If this frequency or frequencies are chosen properly, interference from other systems may be minimized and the sensitivity of the technique improved over DC measurement techniques.

In some variations the sensor may be used as part of a cylindrical transparent measurement cell that allows simultaneous measurement of the combined effects of refractive index and absorption, as illustrated in FIG. 15A. Drugs may be measured in a cylindrical volume or measurement cell. Light emitting diode or other optical sources are configured to illuminate this cylindrical volume through a small aperture and in a direction perpendicular to the cylindrical volume's axis. A detector is located on the opposite side of the cylindrical fluid volume and aligned with the light source and the center of the fluid volume. The fluid properties of refractive index and absorption at the specific wavelength of the source used will affect the intensity of the illumination at the detector and thus the measured signal. Changes in refractive index will affect the focusing or defocusing of the light and impact the area of the detector illuminated and thus produce a signal proportional to the fluid refractive index. Any absorption will impact the total intensity and thus also affect the measured signal. By measuring with such sensors at 2 or more wavelengths, the absorption and refractive index effects may be separated. However, for the purposes of generating a set of unique sensor responses to produce a unique signature for a measured fluid, separation of these parameters may not be necessary.

Optical absorption can be simultaneously measured at multiple optical wavelengths spanning from infra-red to UV range. Absorption of specific wavelengths can be used to identify drug compounds in solution for compounds that have characteristic absorption bands. Supplying light that corresponds with an absorption region for a particular drug can be used to confirm the presence or absence of that material. The magnitude of the absorption can also be used for concentration determination. A multi-channel absorption system can have multiple different optical sources such as LEDs each emitting a different wavelength and associated with a separate detector or a single detector and a switching system to turn on each LED in a sequence and measure the signal from the single detector. Each different wavelength measured creates an additional data channel that may be analyzed and used for drug detection and identification.

Color detection may also be applied as a sensor modality. Many drug compounds in solution will exhibit a particular color spectrum due to absorption of some wavelengths of light. By applying light and detecting at multiple wavelengths, the solution color can be determined. The technique can be implemented using a 3 color led plus photodiode or photo-transistor or by applying white light and detecting the resulting color spectra after the light has passed through the fluid. A color sensitive detector chip such as the TAOS optical systems TS230D or similar may be employed. Alternatively, a set of red green and blue filters may be placed between the light source and detectors and from the 3 values measured, the color coordinates of the fluid determined.

Refractive index (RI) detection at multiple wavelengths may be used to separate refractive index effects from evanescent wave effects. By measuring the fluid refractive index at multiple wavelengths and comparing the results, it is possible to separate the signal resulting from the fluid refractive index from evanescent wave effects that are more sensitive to the fluid physical and chemical properties (evanescent wave sensors are described, for example, in P. Suresh Kumar et al., A fibre optic evanescent wave sensor used for the detection of trace nitrites in water; 2002 J. Opt. A: Pure Appl. Opt. 4 247-250, and Potyrailo, et al., Near-Ultraviolet Evanescent-Wave Absorption Sensor Based on a Multimode Optical Fiber; *Anal. Chem.*, 1998, 70 (8), pp 1639-1645; DOI: 10.1021/ac970942v). As an example, the detector can use a color sensitive IC chip such as the TCS230 from TAOS Optics to simultaneously measure the amplitude at multiple wavelengths and determine the absorption spectra or color of the solution.

Evanescent wave effects have been demonstrated to be sensitive to changes in a fluid media. Using an uncoated fiber optic as a sensor will measure evanescent wave effects as there is no layer between the reflecting surface and the liquid interface. This can be applied to fiber optics, as well as any other refractive index method that involves reflection changes from a media-fluid interface. The sensor can also be responsive to evanescent wave fluorescence effects in the fluid. Selective coatings can be applied to the optical interface to provide selection of specific materials in the fluid. Measurements can be done at a range of wavelengths from IR to UV and wavelengths can be chosen for specific absorption or fluorescence regions to identify specific fluids. This can be applied to the measurement and identification of IV fluids.

Flow Sensors

Any of the systems and devices described herein may also include one or more sensors for measuring flow. For example, a flow detector may be incorporated into a common sensor assembly as illustrated in FIGS. 13B-13D. The sensor assembly in this example includes patterned electrodes that form the electrical admittance sensors and the flow meter. A transparent substrate can also be used as an optical path and/or a transparent layer can be applied to the substrate to act as a waveguide for light. Alternatively, a fiber optic or other optical waveguide can be bonded to the substrate to provide a refractive index sensor.

Figure 16:
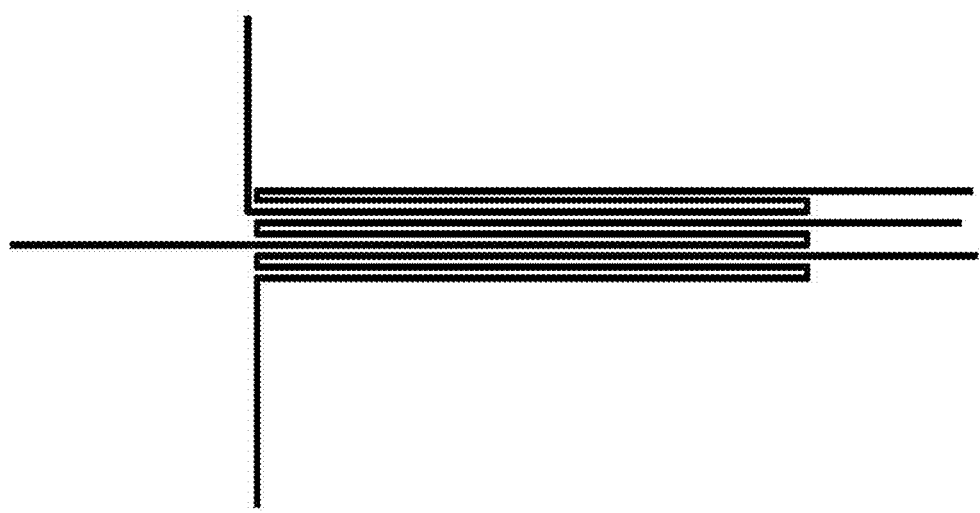
FIG. 16 illustrates one variation of a thermal anemometer flow sensor.

In some variations, the flow sensor is a hot wire anemometer flow detector. A thin film, hot wire anemometer is shown in the FIG. 16 (a variation of which is incorporated into FIGS. 13B-13D). This sensor measures flow by applying a very small amount of heat at one point in a flow stream, and from the change of temperature of a downstream sensor, the flow rate can be determined. In FIG. 16, thin film metal traces form 3 resistors. With one upstream, and one downstream of the central heated trace, this sensor may be used in a differential configuration to improve sensitivity and stability. It also has the capability of measuring the direction of the flow.

The design in FIG. 16 includes a thin film anemometer produced by metal deposition and lithography. It includes a set of 3 traces with dimensions of 1 mm long, 10 um trace width, 10 um trace-to-trace spacing.

In operation, the anemometer flow sensor electrodes may measure fluid thermal properties. For example, a hot wire anemometer such as that shown above may be used to measure fluid flow (see, e.g., H. Bruun, Hot-wire anemometry: principles and signal analysis. Oxford University Press, USA, 1995). In addition to or alternatively, if multiple wires or traces are available, the flow rate is known, it may be used to measure changes in the fluid thermal conductivity and/or heat capacity of the fluid. The basic idea of the hot-wire technique for the simultaneous measurement of the flow and the properties of fluid is that the usual calibration based on King's law can be extended to a fluid property (such as drug concentration) so that the "calibration constants" become calibration functions of the fluid property. Accordingly, if there are two wires available for measurements, two calibration functions, for which dependence of the fluid property is different, are present in King's law for each wire. The system of two King's equations then can be solved for two unknowns—the velocity and the fluid property with the accuracy determined by the wires implementation and signal to noise ratio of the measurement system. The calibration coefficients in King's law depend strongly on the thermal conductivity of the mixture and thus are sensitive functions of a drug's nature and concentration. A similar approach has been developed for the gas mixtures (e.g., P. Libby and J. Way, "Hot-wire probes for measuring velocity and concentration in helium-air mixtures," AIAA Journal, vol. 8, no. 5, pp. 976-978, 1970.

Figure 17B:
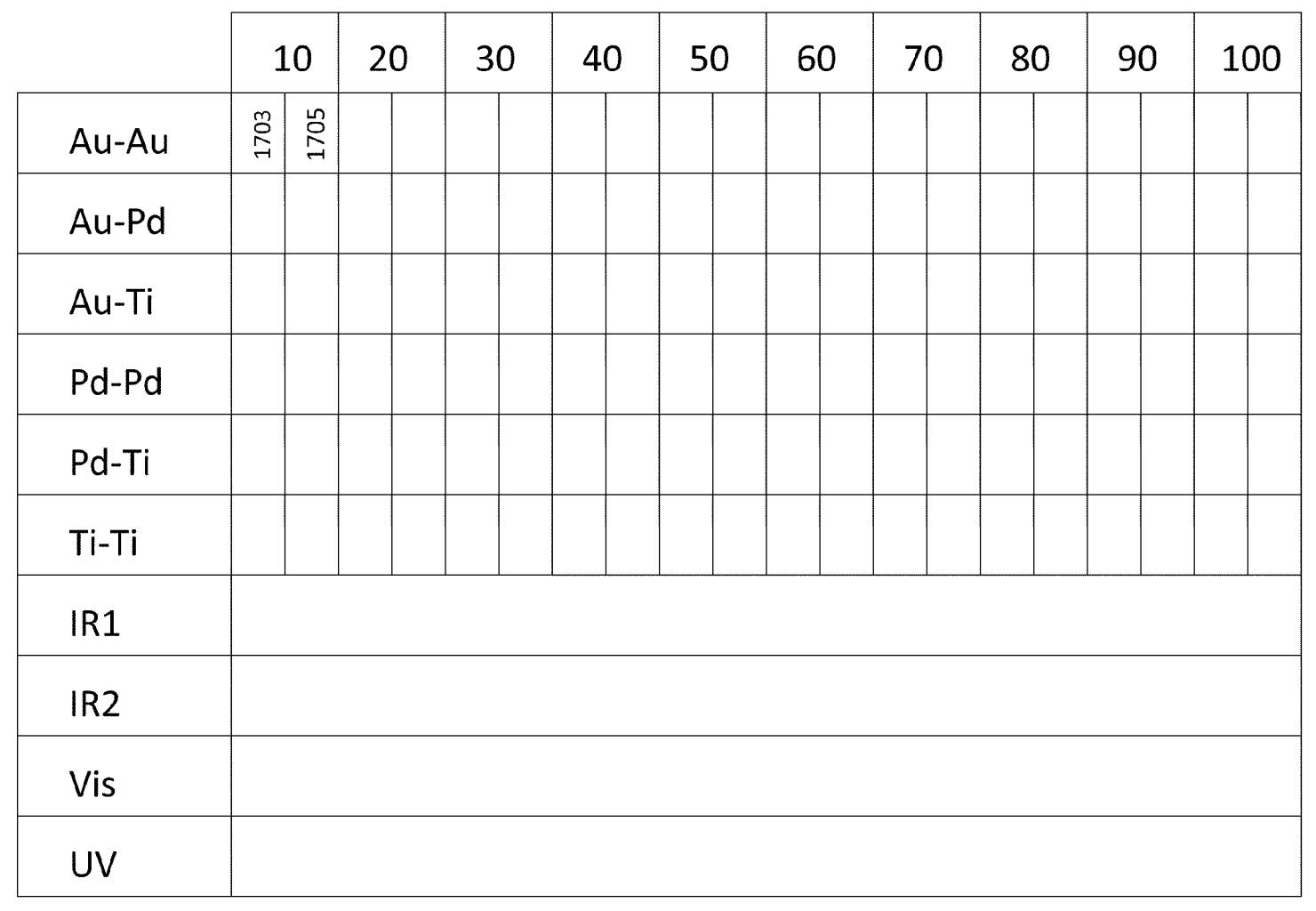

Operation of an Admittance Spectrographic Device for Determining Fluid Composition In operation, any of the variations described herein may, generate a fingerprint comprising the complex admittance data, as well as any additional data measured from the fluid. The fingerprint is typically a data structure that may be through of as an array, although it does not have to be arranged as a matrix. Because the fingerprint will be compared to a library of known values (which may also be considered known fingerprints), the organization of the data within the fingerprint may be stereotyped in format. For example, FIG. 17A conceptually illustrates one variation of an admittance spectroscopy fingerprint having 120 electrical channels, and thus at least 120 data points. This fingerprint is particularly useful for systems having, for example, six unique pairs of electrodes. As described above, electrode pairs are unique when at least one of the electrodes in the pair presents a different fluid-contacting surface compared to fluid contacting surfaces on the other pairs (e.g., the composition or geometry of the fluid-contacting surface of the electrode is different). In FIG. 17A, the visual representation of the fingerprint data structure is indexed online one side by the electrode pair, and six unique combinations of electrodes are used: Au—Au, Au—Pd, Au—Ti, Pd—Pd, Pd—Ti, and Ti—Ti. Ten different frequencies are examined using each electrode pair, as indexed horizontally: 10, 20, 30, 40, 50, 60, 70, 80, 90, and 100 kHz. As mentioned above, any appropriate frequency may be examined. In some variations, additional parameters may also be varied (and could be visualized as additional dimensions when represented as an array), including a DC offset, power applied, etc. For each electrode, and at each frequency, both the in-phase 1703 and quadrature 1705 components of the complex admittance are determined. Thus, there are 120 different parameters. Other variations of admittance spectroscopy fingerprints may include more or fewer parameters, and may include additional parameters measured from other modalities, including any of those described above. For example, FIG. 17B illustrates a representation of one variation of a fingerprint data structure that includes four optical channels (IR1, IR2, Vis, UV). The four optical channels may hold coupled absorption and refractive index data.

Each of the parameters measured (or a subset of them) may be sampled multiple times and the collection of values manipulated to provide the value entered in to the fingerprint (e.g., the mean, average, peak, minimum, median, etc. may be used).

An exemplary device such as the one shown in FIG. 9 was constructed as a prototype, and used to both generate known sample fingerprints, and to examine unknown fluid samples to determine the identity and concentrations of the samples.

In this exemplary device, a set of impedance sensor channels were similar to those shown in FIGS. 13B and 13D. With this set, the following electrical (complex admittance) measurement channels are available: Au—Au, Au—Pd, Au—Ti, Pd—Pd, Pd—Ti, and Ti—Ti.

In the prototype, the complex ac response may be separated into real (in-phase) and imaginary (or quadrature) signals by a lock-in amplifier thus providing two data channels from each metal electrode pair and giving a total of 12 impedance channels. The complex ac impedance response of these electrode channels were measured using a lock in amplifier in current mode operating at a range of frequencies (10, 20, 30, 40, 50, 60, 70, 80, 90 and 100 kHz).

In addition to the complex admittance measurements, in some tests optical measurements were also made. For example, in some tests a fluid refractive index sensor was used. In one variation, the RI sensor operated at 910 nM and was constructed from an LED source and photo transistor detector coupled through a sharply bent section of optical fiber that is immersed into the IV fluid. In addition, a fluid optical absorption sensor was used, operating at 375 nM consisting of a UV LED source coupled through the IV fluid flow, perpendicular to the flow direction, to a photodiode detector. The optical source LEDS are driven by adjustable current sources at levels of approximately 1-3 mA. This provides low level light intensity to avoid detector saturation. At this drive level, the optical intensity applied to the fluid will be at most, a few microwatts per square cm.

In the exemplary device described above, the lock-in amplifier used has X and Y output voltages that are measured by a National Instruments sbRIO device and plotted in volts. The excitation voltage is set at $V_x=21.21$ mV RMS (30 mV-amplitude), and the complex admittance between the sensor electrode in reciprocal Ohms is calculated as $6.09 \times 10^{-4}$ (X=iY), where X and Y are chart values. The complex current density is approximately $1.83 \times 10^{-4}$ (X+jY) A/mm$^2$, where X and Y are chart values.

Figure 19B:
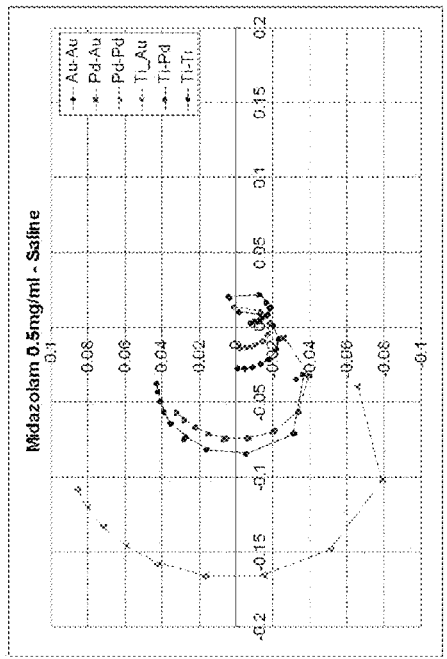
FIGS. 19A-19T show a graphical representation of the complex admittance fingerprints for some of the compounds listed in FIG. 18. The fingerprint is graphically shown as admittance spectroscopy data for each of six unique electrode pair combinations at 10 different frequencies for each of the six electrode pairs.
Figure 19D:
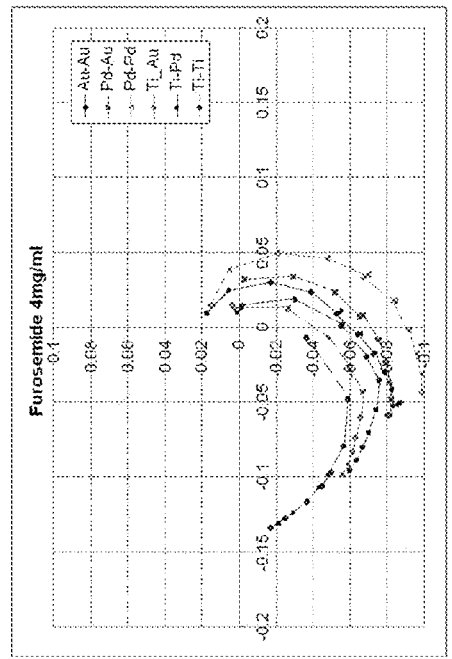
Figure 19A:
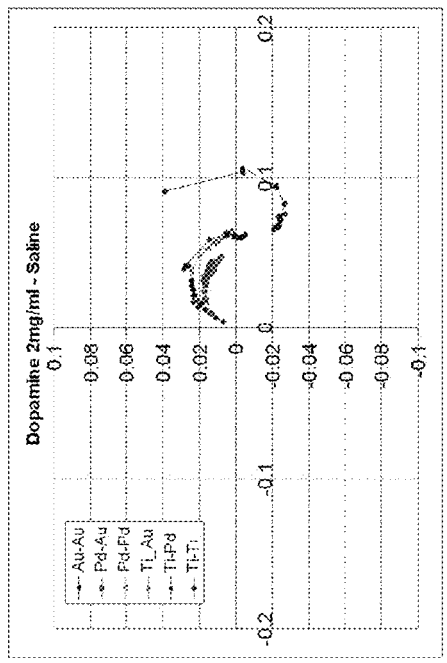
Figure 19C:
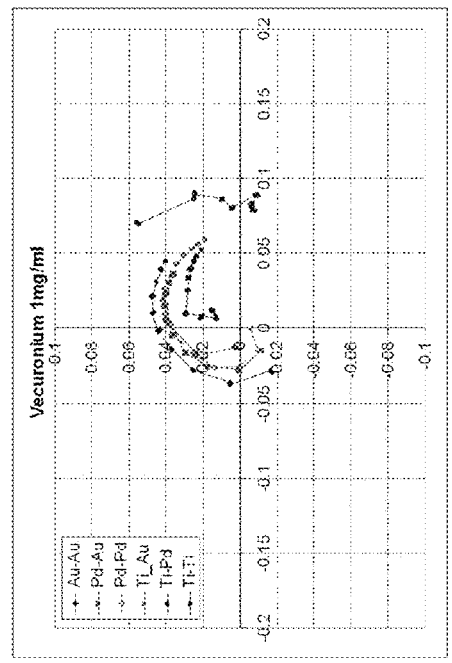
Figure 19E:
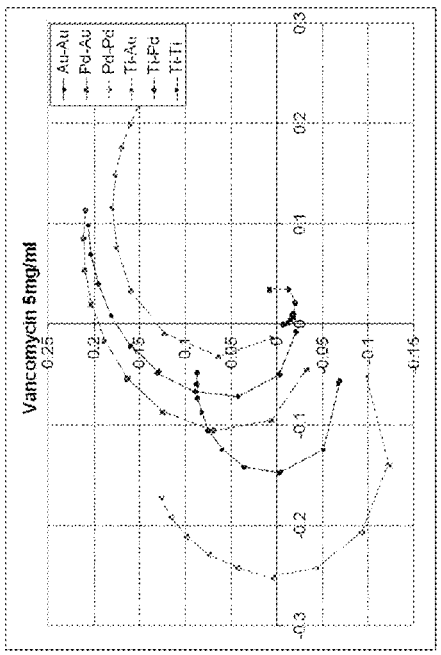
Figure 19F:
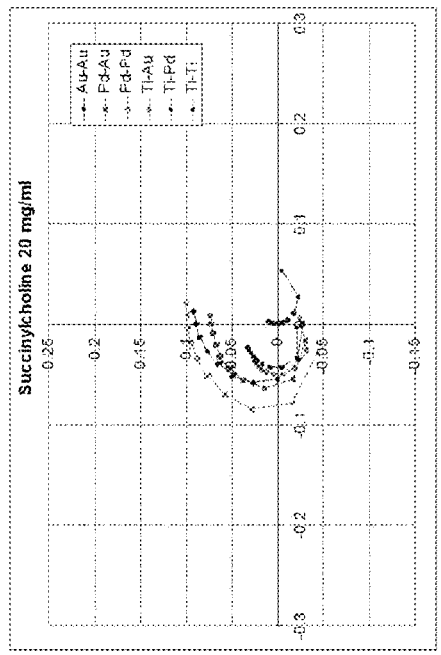
Figure 19G:
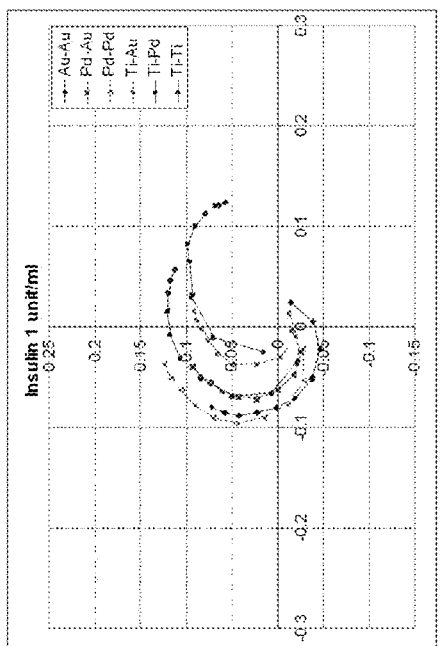
Figure 19H:
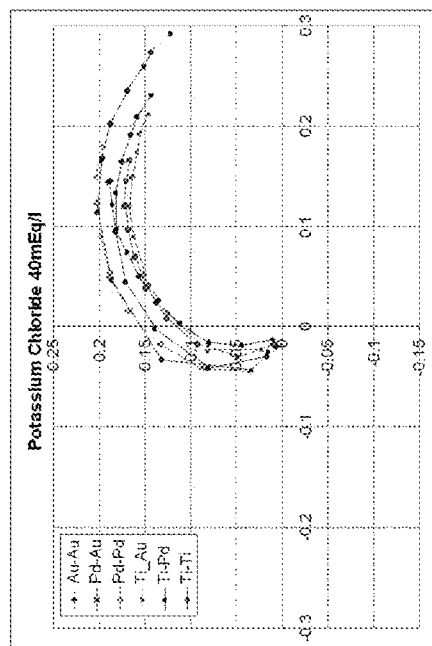
Figure 19I:
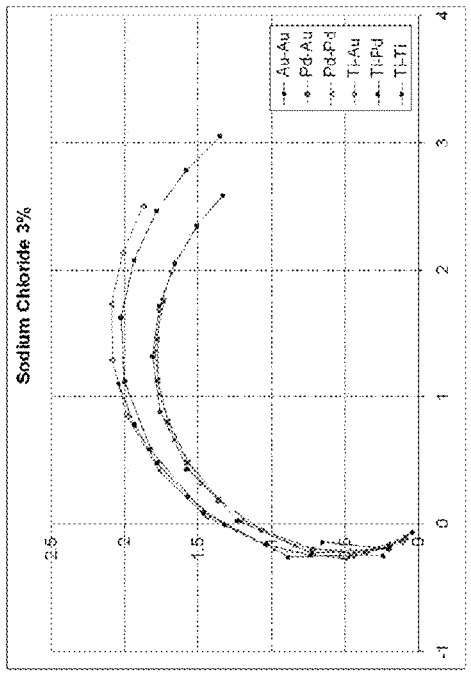
Figure 19J:
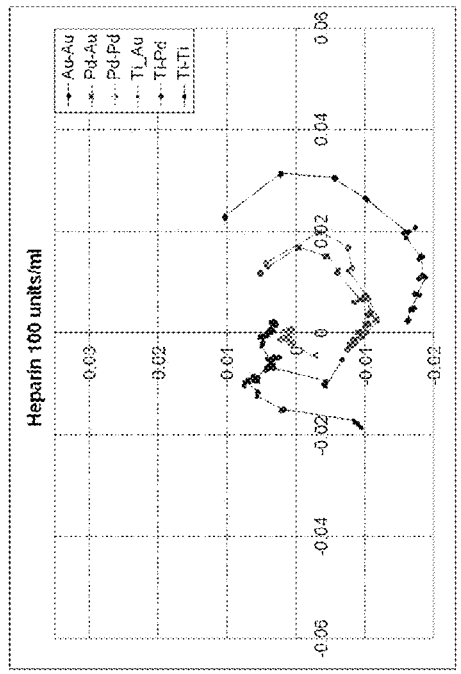
Figure 19K:
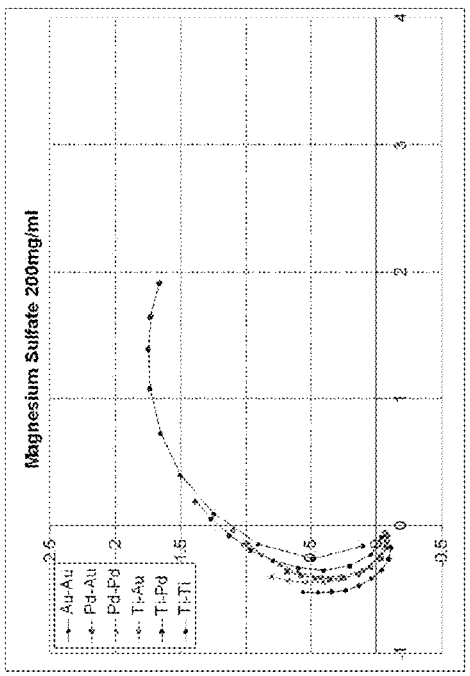
Figure 19L:
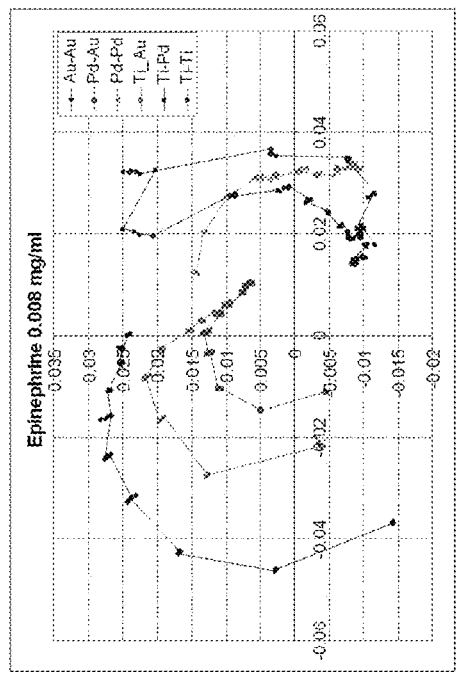
Figure 19M:
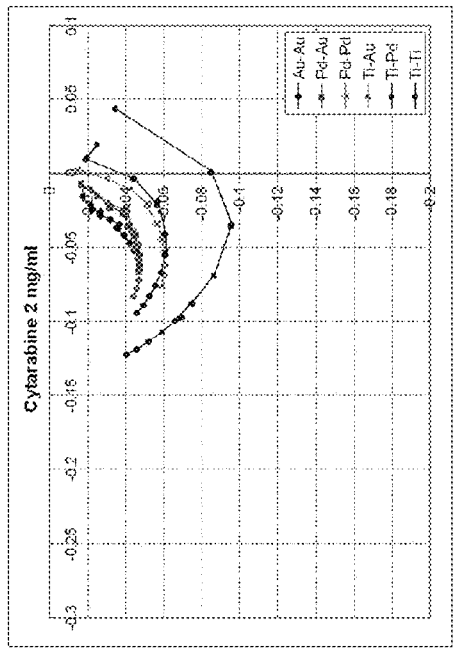
Figure 19N:
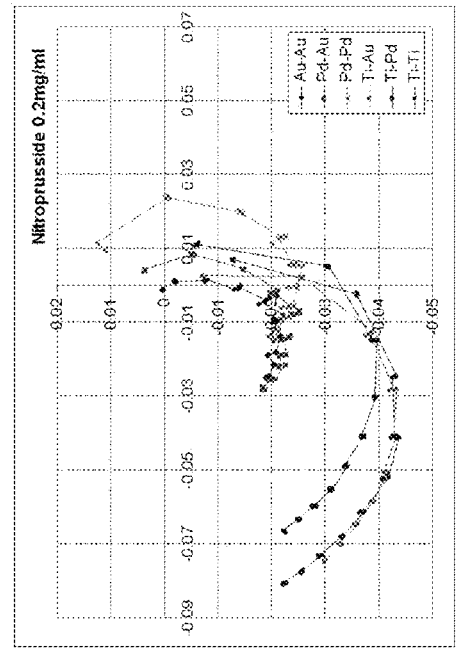
Figure 19O:
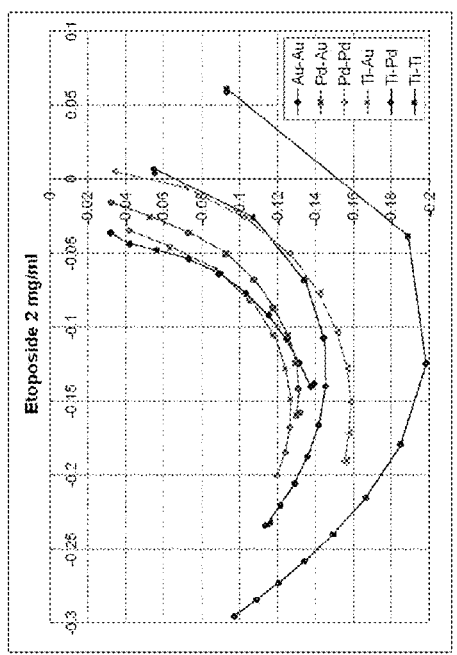
Figure 19P:
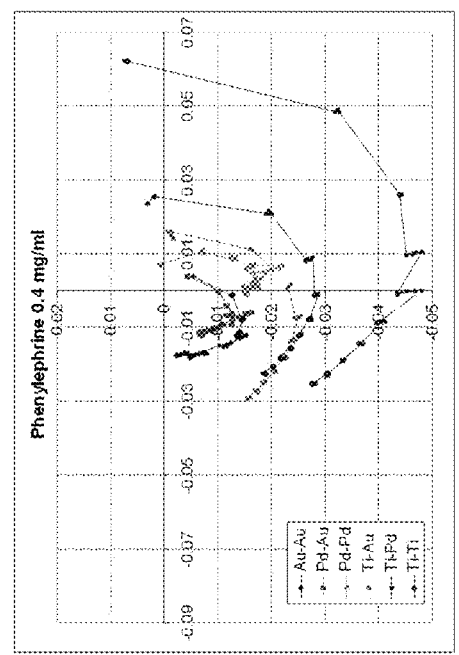
Figure 19Q:
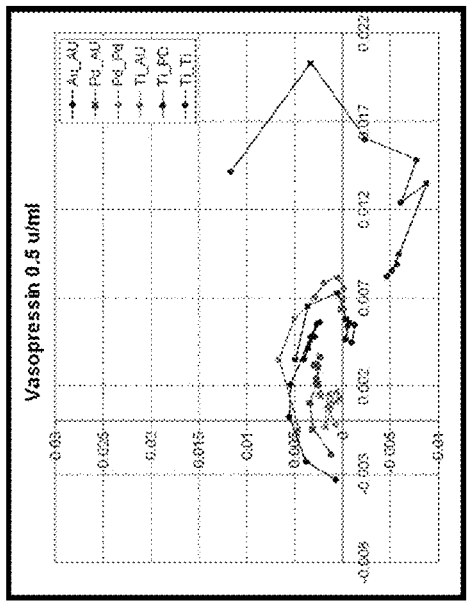
Figure 19R:
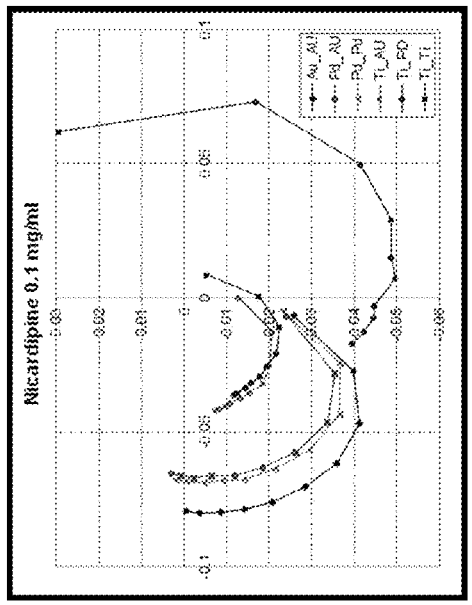
Figure 19S:
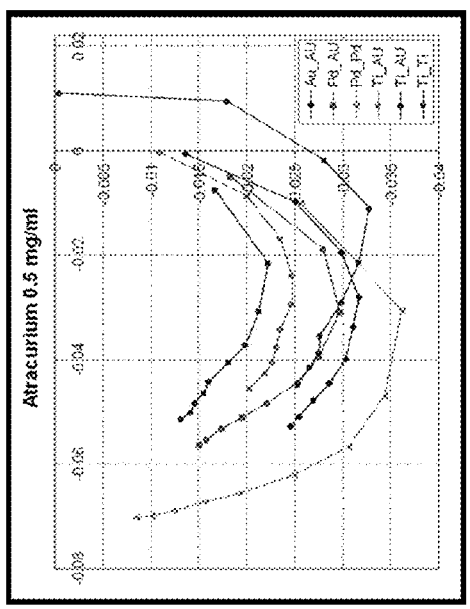
Figure 19T:
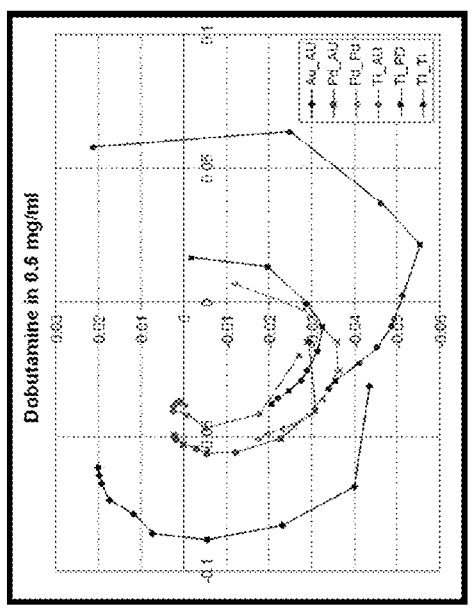
Figure 23A:
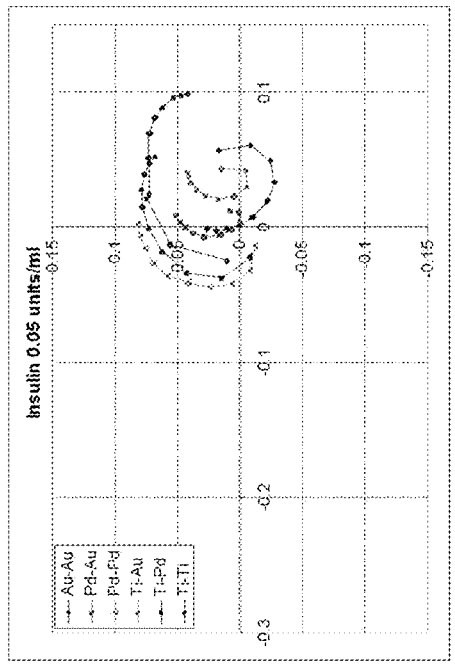
FIGS. 23A-23H illustrate admittance spectrographic fingerprints for increasing concentrations of Insulin (increasing from 0.01 units/ml to 30 units/ml).
Figure 23B:
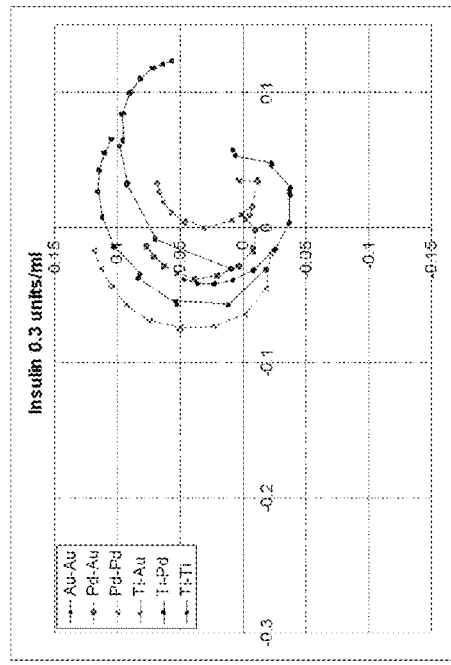
Figure 23C:
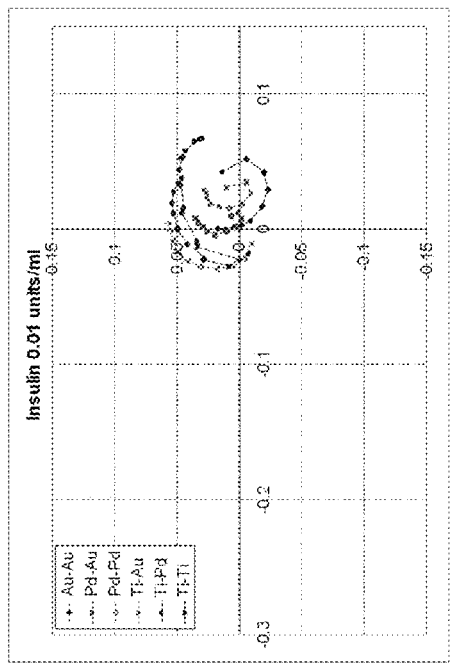
Figure 23D:
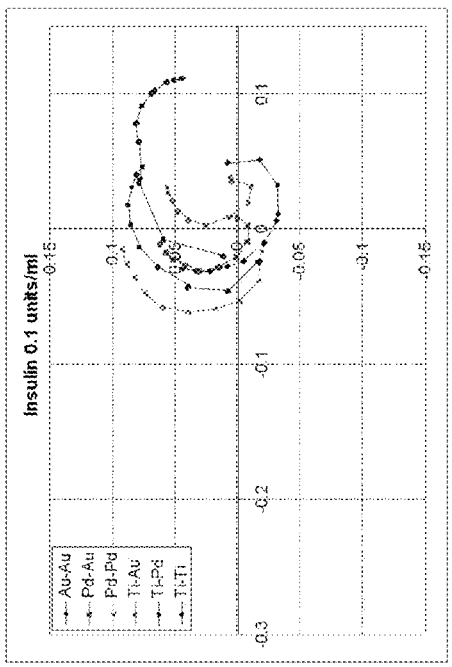
Figure 23E:
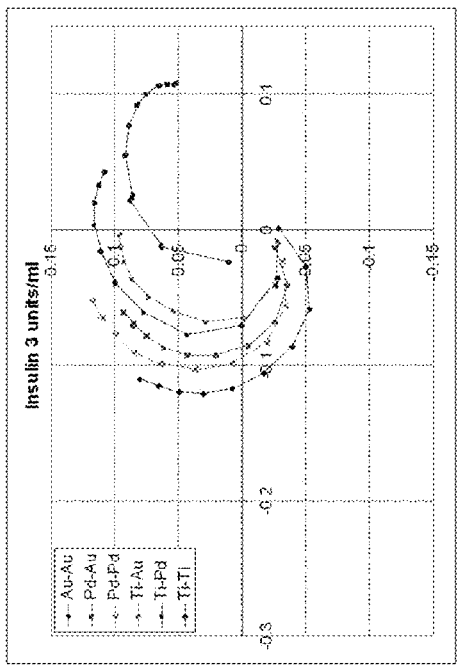
Figure 23F:
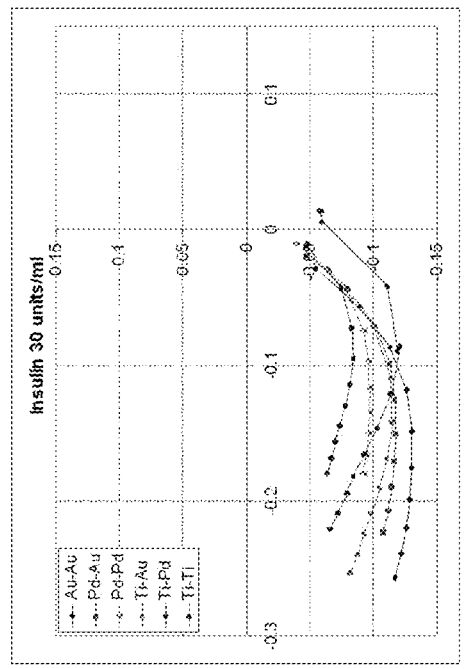
Figure 23G:
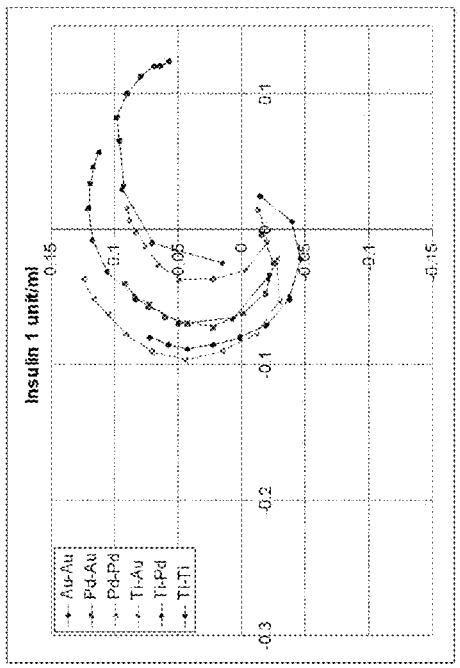
Figure 23H:
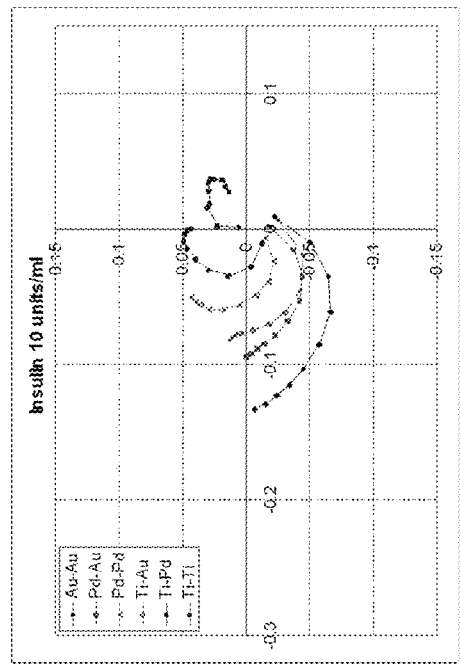
Figure 24A:
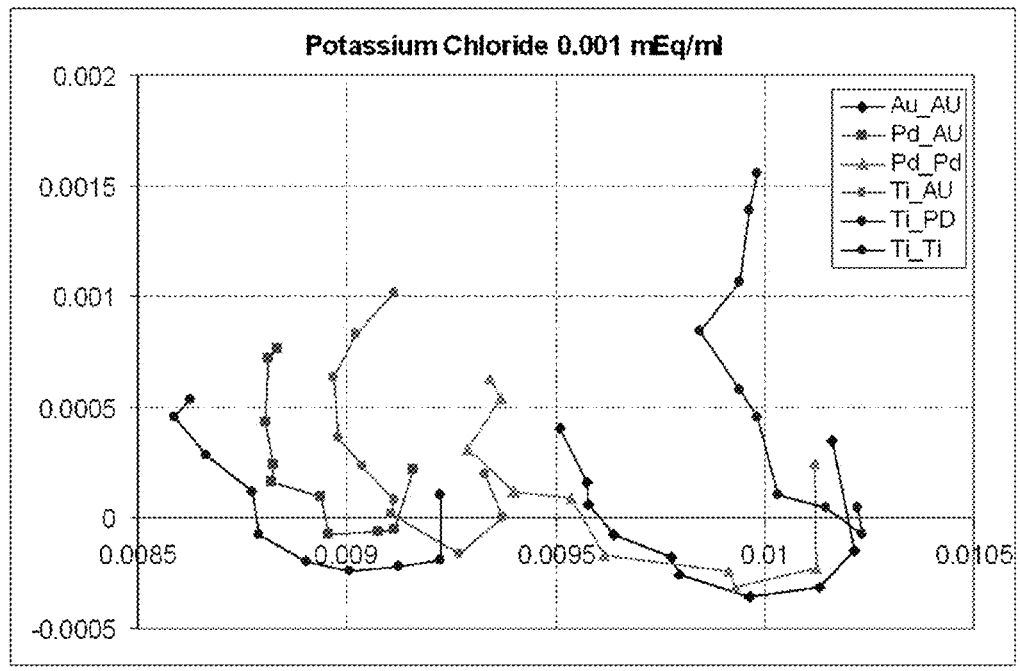
FIGS. 24A-24H show admittance spectrographic fingerprints for increasing concentrations of potassium chloride (from 0.001 to 0.8 Milliequivalent per mL).
Figure 24B:
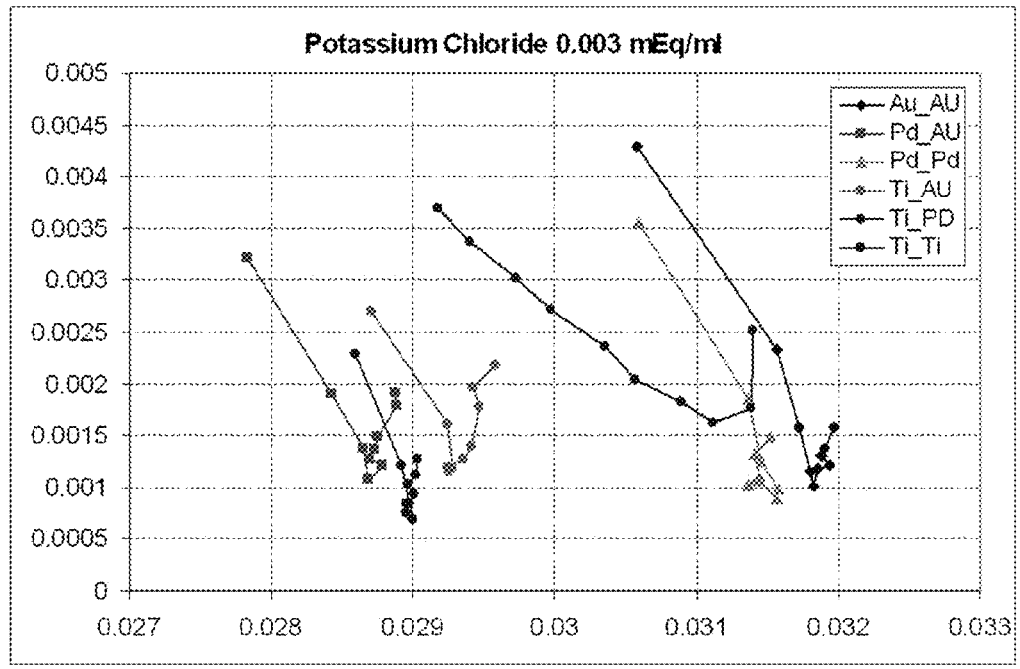
Figure 24C:
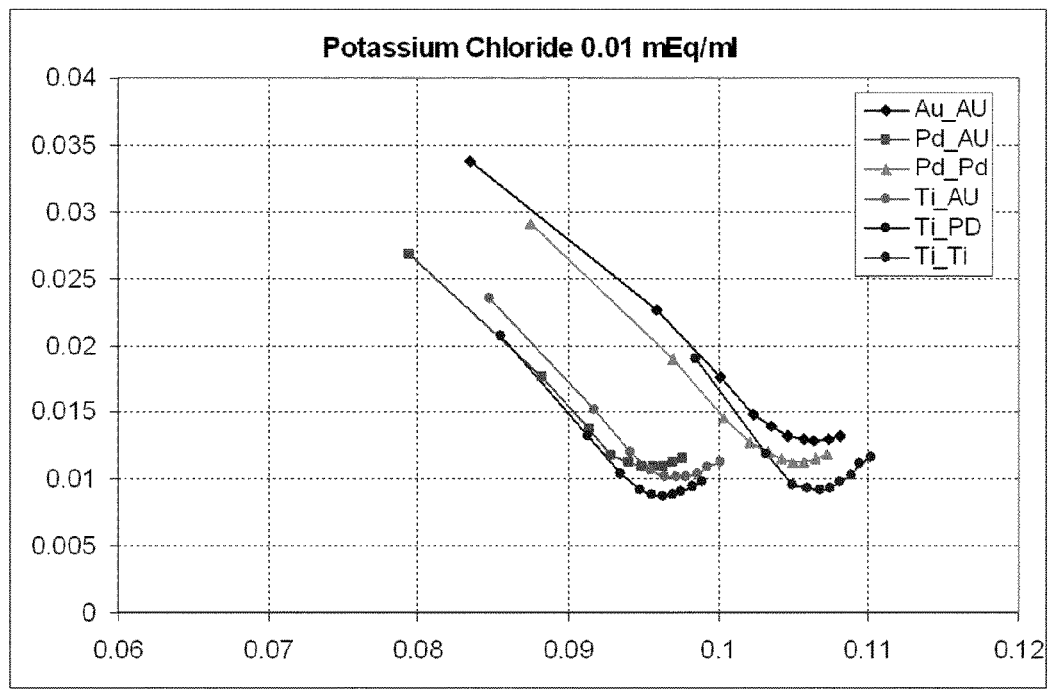
Figure 24D:
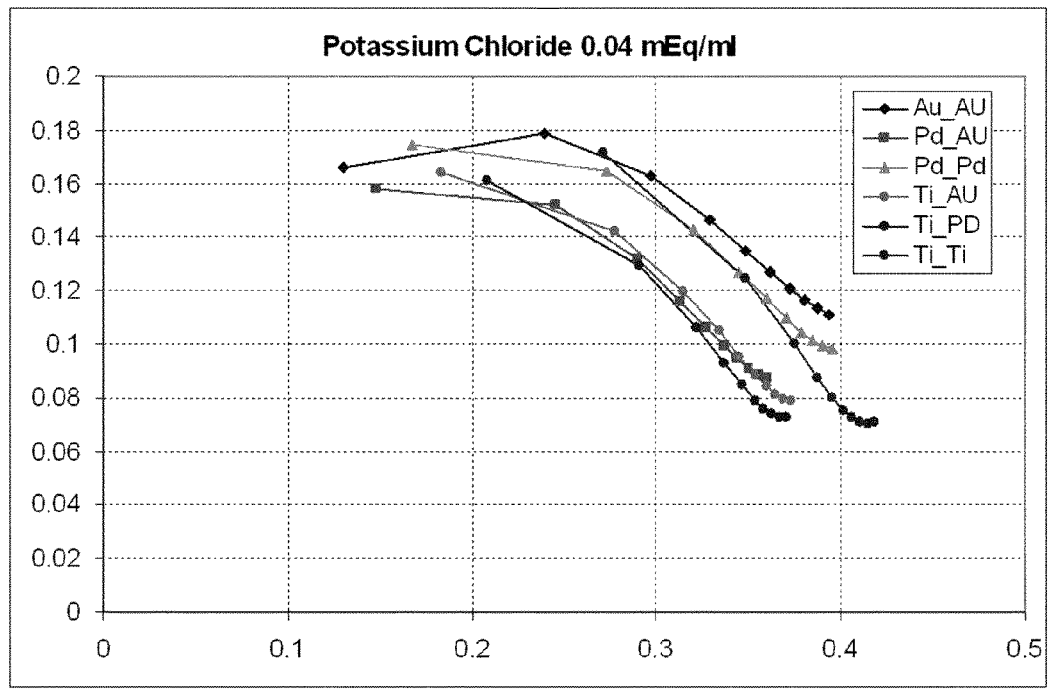
Figure 24E:
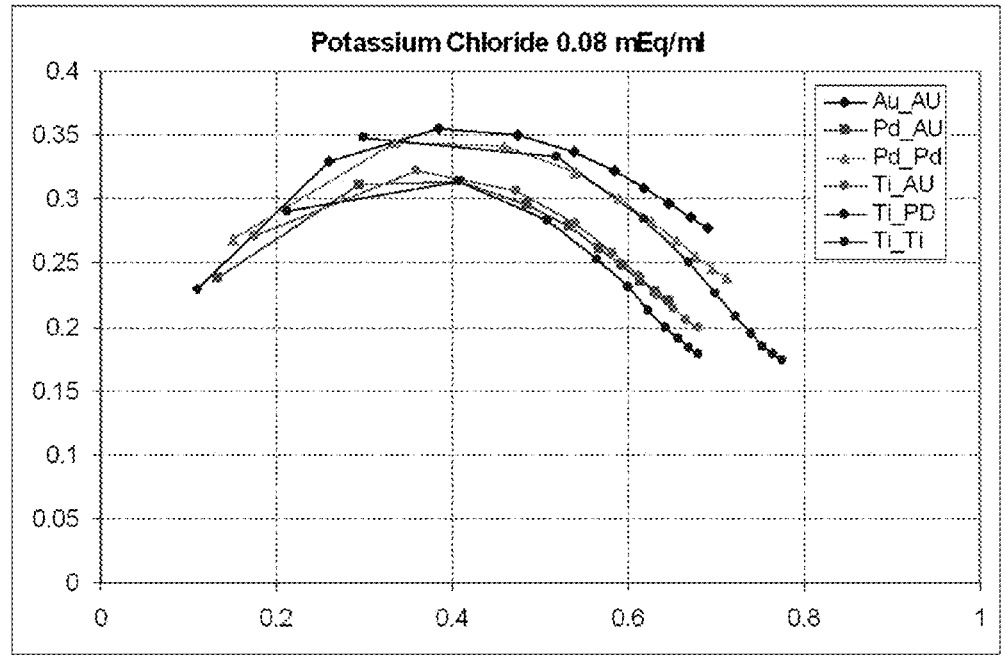
Figure 24F:
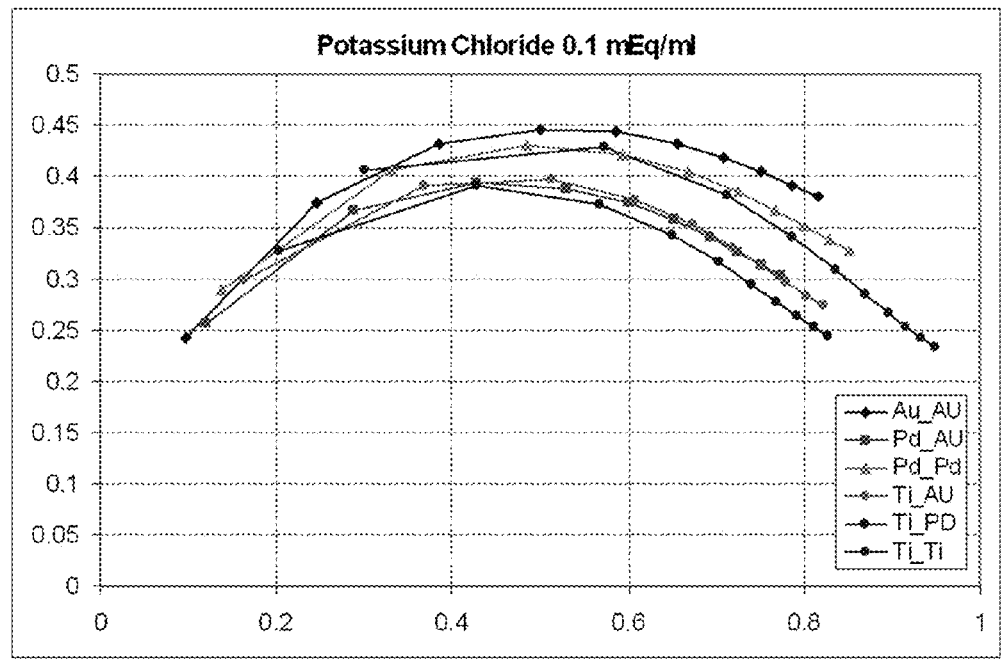
Figure 24G:
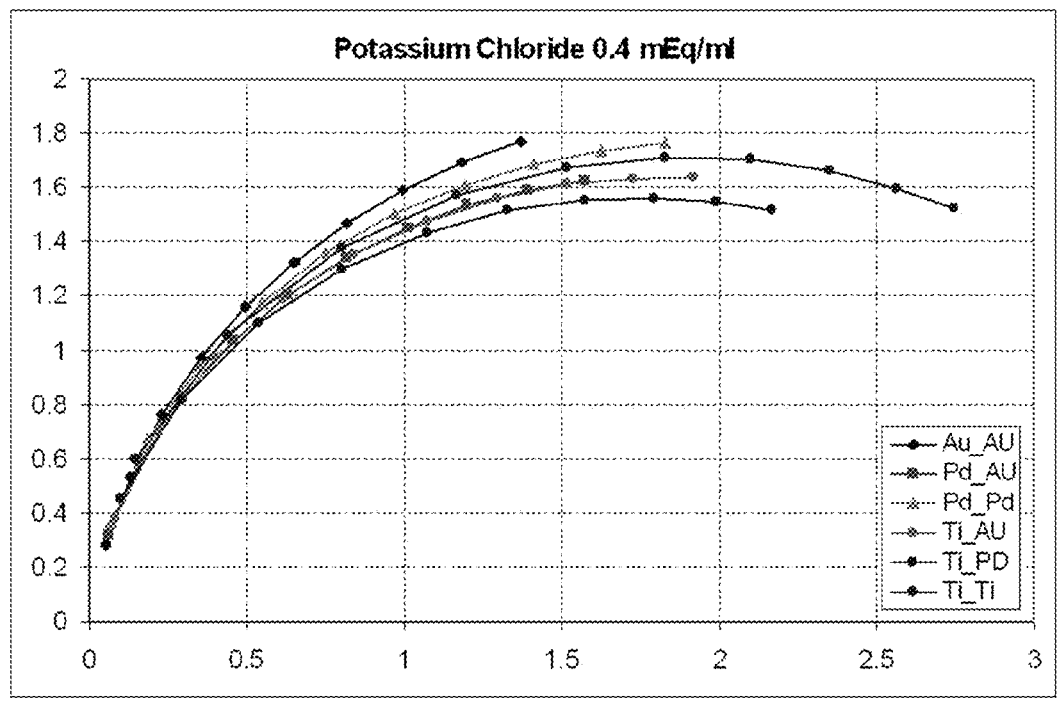
Figure 24H:
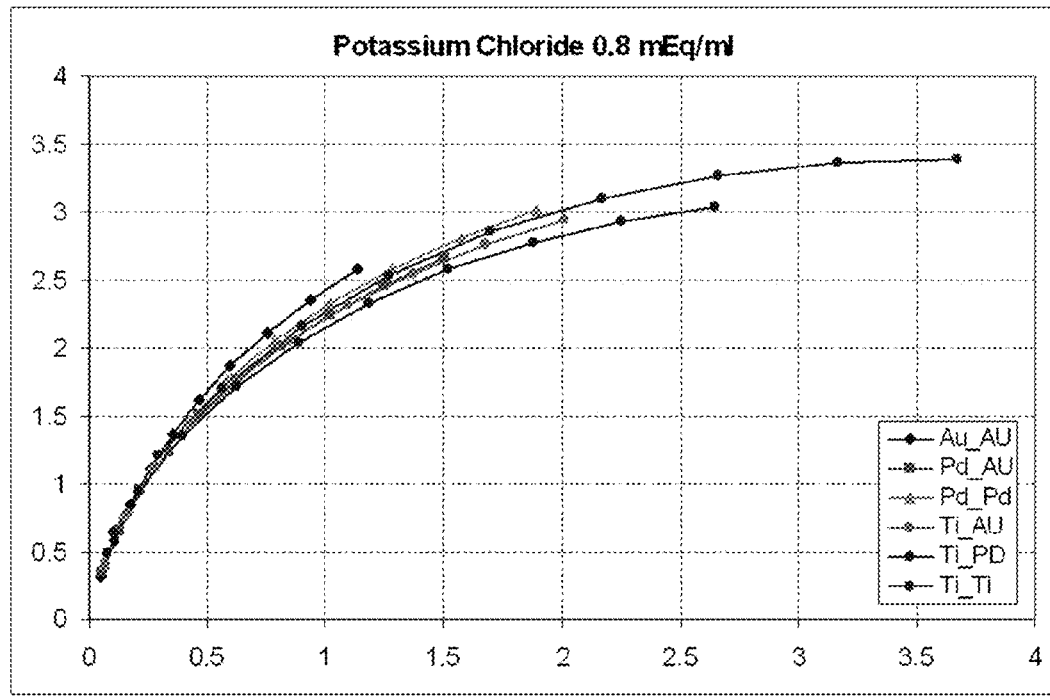

FIGS. 18A and 18B are tables listing drugs and concentrations that were examined using a prototype device. This list is not exhaustive, but is merely intended to illustrate a subset of the drugs initially tested. In addition, dose/concentration curves as well as drug combinations were examined. FIGS. 19A-19T illustrate admittance spectrograph fingerprints for solutions containing some of these compounds at known concentrations. These solutions were prepared in a biological carrier solution (e.g., normal saline), and the entire admittance spectrographic fingerprint was taken. In these examples, the complex cell admittance ($Y_0'+iY_0''$) was measured within a frequency range 10-100 KHz at 10 KHz steps, 5 times at every step for every electrode combination. An initial measurement was performed in pure 0.9% normal saline between all the electrode combinations and all spectra were stored (Saline reference spectra). The saline solution in the cell was replaced with a drug solution formulated in the same saline. The spectra $Y_1'+iY_1''$ between all of the electrode pairs were measured in the same way, and the saline reference spectra between correspondent electrode pairs were subtracted from the data: $(Y_1'-Y_0')+i(Y_1''-Y_0'')$. The cell was then filled with another drug solution and the subtraction procedure was repeated. In-phase values $(Y_1'-Y_0')$ were plotted along the X-axis and quadrature values $(Y_1''-Y_0'')$ were plotted along the Y-axis at each frequency step in arbitrary units, but on the same scale.

The in-phase versus quadrature curves for each unique electrode pair are shown in FIGS. 19A-19T, showing curves formed of the 10 different frequencies examined. As can be seen from the different traces, the patterns corresponding to each drug in solution is unique to the drug examined.

The shape of the admittance spectrographic curves may be used to distinguish even drugs that are closely related in structure and/or charge. For example, FIGS. 20A-20B show a side-by-side comparison of the structurally similar drugs Pancuronium and Vecuronium at identical concentrations. As can be seen from the graphs, the admittance spectrographic fingerprints of the two drugs are dramatically different. Similar comparisons were made between Epinephrine and Norepinphrine shown in FIGS. 21A-21B, and Morphine and Hydromorphone shown in FIGS. 22A-22B.

Drug concentration in solution also changes the admittance spectrographic fingerprint of the solution, as indicated by FIGS. 23A-23H, which shows the admittance spectrographic fingerprints for different concentrations of insulin from 0.01 Units/ml to 30 Units/ml in normal saline. The curves corresponding to each electrode pair independently and progressively change position (representing the in-phase and quadrature components of the complex admittance) as the concentration is increased or decreased. A similar family of curves was generated for different concentrations of potassium chloride in dextrose (D5W), as shown in FIGS. 34A-34H.

Figure 25A:
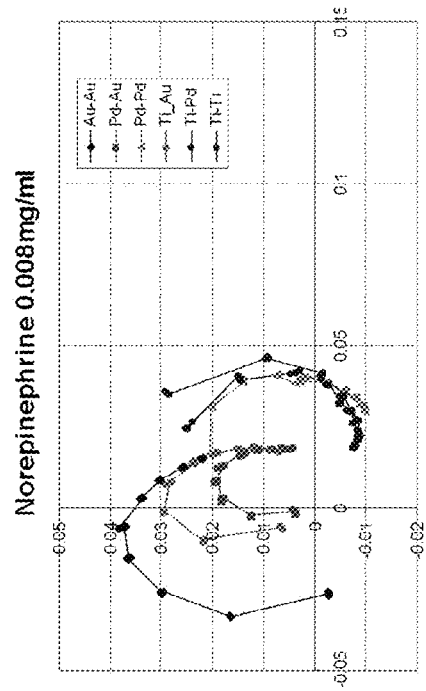
FIG. 25A shows the admittance spectrographic fingerprint for 2 mg/ml Dopamine.
Figure 25B:
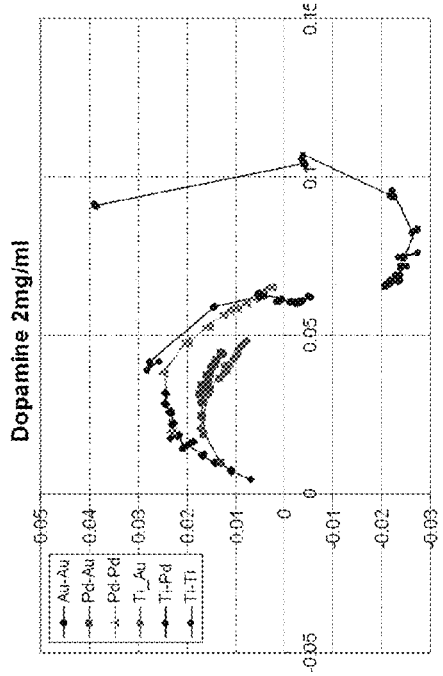
FIG. 25B shows the admittance spectrographic fingerprint for 0.008 mg/ml Norepinephrine.
Figure 25C:
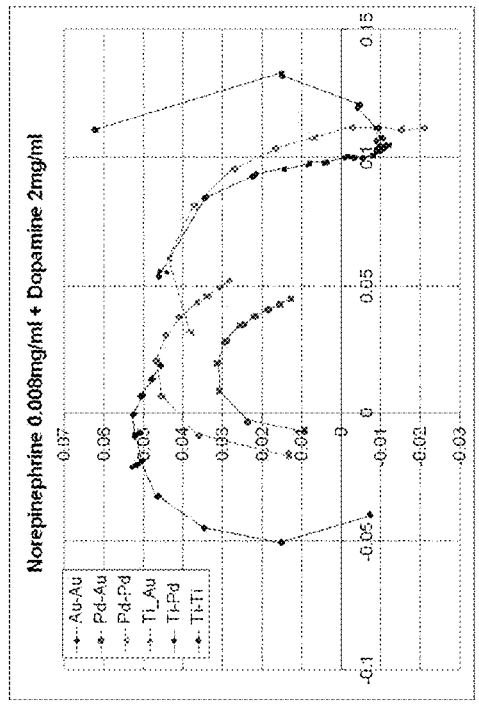
FIG. 25C shows the admittance spectrographic fingerprint for a solution of both 2 mg/ml Dopamine and 0.008 mg/ml Norepinephrine.
Figure 26A:
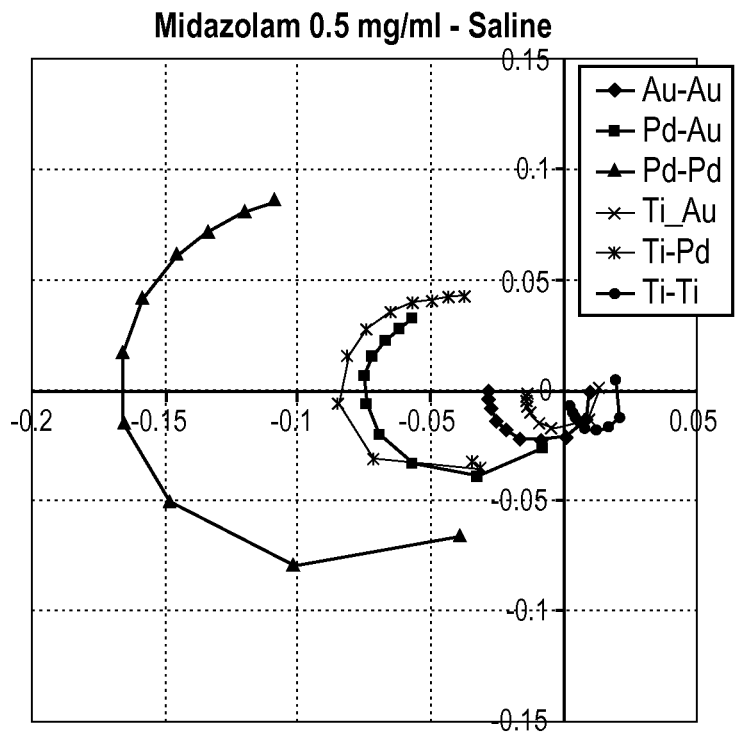
FIG. 26A shows the admittance spectrographic fingerprint for 0.5 mg/ml of Midazolam.
Figure 26B:
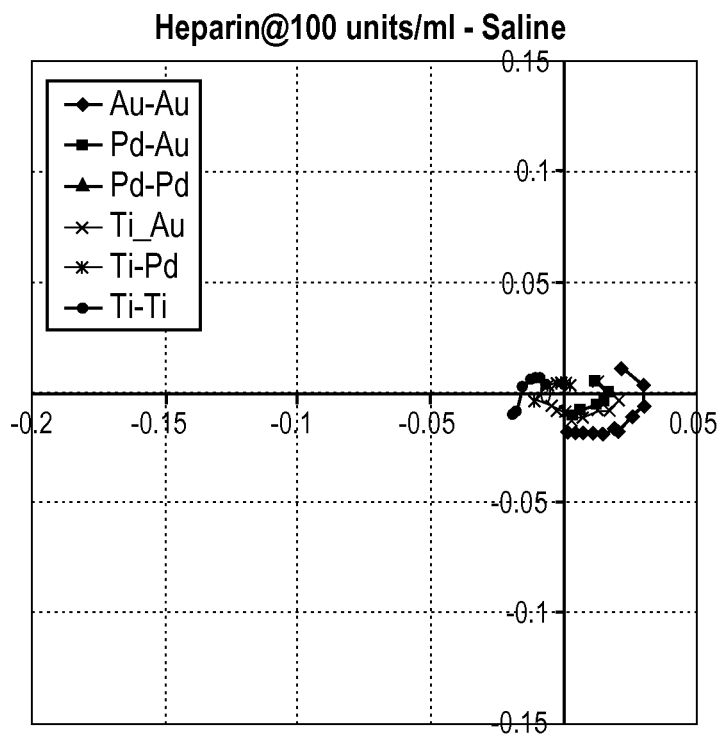
FIG. 26B shows the admittance spectrographic fingerprint for 100 units/ml of Heparin.
Figure 26C:
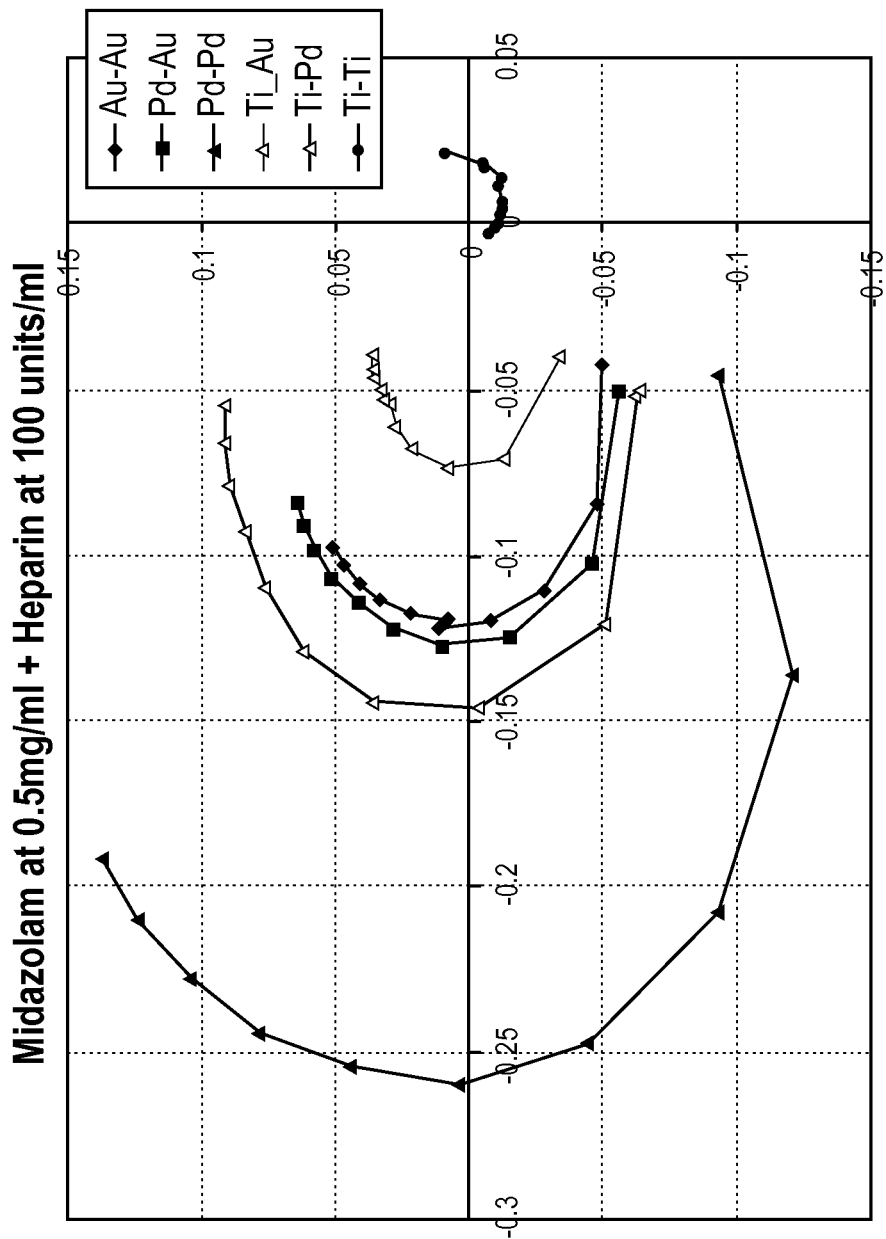
FIG. 26C shows the admittance spectrographic fingerprint for a solution of both 0.5 mg/ml of Midazolam and 100 units/ml of Heparin.

Mixtures of compounds, including drugs, also exhibit characteristic patterns of admittance spectroscopy. The resulting fingerprint is unique to the mixture composition and concentrations, even when compared to the same compounds alone. For example, FIG. 25A shows the admittance spectrographic fingerprint of Dopamine at 2 mg/ml, and FIG. 25B shows the admittance spectrographic fingerprint of Norephinephrine at 0.008 mg/ml. A mixture of 2 mg/ml of Dopamine and 0.008 mg/ml of Norephinephrine is shown in FIG. 25C, and has a completely unique pattern. FIGS. 26A-26C show another example of this, looking at Midazolam (0.5 mg/ml) and Heparin (100 units/ml), and a mixture of both at the same concentration.

Figure 30A:
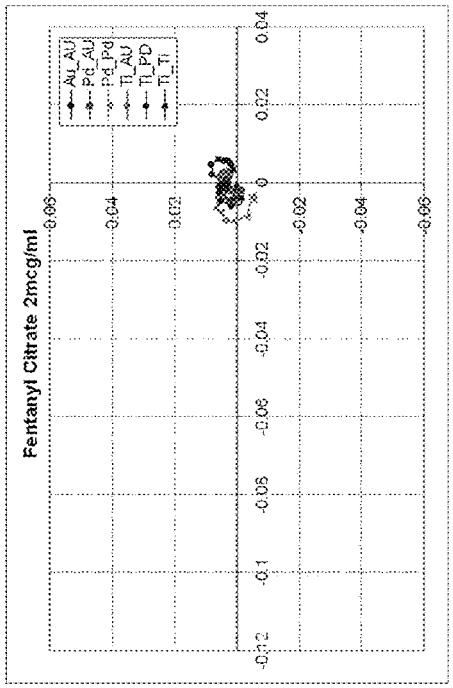
FIG. 30A shows a graphical representation of the admittance fingerprint for 0.1% Bupivacaine
Figure 30B:
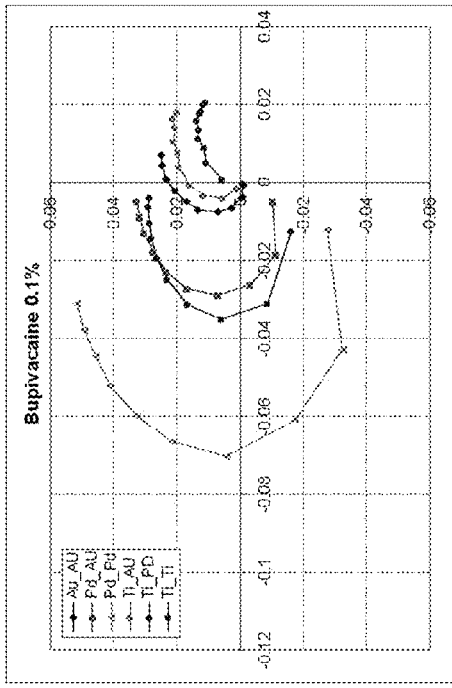
FIG. 30B shows a representation of the admittance fingerprint of Fentanyl Citrate (2 mcg/ml).
Figure 30C:
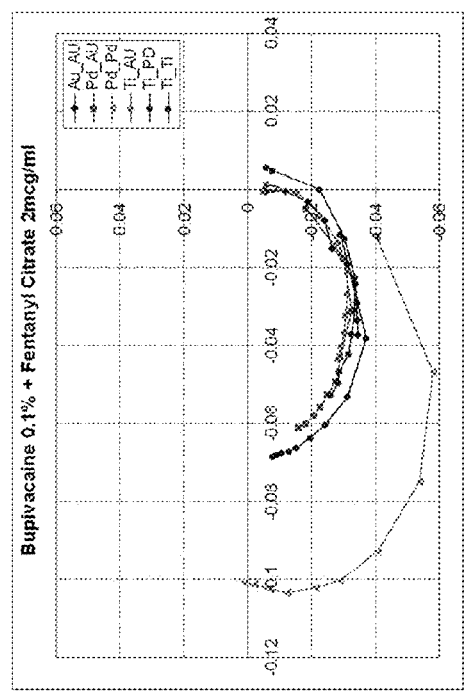
FIG. 30C shows the unique fingerprint of the combination of a mixture of Bupivacaine (0.1%) and Fentanyl Citrate (2 mcb/ml).
Figure 31B:
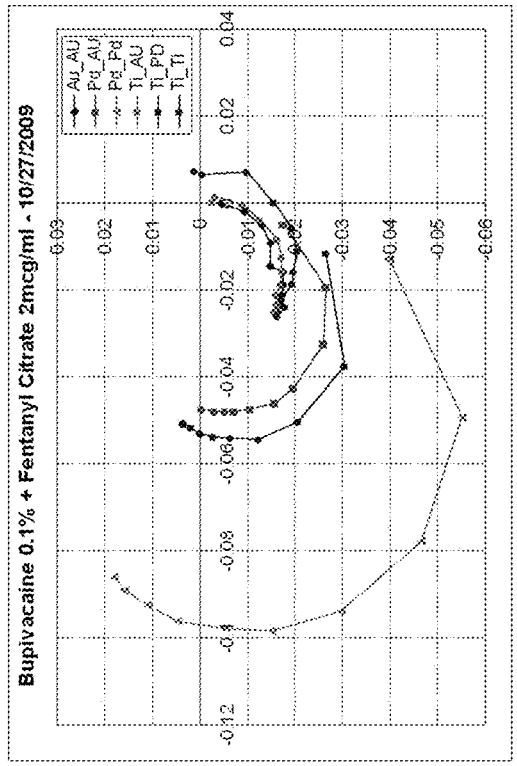
FIG. 31B shows the admittance fingerprint of an expired version of the same mixture.
Figure 31A:
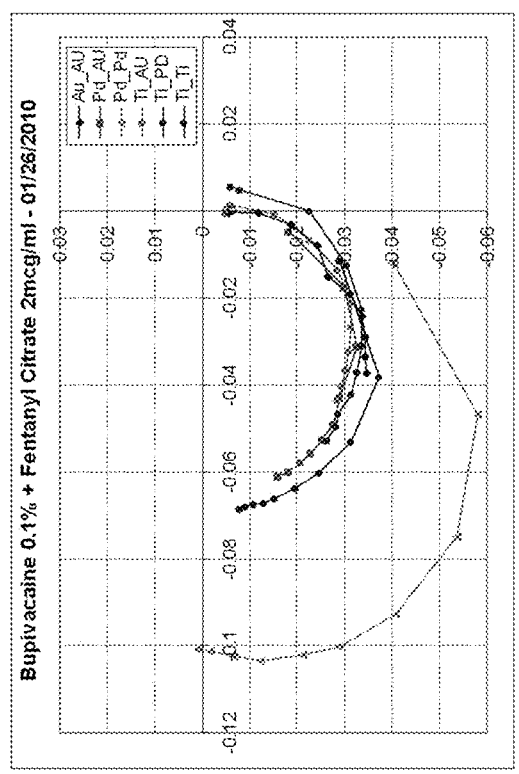
FIG. 31A is a graphical illustration of the admittance fingerprint of a "fresh" (freshly prepared, non-expired) mixture of Bupivacaine and Fentanyl Citrate in saline.

FIGS. 30A-30C illustrate another example, showing the mixture of two drugs used together in an epidural: Fentanyl plus bupivicaine. FIG. 30A shows a representation of the admittance fingerprint for 0.1% Bupivacaine and FIG. 30B shows a representation of the admittance fingerprint of Fentanyl Citrate (2 mcg/ml). FIG. 30C shows the unique fingerprint of the combination of a mixture of Bupivacaine (0.1%) and Fentanyl Citrate (2 mcb/ml). All of the figures are shown at the same XY scale. The same drugs can be use to illustrate the ability of the system to detect drug stability and/or adulteration. For example, FIG. 31A shows a representation of the admittance fingerprint for a mixture of Freshly prepared Bupivacaine (0.1%) and Fentanyl Citrate (2 mcg/ml). FIG. 31B shows a representation of the admittance fingerprint for a mixture of Bupivacaine (0.1%) and Fentanyl Citrate (2 mcg/ml) that is three days past the expiration date. The mixture in FIG. 31A was prepared on Jan. 26, 2010, two days prior to testing, and the mixture in FIG. 31B was prepared on Oct. 27, 2009, 93 days prior to testing. Both drug mixtures were tested on the same day.

Figure 27A:
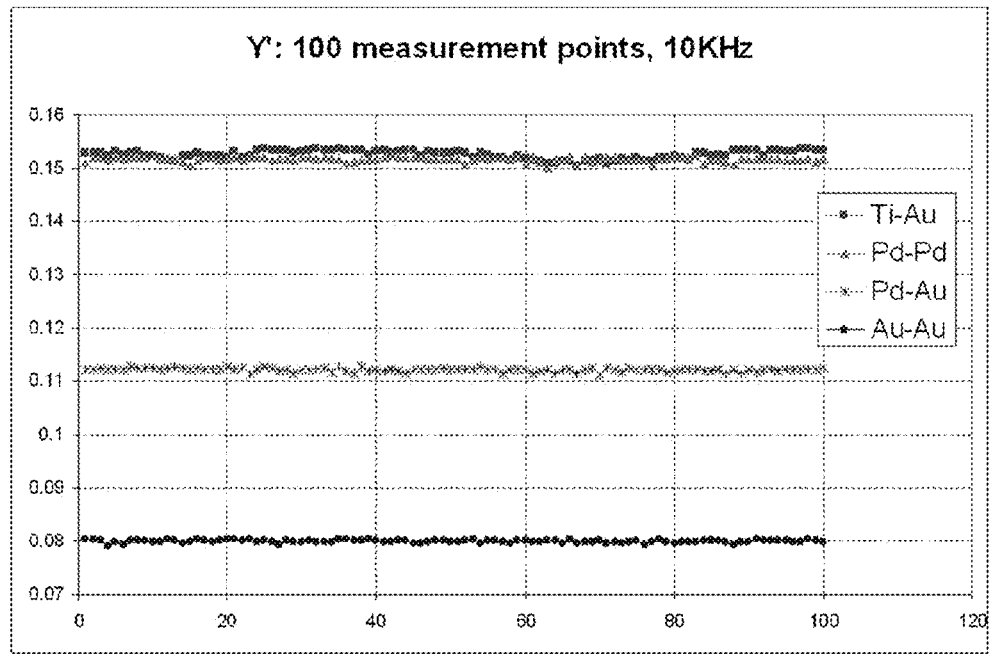
FIGS. 27A and 27B show multiple measures of the in-phase and quadrature components of the complex admittance, respectively, for 2 mg/ml of Dopamine at 10 kHz, measured at each of four unique electrode combinations.
Figure 27B:
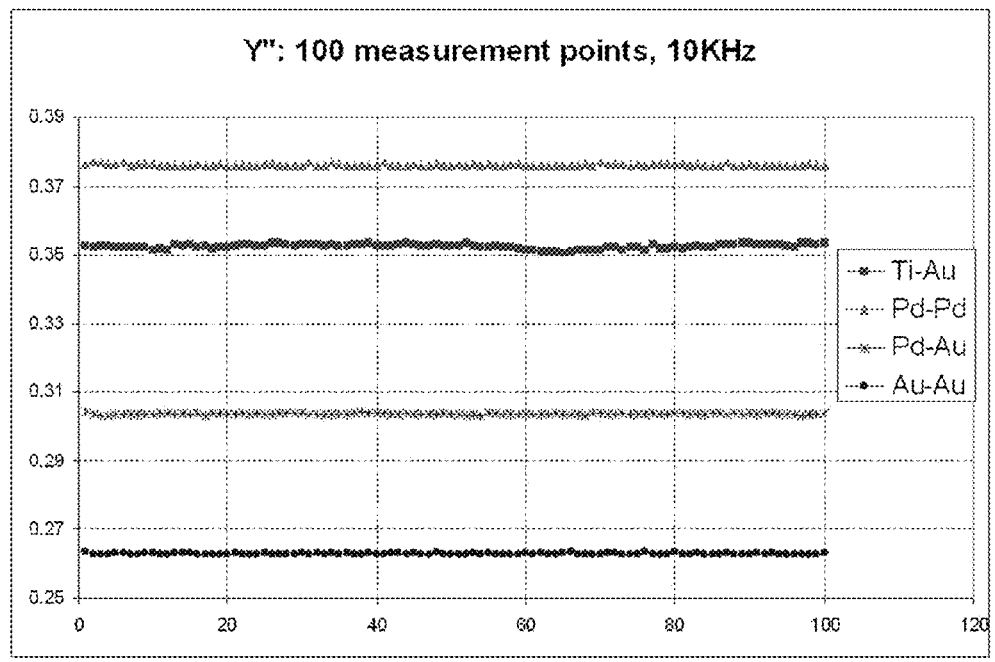
Figure 28A:
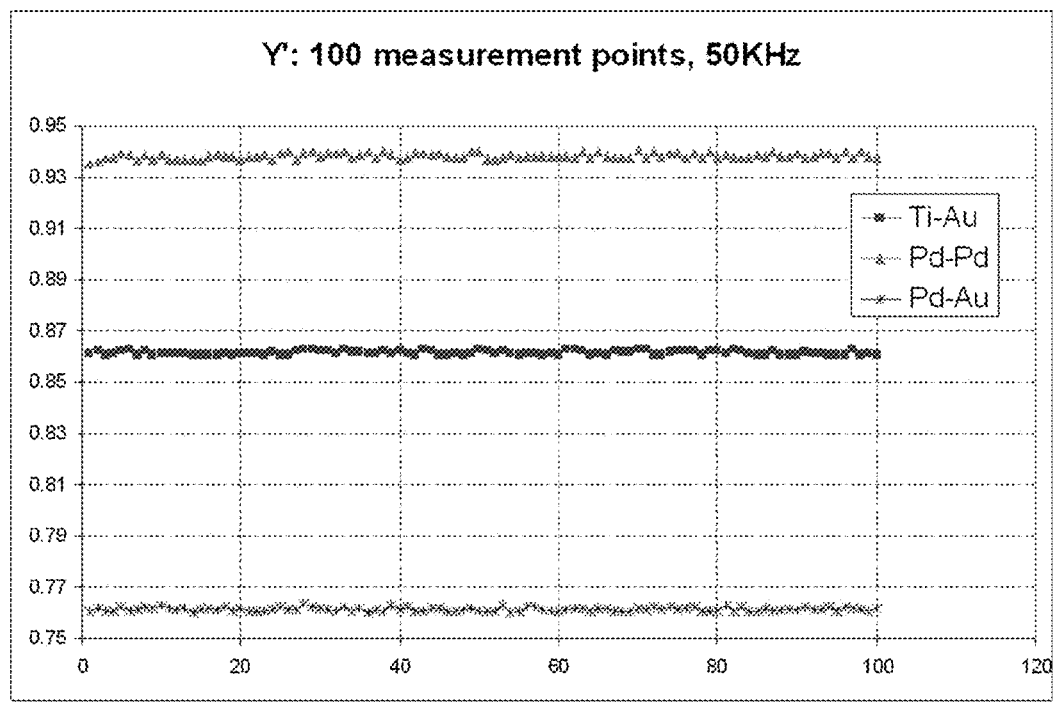
FIGS. 28A and 28B show multiple measures of the in-phase and quadrature components of the complex admittance, respectively, for 2 mg/ml of Dopamine at 50 kHz, measured at each of four unique electrode combinations.
Figure 28B:
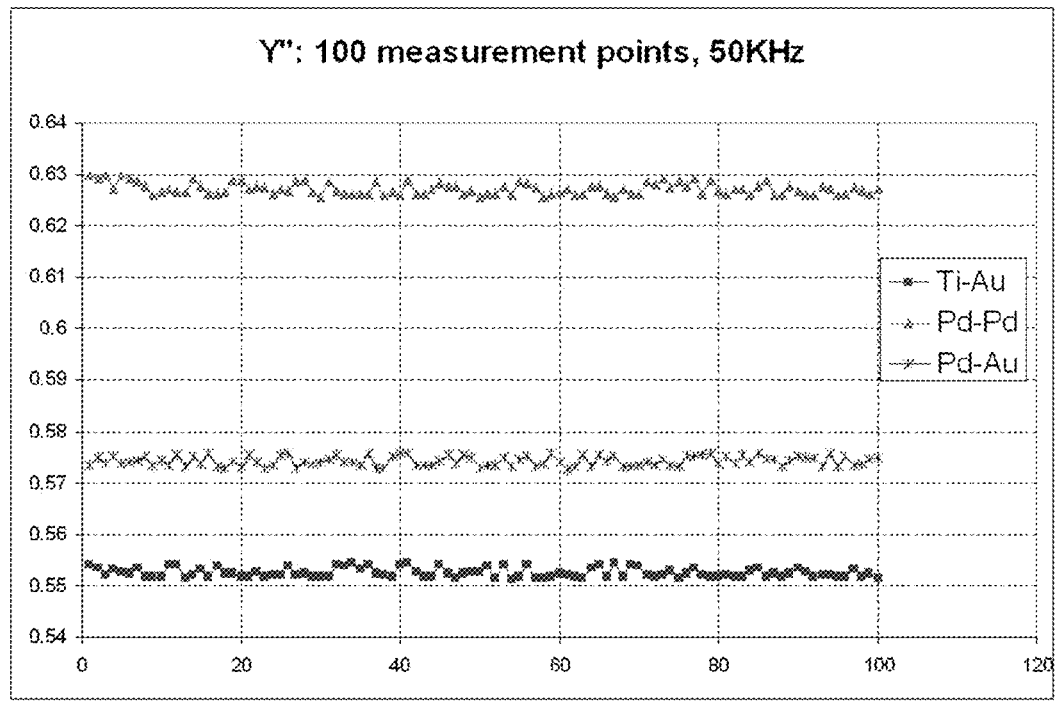
Figure 29A:
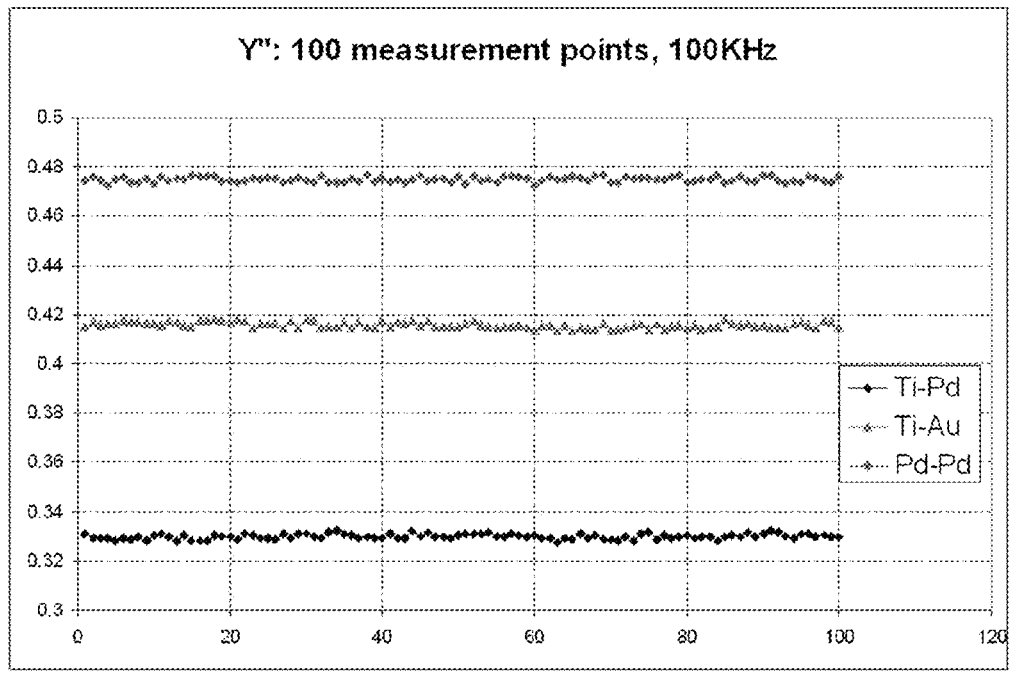
FIGS. 29A and 29B show multiple measures of the in-phase and quadrature components of the complex admittance, respectively, for 2 mg/ml of Dopamine at 100 kHz, measured at each of four unique electrode combinations.
Figure 29B:
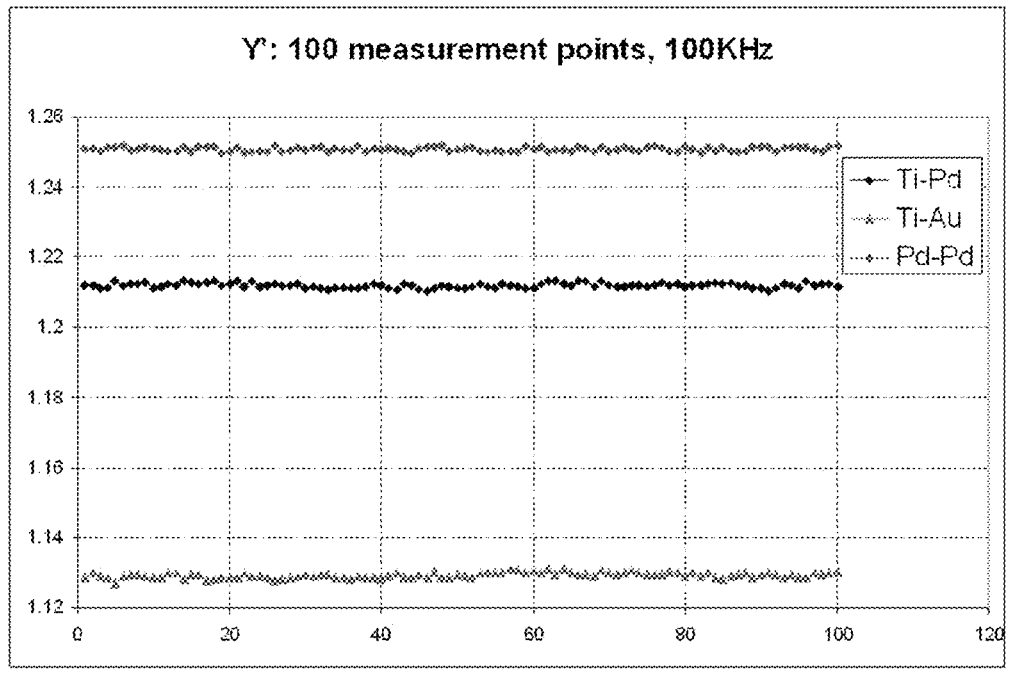

The admittance spectrographic fingerprints taken using the prototype also demonstrated remarkable stability and reproducibility. For example, FIGS. 27A-27 show the stability of the complex admittance measurements (both in-phase in FIG. 27A and quadrature in FIG. 27B) when measuring 2 mg/ml of Dopamine at 10 kHz. The y-axis shows the measurement number, and the x-axis shows the measured value. This stability is not frequency dependent, as demonstrated in FIGS. 28A-28B and 29A-29B, which examined the frequency at 50 and 100 kHz, respectively.

Admittance spectrographic fingerprints such as those described above (e.g., FIGS. 19A-26C) were used to train a processor to recognize the patterns of these known substances. The processor was then provided with a series of "unknown" mixtures to which "noise" had been artificially added. The unknown mixtures were selected from the list of tested compounds within the tested concentration ranges. The processor correctly identified all of the unknown compounds, even after the addition of up to 30% noise (random noise) on top of the original fingerprint signal.

Other exemplary systems have been designed as well. For example, in one variation, a complex admittance system including multiple admittance electrodes has been developed for IV fluid monitoring and identification system configured for insertion into the IV line between the IV source (bag) and the catheter where the flow enters the patient using Luer Lock fittings. Alternatively, it may be incorporated into the IV tubing set when it is manufactured. In either case, it will preferably be located downstream of the last injection port. In includes two or more sensor technologies and provides a continuous stream of data from multiple data channels. This data is processed by software algorithms to generate a pattern of sensor responses. When a fluid or drug is injected into or begins flowing through the IV line, the sensor responses will change and the new set of responses are compared to a database of known patterns. When a match is found, the system indicates the drug and instantaneous concentration and flow rate. By integrating concentration and flow rate over time, the total dosage is calculated and displayed.

Another example of an IV sensor system for drug identification includes a plurality of complex admittance electrodes configured for admittance measurements on at least 2 electrodes and preferably 6 or more electrode pairs. The sensor system may incorporate 1 or more admittance measurement channels and 1 or more optical measurement channels. In some variations, the system incorporates 12 admittance measurement channels and 3 or more optical measurement channels. Measurement of admittance may be performed at multiple frequencies, preferably in the range from 1 Hz to 1 Mhz and more preferably in the range of 1 kHz to 500 kHz and even more preferably in the range of 5 kHz to 200 Khz. The optical sensors may simultaneously be sensitive to absorption and refractive index, and may include measuring of evanescent wave effects. Fluid optical absorption and refractive index sensors may operate at discrete wavelengths between 250 and 1500 nM, for example, with a tunable wavelength sources between 250 and 1500 nM. Multiple wavelength measurement of absorption and refractive index may provide multiple dimensions for recognition algorithms. Additional sensors may include color sensors based on a white light and a filter based detection system. For example, a white light LED in conjunction with a detector incorporating red, green and blue filters. Color sensors based on red, green and blue sources in conjunction with a single detector to measure in sequence the intensity of each source. Optical sensors may operate with time varying excitation such as pulse or sine wave. Optical detectors for time varying signals may incorporate lock-in detection methods, and optical sources may incorporate intensity feedback for improved stability. Any of the processors described herein may incorporate multi-dimensional data clustering, pattern recognition and/or neural network algorithms applied for drug recognition from training patterns generated by testing known materials.

Applications/Methods of Use

In general, the devices and systems described herein may be used to determine the composition of a fluid, and particularly a medical fluid such as an intravenous or parenteral fluid. The composition may be determined for all or a subset of the components of the fluid. It is a particular strength of the systems, devices and methods described herein that they may be configured to determine, either the identity or concentration or essentially simultaneously, both the identity and concentration of all of the components in the solution, including identification of the carrier solution itself. Further, the systems described herein may have a very quick response time (on the order of msec or seconds), and may be configured to provide control or alerts in real time.

In particular, the systems and methods described herein may be used for the validation of pharmacy stock solutions. For example, a complex admittance system may be programmed to recognize specific commonly used stock solutions delivered intravenously or used to compound/formulate medication solutions for intravenous delivery, such as but not limited to normal saline, ringer's solution, 2.5%, 5% or 10% dextrose in water, 5% dextrose in ¼-, ½-, or normal saline, lactated ringer's solution, 5% dextrose in ringer's solution, 5% dextrose in lactated ringers solution, dextran 6% in D5W or normal saline, fructose 10% in water or normal saline, or Invert sugar 10% in water or normal saline. Improperly made or expired stock solutions will produce signatures that depart from that of properly made solutions and the system will detect and warn the operator of the discrepancy.

In some variations, the complex admittance systems and devices described herein may be used for validation and quantization of pure pharmacy medical/medication solutions. For example, a complex admittance system may be programmed to recognize specific drug compounds at standard and non-standard concentrations in their compatible carrier solutions such as normal saline, dextrose etc. as listed above. The system may produce an independent identification/confirmation of the drug and carrier solution and estimate the concentration of the drug in the carrier solution. When the drug concentration or carrier solution are not consistent with normal hospital/clinic formulation practices or recommended doses, the system will generate a warning for the operator. The system may provide guidance or suggestions regarding the guidelines used to generate the error message and possible remediation steps. The system can produce an electronic or paper record of the drug, dose, and carrier solution.

The complex admittance system and devices described herein may also provide validation and quantization of combination pharmacy medical/medication solutions. For example, a complex admittance system may be programmed to recognize specific combinations of drug compounds commonly formulated together at standard and non-standard concentrations in their compatible carrier solutions such as normal saline, dextrose etc. as listed above. The system will produce an independent identification/confirmation of the drugs and carrier solution and estimate the concentration of each drug in the carrier solution. When the drug concentrations or carrier solution are not consistent with normal hospital/clinic formulation practices or recommended doses, the system will generate a warning for the operator. The system may provide guidance or suggestions regarding the guidelines used to generate the error message and possible remediation steps. The system can produce an electronic or paper record of the drug, dose, and carrier solution.

In some variations, the complex admittance systems and devices may be used for the identification of counterfeit medications. For example, a complex admittance system may be programmed to recognize specific drug compounds. In the case of counterfeit medications, the different makeup of a counterfeit drug will be detected and a warning can be generated.

Similarly, a complex admittance system may be useful for the identification of contaminated or adulterated medications. A complex admittance system may be programmed to recognize specific drug compounds. In the case of contaminated or adulterated medications, the contaminant or additive will produce an unexpected signal and the sensor system will warn of this potentially dangerous condition.

A complex admittance system may also be useful for the identification of liquid medications which have lost their potency or decomposed resulting from improper storage or preparation conditions or long-term storage that has exceeded the limits allowable for the medication. A complex admittance system may be programmed to recognize specific drug compounds. In the case of medications which have decomposed due to improper storage or preparation or during long term storage, the decomposition products combined with the lower concentration of active drug will produce an unexpected signal and the sensor system will warn of this potentially dangerous condition.

A complex admittance system, device and method may also be used for detection of narcotic diversion. Substitution or dilution of and subsequent diversion of narcotics is a problem in healthcare environments. Proper pain management requires that the patient receive the prescribed dosage of medication. Any reduction of the concentration and or total dosage will result in unnecessary patient suffering. The complex admittance systems and devices described herein may be used for the detection of narcotic diversion. The lower concentration or smaller dosages or solution substitutions may be detected by our complex admittance system and a warning and log can be generated to ensure the patient receives the proper dosage.

The complex admittance systems and methods described herein may also be used to identify drug manufacturer, formulation, lot, etc. The complex admittance systems, devices and methods can be trained to recognize unique fingerprints of the same drugs supplied by different manufacturers. Different means of producing the drugs as well as different buffers and stabilizers, etc will be detected and can be used to identify the drug and manufacturer.

In some variations, the complex admittance systems, devices and methods may be used for identifying and documenting investigational drugs and doses delivered to patients in clinical studies. The system can be trained to recognize unique signatures of investigational drugs then used to document the dosing of those drugs in clinical trials. The system can also be trained to recognize unique signatures of control drugs or placebos and used to document their presence in appropriate patients in clinical studies.

A complex admittance system and device may be used in in-process control and validation of automated IV preparation. The system can be incorporated into a robotic IV preparation system such as the RIVA (Robotic IV Automation—Intelligent Hospital systems) or Cytocare (Health Robotics) systems, which automate preparation of general and oncology IVs respectively, to provide in-process and final product confirmation before the product is dispensed from the robot. It can also provide in-process verification of the ingredients to be combined into each IV solution to verify that the proper components have been loaded in the proper places, and are still consistent with the minimum use specifications for each component ingredient.

The complex admittance devices and systems described herein can also be uses in drug manufacturing. For example, complex admittance systems, devices and methods can be used in drug formulation facilities to provide online process monitoring and control of systems such as drug formulation systems, bioreactors, etc for drug and biotechnology formulation and manufacturing. The system can measure the presence and quantity of one or more desired manufacturing/bioreactor products and/or measure the presence and quantity of one or more undesirable byproducts. The system can be used to determine when bioreactor or formulation tank adjustments are required and when a system is ready for harvest.

In some variations the complex admittance systems and device may be used for medical applications for blood and body fluid testing. For example, the complex admittance systems, devices and methods described herein can also be used in the measurement of blood glucose, urea concentration, pharmaceutical drug levels, etc. in blood, urine, plasma, lymph, tears, saliva, and other body fluids either as a bench screen or in certain cases as an implantable monitoring device.

Complex admittance systems and devices described herein may also be used for testing for illegal drugs and alcohol levels in biological fluids. The complex admittance system, devices and methods described in this document can also be used to measure the presence and concentration of illegal drugs such as cocaine, marijuana, MDMA, Methamphetamine, LSD, Heroin, etc., and diverted legal medications such as Hydrocodone, Oxycontin, and steroids, etc in blood, urine, plasma, lymph, tears, saliva, and other biological fluids.

The complex admittance devices, systems and methods described herein may also be useful for measurement or validation of key ingredients in complex pharmaceutical fluids. For example, a complex admittance system can be used in the measurement of the presence or absence of key components of very complex pharmaceutical fluids such as TPNs (total parenteral nutrition) which can contain 20 or more ingredients but which contains several whose presence or proportion are critical to patient safety. The system can also be used to estimate the proportion of key components present in very complex pharmaceutical fluids such as insulin, glucose, dextrose, heparin, magnesium, potassium, calcium, and other key compounds.

While the methods, devices and systems for determining composition of a solution using admittance spectroscopy have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A system for determining the identity, concentration or identity and concentration of an intravenous drug solution by admittance spectroscopy to determine surface interactions of the intravenous drug solution on fluid-contacting surfaces of a plurality of pairs of electrodes, the system comprising:
   a sensor comprising a plurality of pairs of electrodes having fluid-contacting surfaces, wherein each pair of electrodes is configured to have different surface interactions with the solution at different frequencies than the other pairs of electrodes;
   a signal generator configured to provide current at a plurality of frequencies for application from one or more fluid-contacting surfaces of the sensor;
   a signal receiver configured to receive complex admittance data from a plurality of fluid-contacting surfaces of the sensor;
   a controller configured to coordinate the application of signals from the signal generator and the acquisition of complex admittance data from the sensor to create an admittance spectrographic fingerprint of the intravenous drug solution, wherein the controller is configured to apply electrical excitation to each pair of electrodes that results in a voltage that is below 500 mV and below the threshold level for electrochemical reactions, further wherein the admittance spectrographic fingerprint comprises complex admittance information indicative of surface interactions between the intravenous drug solution and the fluid-contacting surfaces of the sensor; and
   a processor configured to receive the admittance spectrographic fingerprint and to determine the identity, concentration or identity and concentration of the intravenous drug solution by comparing the admittance spectrographic fingerprint to a library of admittance spectrographic data comprising complex admittance data measured from a plurality of known compounds and mixtures of compounds in a carrier solution at a plurality of frequencies and known concentrations.

2. The system of claim 1, wherein the fluid-contacting surfaces of each pair of electrodes in the plurality of electrodes of the sensor are formed of different materials.

3. The system of claim 1, wherein the fluid-contacting surfaces of each pair of electrodes in the plurality of electrodes of the sensor are formed of different geometries.

4. The system of claim 1, wherein the sensor comprises at least three different fluid-contacting surfaces formed of different materials, different geometries or different materials and geometries.

5. The systems of claim 1, wherein the sensor is configured to be single-use.

6. The system of claim 1, wherein the fluid-contacting surfaces of the sensor are calibrated to a predetermined standard that matches complex admittance data of the library of admittance spectrographic data.

7. The system of claim 1, further comprising a measurement cell configured to receive the intravenous drug solution so that the fluid-contacting surfaces of the sensor contact the intravenous drug solution.

8. The system of claim 1, wherein the signal generator is configured to apply an electrical excitation frequency from about 1 Hz to about 1 MHz.

9. The system of claim 1, further comprising a display configured to display the identity and concentration of the one or more compounds within the intravenous solution.

10. The system of claim 1, wherein the processor is further configured to determine the identity of the carrier solution of the intravenous drug solution.

11. The system of claim 1, wherein the library of predetermined complex admittance data comprises complex admittance data measured for a plurality of individual compounds and mixtures of compounds in a carrier solution at a plurality of frequencies.

12. The system of claim 1, wherein the processor comprises recognition logic configured to determine the likeliest match between the admittance spectrographic fingerprint and the library of admittance spectrographic data.

13. The system of claim 12, wherein the recognition logic comprises an adaptive neural network trained on the library of admittance spectrographic data.

14. The system of claim 1, wherein the sensor further comprises a second sensor element, and further wherein the processor is configured to use data from the second sensor element in addition to the complex admittance data to determine both the identity and the concentration one or more compounds in the intravenous drug solution.

15. The system of claim 14, wherein the second sensor element comprises an optical sensor.

16. A benchtop drug solution analyzer for determining the identity, concentration or identity and concentration of a drug solution by admittance spectroscopy to determine surface interactions of the drug solution on fluid-contacting surfaces of a plurality of electrodes, the analyzer comprising:
   a measurement cell comprising a plurality of electrodes having fluid-contacting surfaces, the measurement cell configured to receive a sample of the drug solution so that the drug solution is contacted by the plurality of electrodes;
   a signal generator configured to provide electrical excitation at a plurality of frequencies for application from a plurality of pairs of electrodes of the measurement cell, wherein each pair of electrodes is configured to have different surface interactions with the solution at different frequencies than the other pairs of electrodes;
   a signal receiver configured to receive complex admittance data from the plurality of pairs of electrodes of the measurement cell;
   a controller configured to coordinate the application of signals from the signal generator, and the acquisition of complex admittance data from the signal receiver, to create an admittance spectrographic fingerprint of the drug solution, wherein the controller is configured to apply electrical excitation to each pair of electrodes that results in a voltage that is below 500 mV and below the threshold level for electrochemical reactions, further wherein the admittance spectrographic fingerprint comprises complex admittance information indicative of surface interactions between the drug solution and the fluid-contacting surfaces; and a processor configured to receive the admittance spectrographic fingerprint and to determine the identity, concentration or identity and concentration of one or more compounds in the drug solution by comparing the admittance spectrographic fingerprint to a library of admittance spectrographic data comprising complex admittance data measured from a plurality of known compounds and mixtures of compounds in a carrier solution at a plurality of frequencies and known concentrations.

17. The analyzer of claim 16, further comprising a housing at least partially enclosing the signal generator, single receiver and controller.

18. The analyzer of claim 16, further comprising a plurality of single-use measurement cells.

19. The analyzer of claim 16, wherein the measurement cell comprises at least three different fluid-contacting surfaces formed of different materials, different geometries or different materials and geometries.

20. The analyzer of claim 16, wherein the fluid-contacting surfaces of the measurement cell are calibrated to a predetermined standard that matches complex admittance data of the library of admittance spectrographic data.

21. The analyzer of claim 16, wherein the signal generator is configured to apply a current frequency from about 1 Hz to about 1 MHz.

22. The analyzer of claim 16, further comprising a display configured to display the identity and concentration of the one or more compounds within the drug solution.

23. The analyzer of claim 16, wherein the processor is further configured to determine the identity of the carrier solution of the drug solution.

24. The analyzer of claim 16, wherein the library of predetermined complex admittance data comprises complex admittance data measured for a plurality of individual compounds and mixtures of compounds in a carrier solution at a plurality of frequencies.

25. The system of claim 16, wherein the processor is configured to receive the admittance spectrographic fingerprint and to simultaneously determine identity and concentration of one or more compounds in the drug solution.

26. The analyzer of claim 16, wherein the processor comprises recognition logic configured to determine the likeliest match between the admittance spectrographic fingerprint and the library of admittance spectrographic data.

27. The analyzer of claim 26, wherein the recognition logic comprises an adaptive neural network trained on the library of admittance spectrographic data.

28. The analyzer of claim 16, wherein the measurement cell further comprises a second sensor element, and further wherein the processor is configured to use data from the second sensor element in addition to the admittance spectrographic fingerprint to determine both the identity and the concentration of one or more compounds in the drug solution.

29. The system of claim 28, wherein the second sensor element comprises an optical sensor.

* * * * *